(12) United States Patent
Kotsopoulou et al.

(10) Patent No.: US 9,534,246 B2
(45) Date of Patent: Jan. 3, 2017

(54) METHOD FOR SELECTING HIGH PRODUCING CELL LINES

(75) Inventors: Ekaterini Kotsopoulou, Stevenage (GB); Richard Priest, Stevenage (GB); Mark Uden, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 184 days.

(21) Appl. No.: 13/704,711

(22) PCT Filed: Jun. 29, 2011

(86) PCT No.: PCT/EP2011/060948
§ 371 (c)(1),
(2), (4) Date: Dec. 17, 2012

(87) PCT Pub. No.: WO2012/001073
PCT Pub. Date: Jan. 5, 2012

(65) Prior Publication Data
US 2013/0090259 A1    Apr. 11, 2013

Related U.S. Application Data

(60) Provisional application No. 61/360,553, filed on Jul. 1, 2010.

(51) Int. Cl.
*C12Q 1/06* (2006.01)
*G01N 33/566* (2006.01)
(Continued)

(52) U.S. Cl.
CPC ............... *C12Q 1/06* (2013.01); *C12P 21/02* (2013.01); *G01N 33/5005* (2013.01); *G01N 33/5044* (2013.01); *G01N 33/566* (2013.01); *G01N 33/56966* (2013.01); *G01N 33/577* (2013.01); *G01N 33/582* (2013.01); *G01N 15/14* (2013.01)

(58) Field of Classification Search
CPC ........... C12Q 1/06; C12P 21/02; G01N 15/14; G01N 33/5005; G01N 33/5044; G01N 33/566; G01N 33/56966; G01N 33/577; G01N 33/582

See application file for complete search history.

(56) References Cited

U.S. PATENT DOCUMENTS

| 4,824,775 A | 4/1989 | Dattagupta et al. |
| 7,446,179 B2 * | 11/2008 | Jensen ............... A61K 35/15 435/328 |

(Continued)

FOREIGN PATENT DOCUMENTS

| EP | 0 532 359 A1 | 3/1993 |
| WO | WO2008121757 | * 10/2008 |
| WO | 2010/022961 | * 3/2010 |

OTHER PUBLICATIONS

Lavergne-Mazeau et al. Applied and Environmental Microbiology, vol. 62; No. 8;1996;pp. 3042-3046.*

(Continued)

*Primary Examiner* — Gail R Gabel
(74) *Attorney, Agent, or Firm* — James J. Kang; Andrea V. Lockenour

(57) ABSTRACT

The invention provides methods for the rapid identification and selection of cell lines suitable for biopharmaceuticals production, which do no utilize animal derived components.

9 Claims, 30 Drawing Sheets

(51) Int. Cl.
*G01N 33/577* (2006.01)
*C12P 21/02* (2006.01)
*G01N 33/50* (2006.01)
*G01N 33/569* (2006.01)
*G01N 33/58* (2006.01)
*G01N 15/14* (2006.01)

(56) References Cited

U.S. PATENT DOCUMENTS

| | | | | |
|---|---|---|---|---|
| 8,728,828 B2* | 5/2014 | Berg | | G01N 33/558 210/656 |
| 2010/0028904 A1* | 2/2010 | Appelbaum et al. | | 435/7.1 |
| 2011/0281751 A1* | 11/2011 | Jostock | | C12N 15/1037 506/9 |

OTHER PUBLICATIONS

Fukuda et al. Appl Microbiol Biotechnol (2007) 76:151-158.*
Brezinsky et al., 2003. A simple method for enriching populations of transfected CHO cells for cells of higher specific productivity. J. Immunological Meth. 277: 141-155.*
Marder et al., 1990. Selective cloning of hybridoma cells for enhanced immunoglobulin production using flow cytometric cell sorting and automated laser nephelometry. Cytometry 11: 498-505.*
Lloyd et al., 2000. Relationship between cell size, cell cycle and specific recombinant protein productivity. Cytotechnology 34: 59-70.*
Romagnani et al., 1981. Surface immunoglobulins are involved in the interaction of Protein A with human B cells and in the triggering of B cell proliferation induced by Protein A-containing *Staphylococcus aureus*. J. Immunol. 127: 1307-1313.*
Akerstrom, B., et al., Journal of Immunology, vol. 135, No. 4, Oct. 1985, pp. 2589-2592.
Chai, Helen, et al., Enzyme and Microbial Technology, vol. 18, No. 2, 1996, pp. 126-132.
Hedhammar, et al., Journal of Biotechnology, vol. 119, No. 2, Sep. 23, 2005, pp. 133-146.
Kotsopoulou, Ekaterini, et al., Journal of Biotechnology, Apr. 15, 2010, vol. 146, No. 4, pp. 186-193.
Lavergne-Mazeau, F., et al., Applied and Environmental Microbiology, vol. 62, No. 8, 1996, pp. 6042-6046.
Marder, P., et al., Cytometry, vol. 11, No. 4, Jan. 1, 1990, pp. 498-505.
Nobuo Fukuda, et al., Applied Microbiology and Biotechnology, vol. 76, No. 1, May 15, 2007, pp. 151-157.
Oi, V. T., et al., The Journal of Cell Biology, vol. 93, No. 3, Jan. 1, 1982, pp. 981-986.
Palo,ares, Laura, A., et al., Biotechnology Letters, vol. 23, No. 5, Mar. 2001, pp. 359-364.
Parks, D. R., et al., PNAS, vol. 76, No. 4, Apr. 1, 1979, pp. 1962-1966.
Viau, Muriel, et al., Infection and Immunity, vol. 72, No. 6, Jun. 2004, pp. 3515-3523.

* cited by examiner

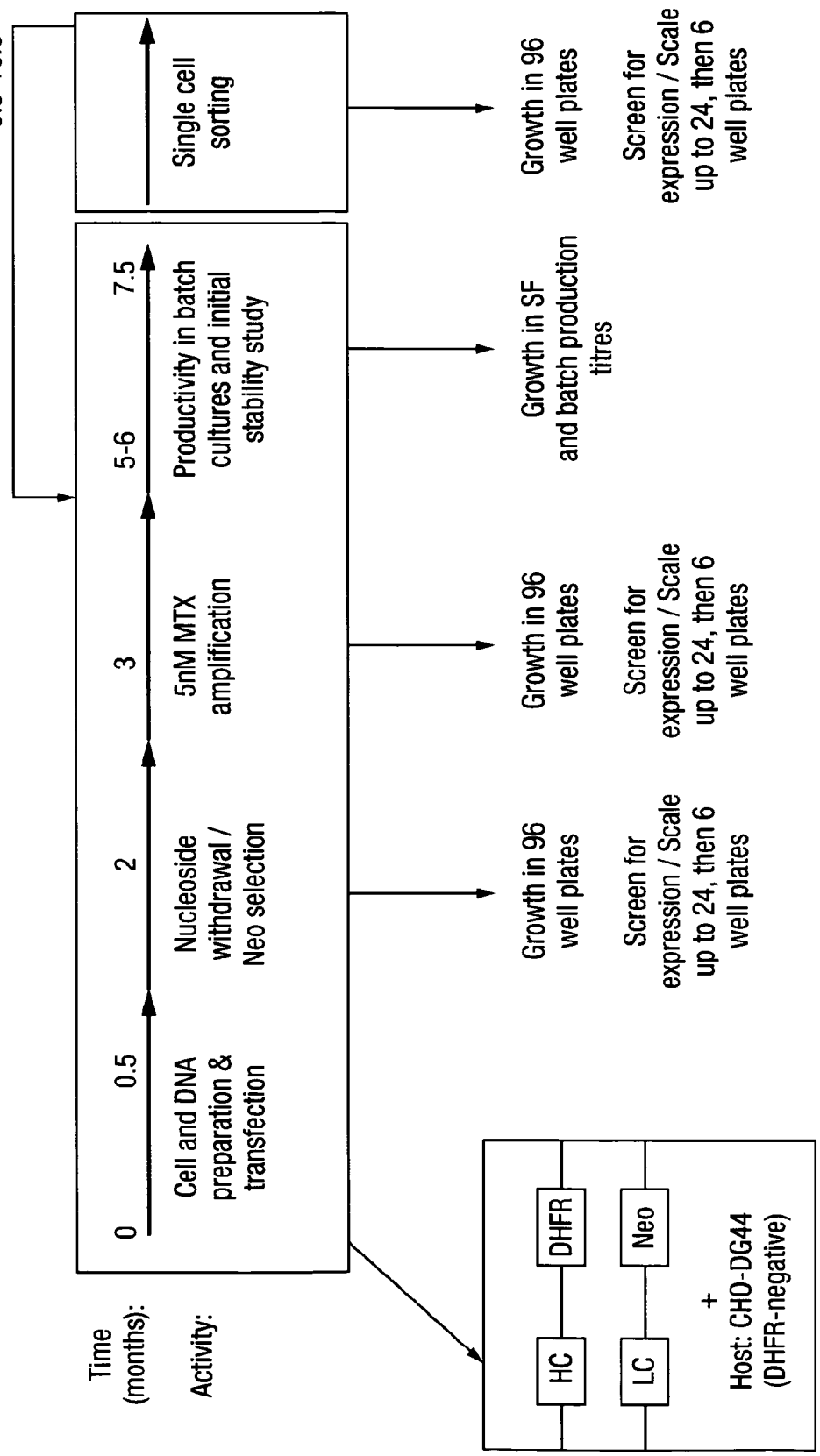

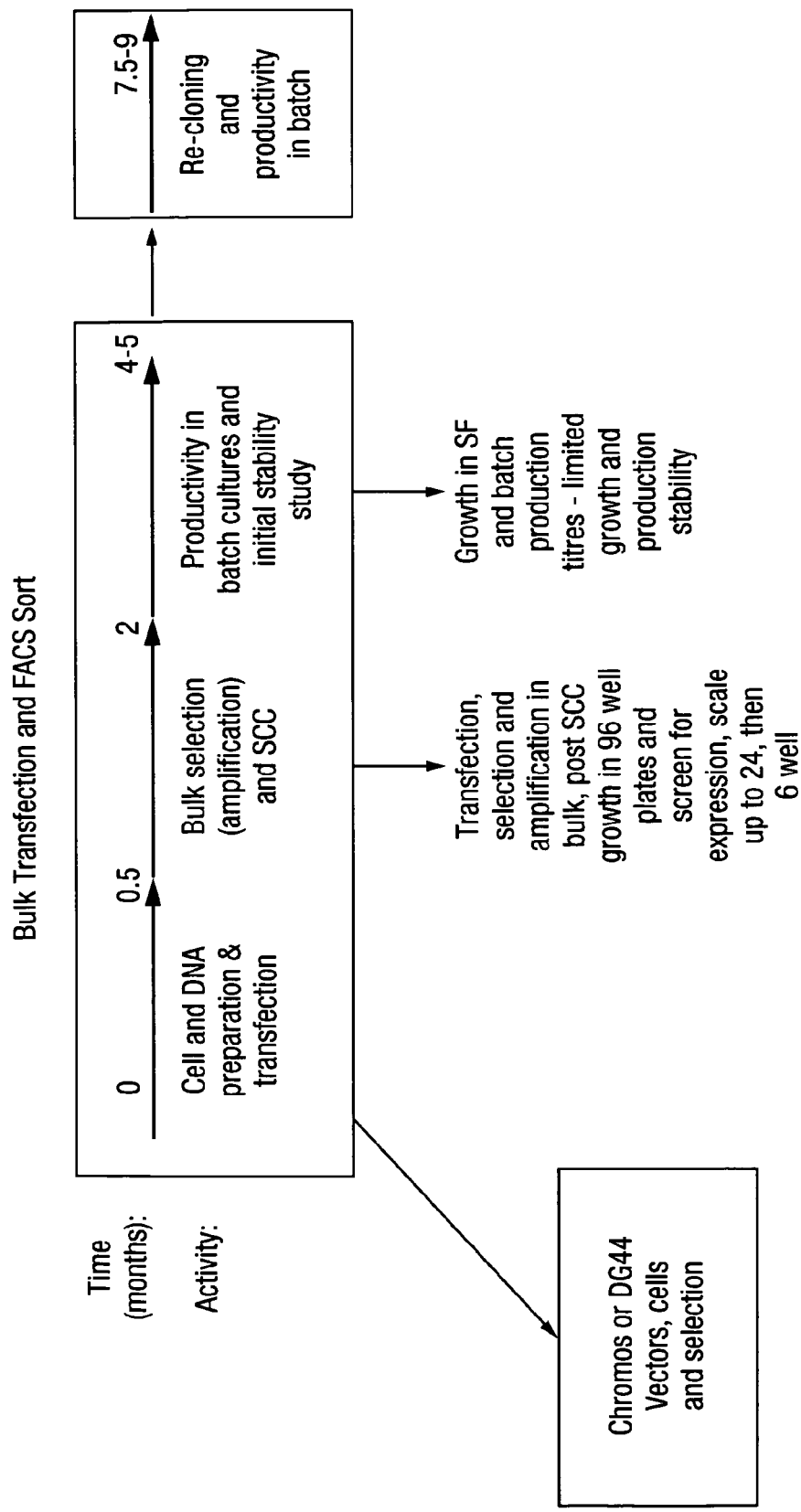

Fig. 1(C)
Heavy chain vector
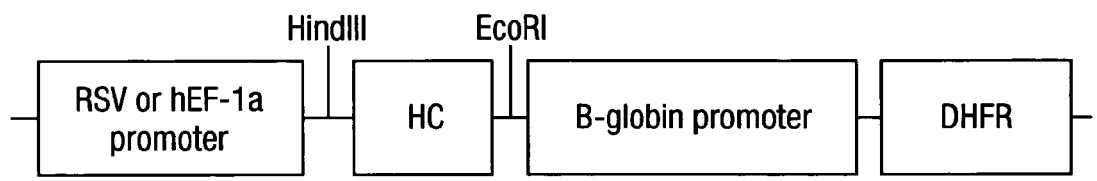
Light chain vector
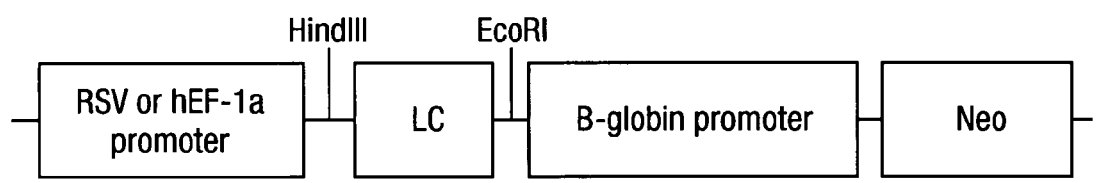

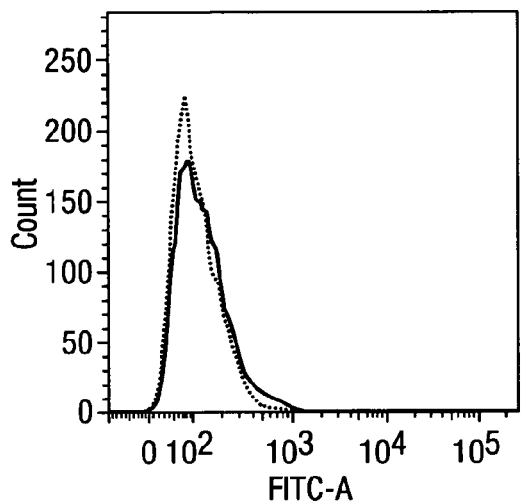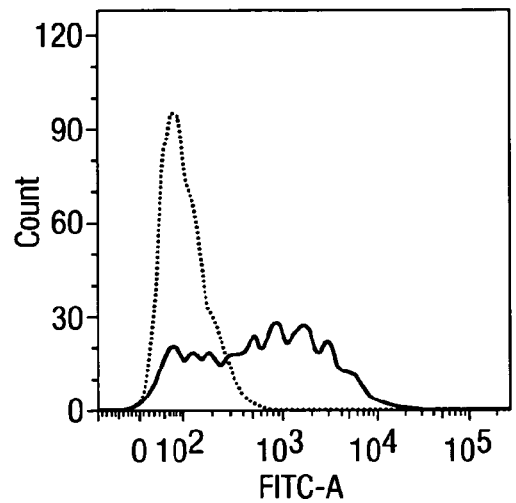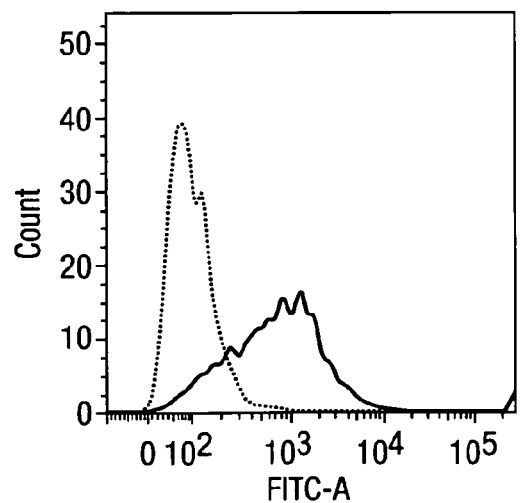

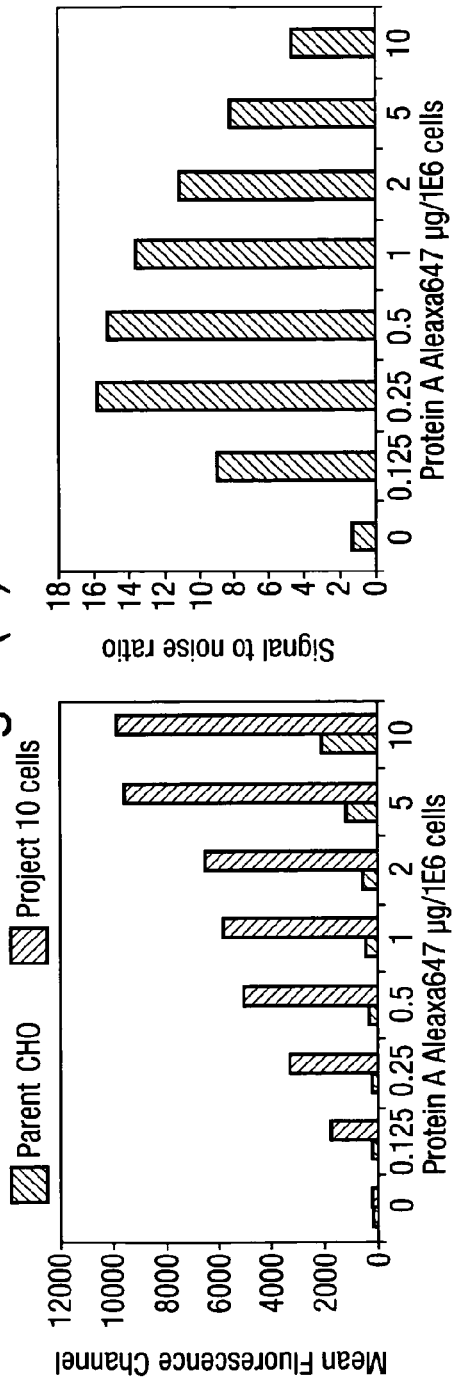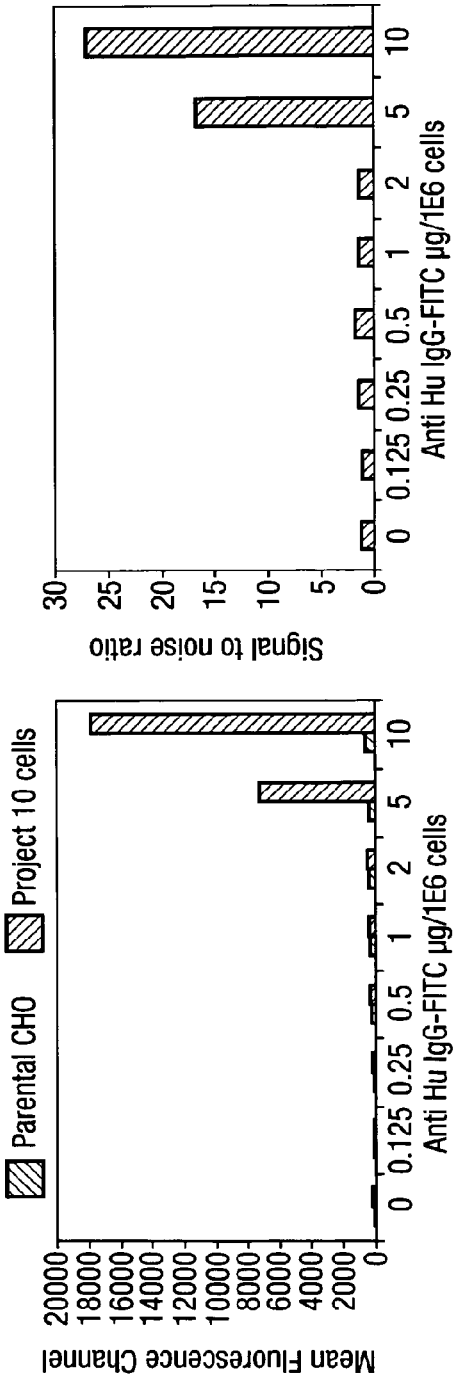

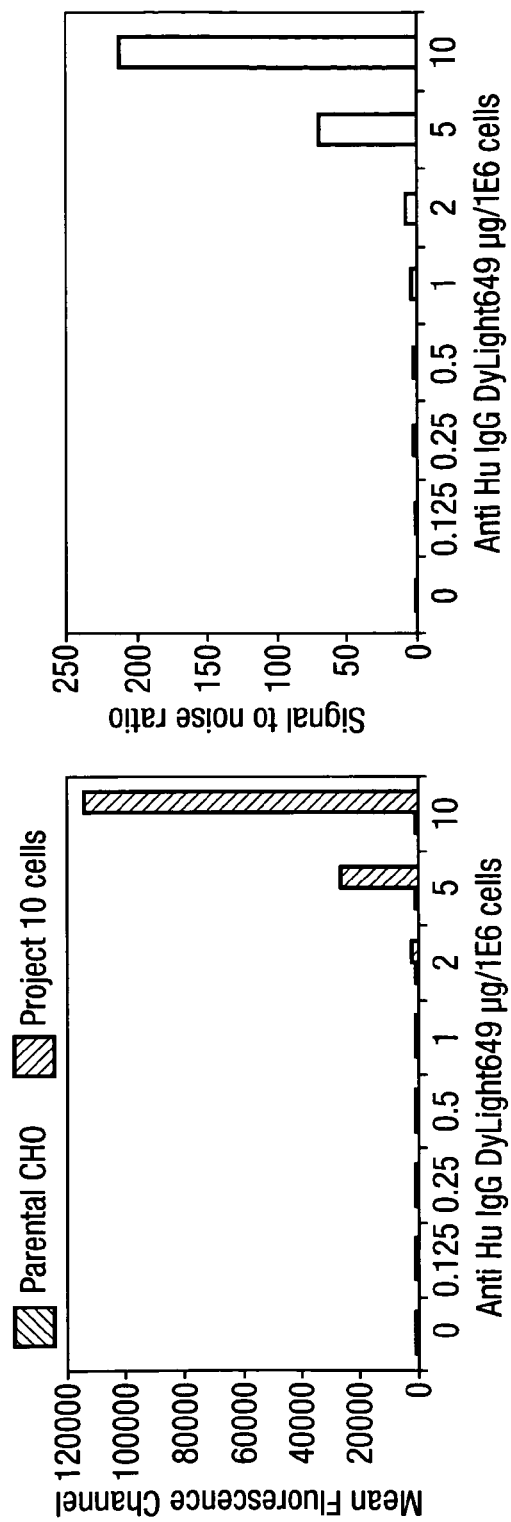

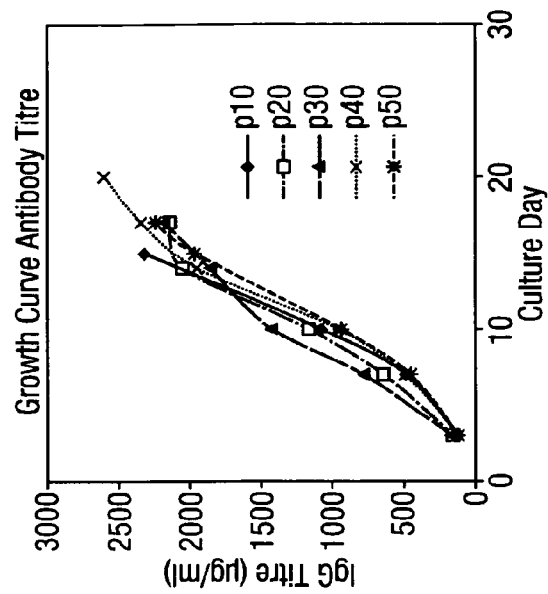

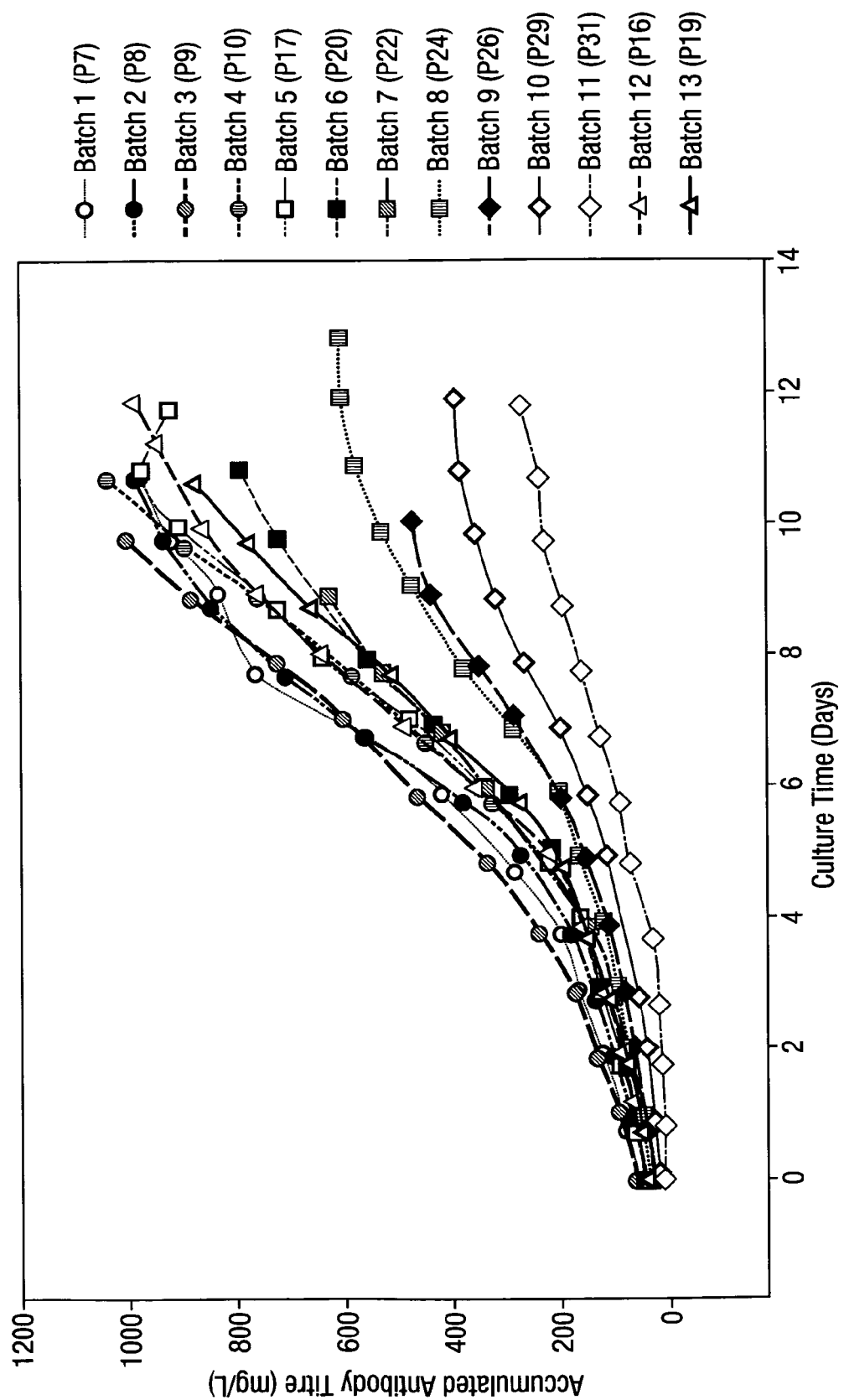

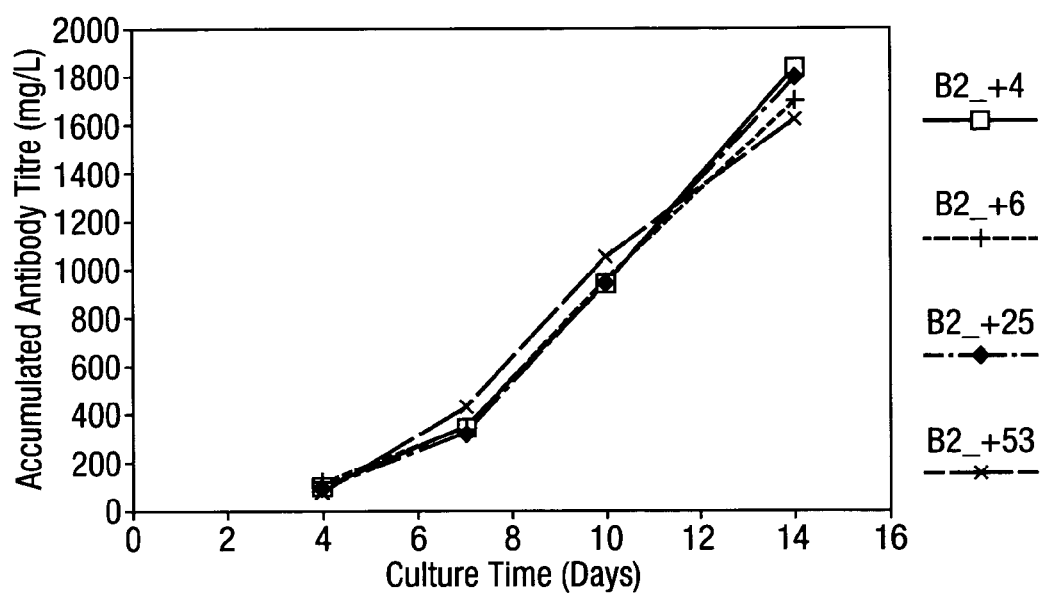

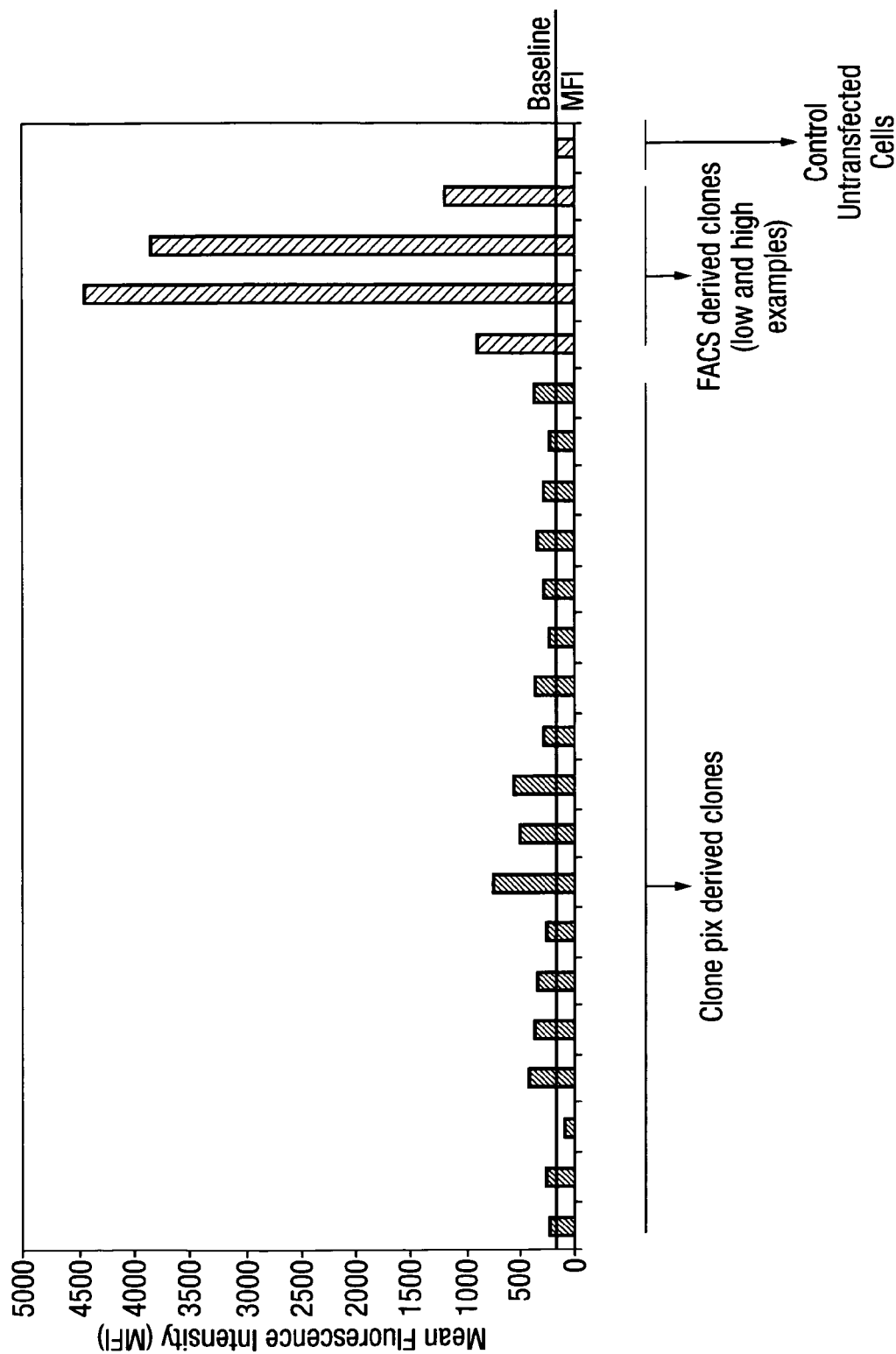

Fig. 21
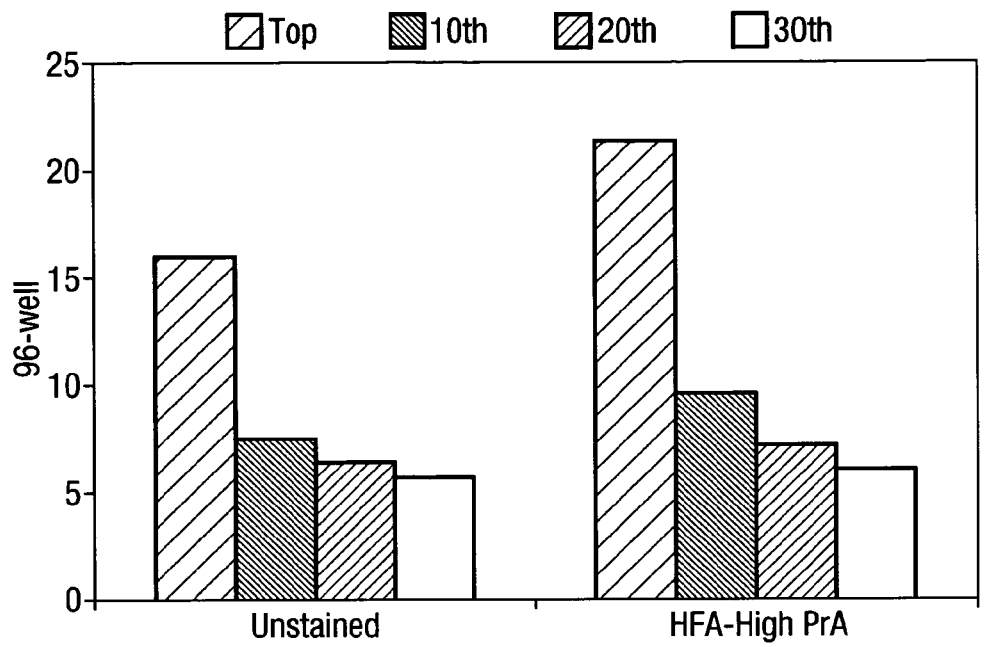
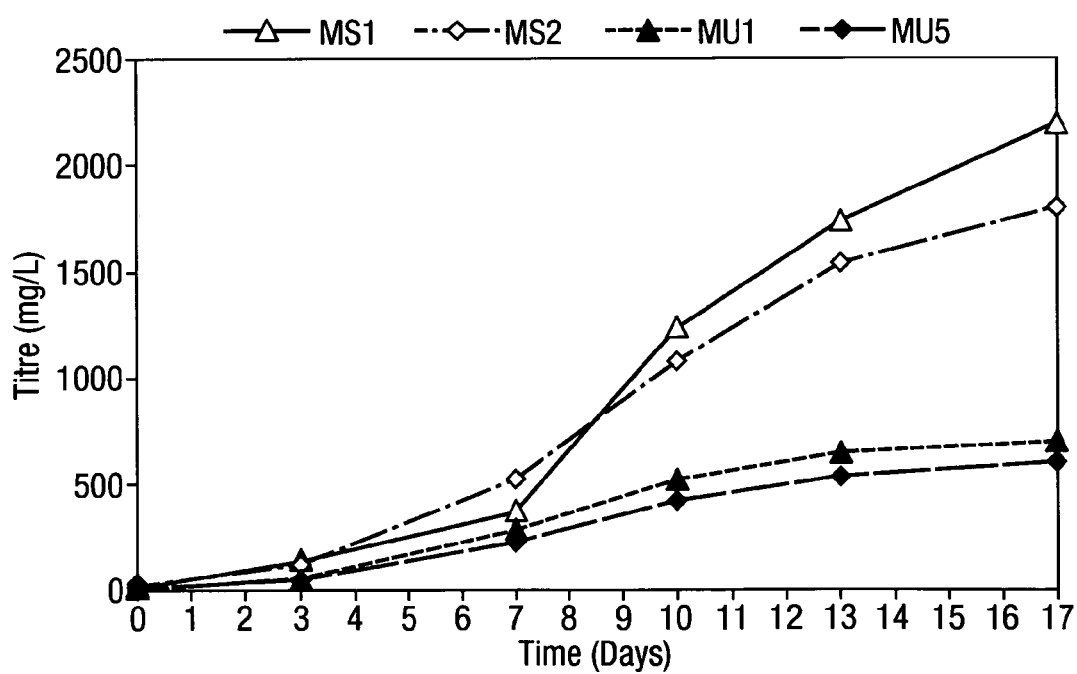

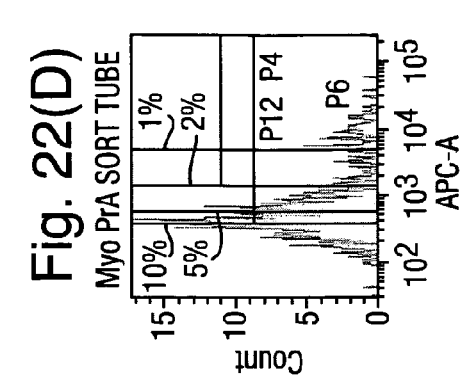
Fig. 22(D)
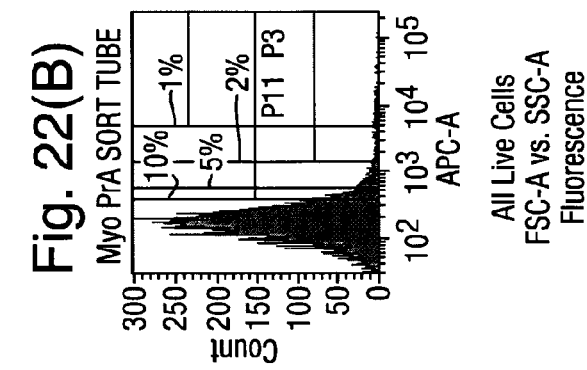
Fig. 22(B)
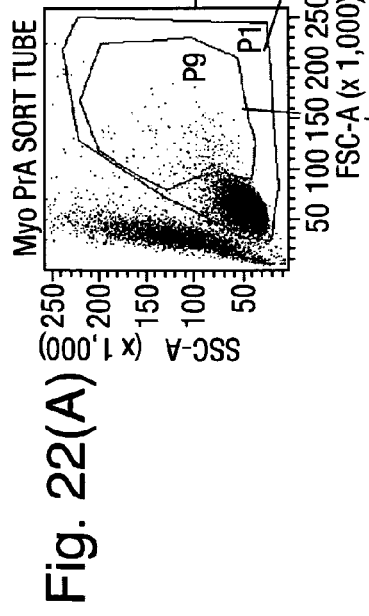
Fig. 22(C)
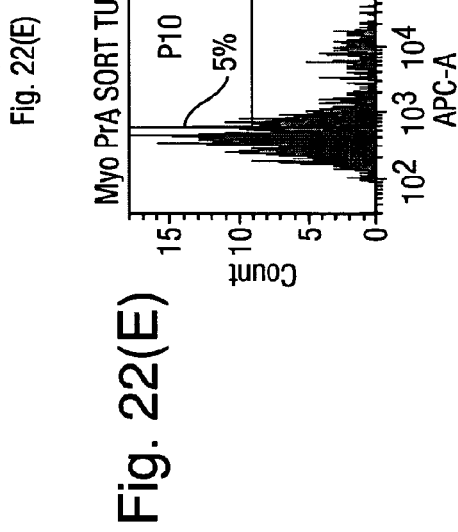
Fig. 22(A)
Fig. 22(E)

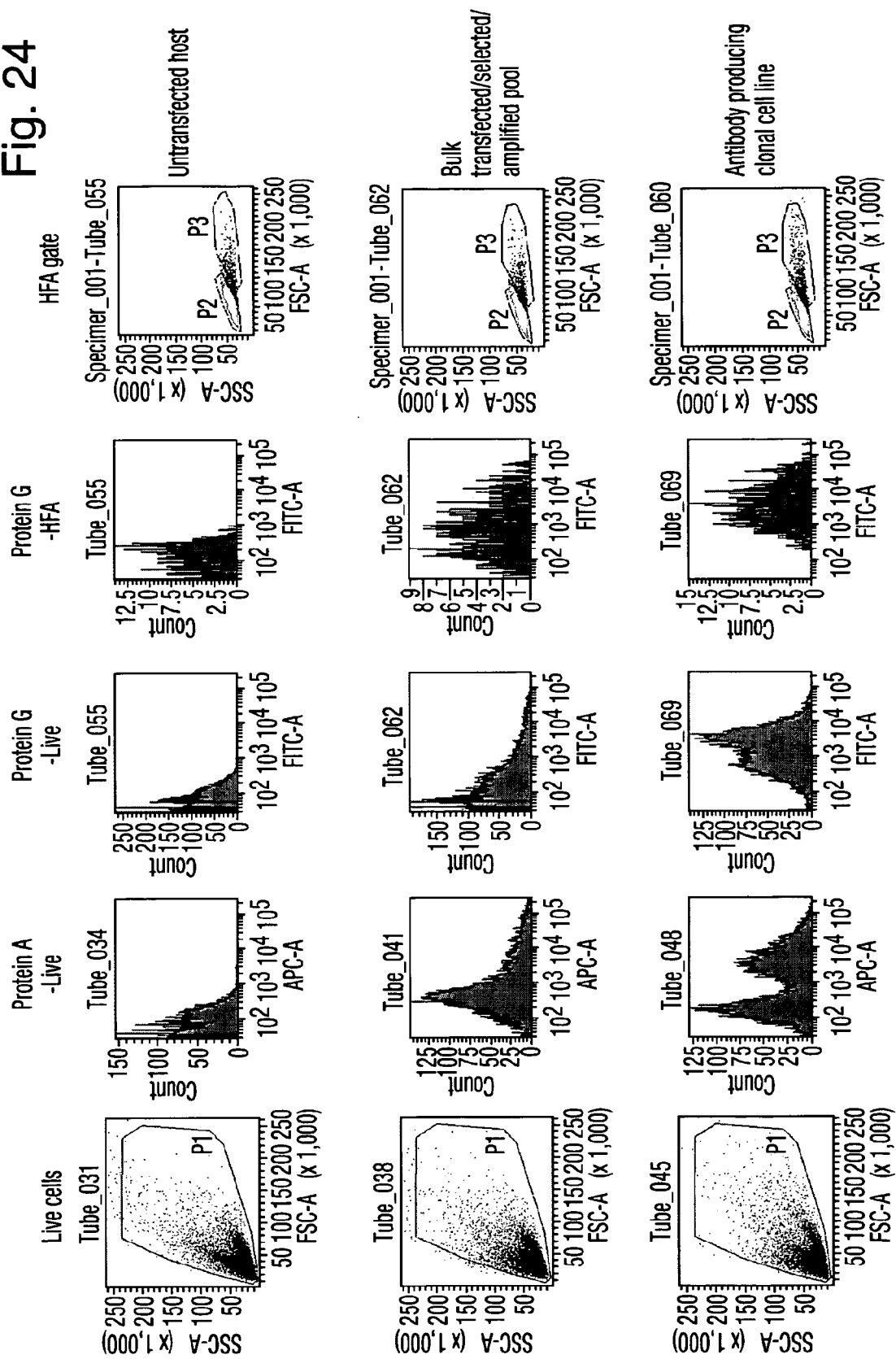

METHOD FOR SELECTING HIGH PRODUCING CELL LINES

This application is a 371 of International Application No. PCT/EP2011/060948, filed 29 Jun. 2011, which claims the benefit of U.S. Provisional Application No. 61/360,553, filed 1 Jul. 2010, both of which are herein incorporated by reference in their entireties.

TECHNICAL FIELD

The invention relates to the field of biopharmaceutical cell culture technology. In particular, this invention relates to a method for the rapid identification and selection of cell lines, and cell banks and manufacturing processes thereof, suitable for biopharmaceutical production. More particularly, this method involves the sorting of cells without the use of animal derived proteins. The invention also relates to novel gating strategies based on the forward scatter (FSC) properties of the cells.

BACKGROUND

Mammalian cells such as CHO (Chinese Hamster Ovarian cells), NS0 and PerC6 cells are routinely employed within the biopharmaceutical industry to manufacture biopharmaceuticals. These cells are genetically engineered and then selected in such a way so as to ensure that high titre expression of the desired protein is observed when the resulting cell lines are cultured in bioreactors.

Currently all approaches to select the best secreting cell clones involve the screening of hundreds to thousands of transfected cells to identify preferred clones with optimal growth and production profiles (e.g. see Wurm, 2004, Nature Biotechnology 22, 1393-1398). All such methodology requires considerable time and effort. As a consequence there is ongoing need for improved methodology to select for high yielding and stable cell lines. Such methodology should be faster, less labour and less resource intensive than current methodology. Typical current cell line development protocols involve the delivery of desired expression and selection cassettes into a desired host cell followed by plating, selection and growth of resulting genetically engineered cells in serum and animal derived component free (ADCF) media. Such ADCF media, first developed in the early 1990s, are now regularly employed to select and grow recombinant cells producing biopharmaceutical proteins intended for clinical use. The use of such cell culture media for this purpose ensures the mammalian cell lines generated are not exposed inadvertently to adventitious or transmissible agents of known or unknown origin. The use of such ADCF media thus forms part of a strategy to ensure resulting cell lines and thereby biopharmaceutical cell banks, processes, manufacturing plants and final products are not contaminated by such adventitious and transmissible agents be they cellular, viral or protein in origin. The use of ADCF media as part of a strategy to ensure contamination-free manufacturing not only addresses a theoretical risk to patients and manufacturing plants: biological drug products have previously been adulterated with adventitious agents (e.g. Huang W T et al Pharmacoepidemiol Drug Safety 2010, 19(3):306-310) and manufacturing sites have previously been closed due to contamination with such agents (e.g. see Garnick R L Dev Biol Standard 1998: 93 pp 21-9 & FDA web site notification (June 2009) regarding Vesivirus contamination of a manufacturing plant's bioreactors). Further details on such considerations and how best to reduce risks are well documented in ICH Quality Guide Q5A "Safety Evaluation of Biotechnology Products Derived From Cell Lines of Human or Animal Origin" (Step 4 Version September 1999).

Certain cell screening methodologies designed to identify optimal genetically engineered producer cells employ flow cytometry in order to reduce time and effort. When using flow cytometry to select engineered cell lines that secrete high levels of desired recombinant protein, two approaches have been adopted.

The first approach involves the selection of cells in which a fluorescent co-marker (e.g. GFP) or an enzyme such as DHFR (when combined with a fluorescent substrate) is over expressed. For such selection methods to succeed, one must attempt to link the expression of the markers with expression of the desired protein products. This linkage is required to ensure that cells expressing high levels of the marker also express and secrete high levels of the desired protein product. Examples of such an approach include Yoshikawa T et al 2001 (Biotech and Bioeng 74: 5 pp 435-442), Meng Y. G et al 2000 (Gene 25:242 (1-2) 201-207), deMaria et al 2007 (Biotechnol Prog 23, 475-72) and US 2004/0148647. However, there are drawbacks to this approach, in particular the fact that one is primarily selecting for high levels of marker expression and this does not always correlate with high expression and secretion of desired protein product. This approach also results primarily in the selection of final cells expressing extremely large amounts of marker. This can be disadvantageous, since high expression of a marker will compete with the desired protein product for host cell transcription, translation and processing apparatus, and thus the ultimate yield of the desired protein may be reduced. Furthermore such marker proteins can also be toxic (Liu H S et al 1999 (Biochem Biophys Res Commun 260 (3): 712-7)) and thereby inhibit cell line growth and production.

The second approach involves the direct selection of cells that secrete high levels of desired protein product. For an overview of FACS in general, see Shapiro: Practical Flow Cytometry, Fourth Edition, 2003, Wiley-Liss, ISBN#9780471411253. In a broad sense there are two FACS based methods for selection of high expression clones directly.

The first 'direct selection' FACS-based method exploits the observed correlation between membrane bound levels of desired protein product with secretion levels. An example of this approach can be found in Marder P et al 1990 Cytometry 11: 498-505. In this study the authors stained the membrane of hydridoma cells with fluorescently conjugated anti-product antibodies and then sorted and selected the most highly fluorescent cells. They then demonstrated that the resulting sub-clones exhibited enhanced IgG secretion levels in comparison to the cells prior to sorting. Subsequent reports with different cell lines have demonstrated similar results (e.g. see Brezinsky S et al 2003. Jn of Immunol (2003) 141-155).

A related but more complex alternative to staining and then sorting on membrane levels of product involves the use of product entrapment approaches such as the gel microdrop (GMD) technique or matrix-based secretion assays. In such approaches, secreted antibody is retained by either cross linkage to the cell membrane or within gel microdrops, or immobilised on an artificial matrix on the cell surface prior to FACS sorting with anti-product antibody on levels of fluorescence.

For a recent review on cytometry based cell sorting methods discussing both indirect selection approaches (i.e. via use of a marker) and direct selection approaches (i.e., via labelling of desired product associated with the cells) see Carroll and Al-Rubeai 2004 (Expert Opin Biol Ther 4: 1821-9) and Browne and Al-Rubeai 2007 (Trends Biotech, 25(9), 425-32).

However, whilst both direct and indirect labelling methods as described above are now proven successful, none to date are ideal for use in selecting high producing cell lines suitable for the manufacture of biopharmaceuticals. This is because, if the indirect approach is employed, one selects primarily for cells producing high marker levels as discussed above. Alternatively, all the direct selection methods to date employ animal derived anti-product antibodies and supporting reagents (e.g. foetal calf serum (FCS) or bovine serum albumin (BSA)), which are undesirable in the development and manufacture of biopharmaceuticals. Such animal reagents are also regularly employed to support cell viability during harsh flow sorting and plating procedures. This will again increase the risk of exposure to adventitious agents for any cell line thereby generated. Additionally, animal derived reagents such as serum or BSA are typically used to block non-specific binding prior to incubation of cells with the desired anti-product binding reagent such as anti-serum.

Recently, Applebaum et al. (US 2010/0028904), described a method to screen and select for high expressing cells by plating the cells in methylcellulose (semi-solid media) containing fluorescent Protein A/G to detect product expression. However, considerable challenges still remain with such methodology. Significantly, the fluorescent Protein A/G does not necessarily bind the protein of interest on the cell surface but rather the secreted protein around the cell (resulting in a "halo" around the cell mass). Indeed, Protein A primarily binds to antibody and Fc fusion proteins in the constant domain and it remains unknown if the Protein A binding epitopes of any such targets are presented and available for binding on the cell membrane prior to product dissociation and full secretion from the cell. Thus, this method largely relies on labelling of the Fc-protein free of the cell, suspended in the semi-solid medium. The result is that the method cannot guarantee clonality of the lines picked. In addition, the conditions for the growth of cells in semi-solid media and the amount of fluorescent Protein A/G to be used may need to be established each time the method is used. The selection of cells from semi solid medium is also time consuming, as a period of time (normally at least seven days) is required to enable the cell to secrete sufficient quantities of product into the medium surrounding the cells to enable detection.

Moreover, the levels of target binding and thereby levels of fluorescence achievable are considerably reduced due to the lower avidity of Protein A, relative to higher avidity antiserum (such as a non-human anti-product antiserum). For these reasons Protein A is typically only employed as a secondary labelling reagent in conjunction with higher avidity primary reagents.

There is a desire in the art for improved cell selection methods.

SUMMARY OF THE INVENTION

The invention provides an improved method for the identification and selection of individual cell lines expressing high titres of a desired polypeptide (such as an antibody or antibody related product). The invention provides a new direct staining method which does not require the use of animal derived components, such as serum, at any stage and yet is as, or more, effective in identifying optimal high producing clones as when using animal derived anti-serums and standard protocols. Thus, the selected cell(s), which may go on to become the production cell line expressing a biopharmaceutical product for use in humans (and cell bank and manufacturing process thereof), is not unduly exposed to adventitious and transmissible agents. The invention overcomes the technical challenges of using FACS sorting protocols free of animal derived components to select for high producing clones through direct staining for product on the cell membrane. The invention also overcomes the need for use of semi-solid media and the time taken for extracellular 'halo' formation.

The invention also provides novel gating strategies based on the forward scatter (FSC) characteristics of the cells that enable better identification and subsequent isolation of high producing cell(s)/cell lines.

In addition the invention results in the identification of high producing clones from very early stages of cell line development, i.e. from as early as the 96-well stage, thus reducing the need to screen big number of clones. This results in significantly reduced effort for cell line generation. This is the first report that demonstrates the feasibility of identification of high producing cell lines from even the 96-well stage using a direct labelling FACS approach for single cell sorting.

In a first aspect, there is provided a method for selecting one or more cells expressing a polypeptide of interest, the method comprising the steps of: providing a population of cells, wherein the cell population comprises at least one cell expressing said polypeptide; contacting the cell population with a label which binds to said polypeptide on the surface of the cell; detecting the binding of said label to the polypeptide on the surface of said cell; and selecting said cell based on the presence of said label bound to the polypeptide on the surface of said cell; wherein the label is not a polyclonal antibody.

In another aspect, there is provided a method for selecting one or more cells expressing a polypeptide of interest, the method comprising the steps of: providing a population of cells, wherein the cell population comprises at least one cell expressing said polypeptide; contacting the cell population with a label which binds to said polypeptide on the surface of the cell; detecting the binding of said label to the polypeptide on the surface of said cell; and selecting said cell based on the presence of said label bound to the polypeptide on the surface of said cell; wherein the label is free from animal derived components.

In another aspect, there is provided a method for selecting a high expressing cell from a population of genetically engineered cells expressing a heterologous polypeptide, the method comprising the steps of: providing a population of cells expressing said heterologous polypeptide; detecting, for a specific cell within the population, the relative size of the cell; selecting the largest cell or cells from the population; and isolating said selected cell or cells from the population of cells.

In another aspect, there is provided a method of selecting a high expressing cell from a population of cells expressing a secreted heterologous polypeptide, the method comprising the steps of: providing a population of cells expressing said heterologous polypeptide; contacting the cell population with a label which binds to said polypeptide on the surface of the cell; detecting, for a specific cell within the population: the relative amount of said label bound to the polypeptide on the surface of said cell; the relative size of the cell; selecting at least one cell from the population on the basis of the relative amount of said label bound to the polypeptide on the surface of said cell and/or the relative size of the cell; and isolating said selected at least one cell from the population of cells.

The selection step may comprise selecting cells with higher mean FSC-A or higher FSC-W when compared to the mean FSC-A or FSC-W of the live cell population.

The use of a non-polyclonal antibody label enables cells with desired profiles to be selected without the use of animal derived components such as serum, or components derived from animals. In one embodiment, the label is not an antibody. In one embodiment of the invention, the label is recombinant Protein A, recombinant Protein G or recombinant Protein L. Thus, the label is not derived from animal sources, and has not been exposed to, for example, serum or other potentially adventitious agents of animal source. This reduces safety concerns and thus improves downstream processing of the polypeptide product, when that polypeptide is a protein intended for use as a biopharmaceutical.

The label may be conjugated to a marker to ease detection of the label bound to the surface of the cell. Suitable markers are fluorescent marker, a magnetic marker, or a biotin marker. Typically, the marker will be a fluorescent marker suitable for detection by a FACS device, such as FITC, RPE, DYLIGHT, ALEXA FLUOR, CYDYE, LI-COR, PE, Cy5, Cy7, PerCP and APC. For the avoidance of doubt, the conjugation of the marker may be direct (e.g. with a fluorescent Protein A) or indirect (e.g. with biotin, which can be bound by fluorescent streptavidin). Typical labels therefore include fluorescent Protein A, G or L.

The method may involve the detection of the relative amount of label bound to the surface of the cell, more specifically, the label bound to the polypeptide on the surface of the cell. As has been shown with anti-product antibody-based approaches to FACS (see Marder, P. ibid), the binding of the label to the polypeptide found on the surface of the cell provides an indication of the amount of polypeptide being expressed by that cell. Thus, the step of detecting the relative binding of the label to the surface of the cells, relative to other cells of the cell population, can provide an indication of which cells are likely to be high expressers of the polypeptide.

In an embodiment, the detecting step further comprises detecting the relative size of the cell. The present inventors have discovered that a subpopulation of cells (which may be mitotic cells) exists which are larger (more voluminous, as measured by FSC and/or SSC characteristics) in comparison to the other cells within the cell population. This subpopulation is distinct from the main population, when analysed by, for instance, forward scatter width (FSC-W) or forward scatter area (FSC-A). When cells from this subpopulation are cultured, the clones surprisingly express more of the polypeptide of interest than the cells of the main cell population, which are smaller in size (as measured by FSC and/or SSC characteristics). This observation is particularly surprising as these larger cells are a dynamic subpopulation which revert to the mean cell size over time. This large cell subpopulation is also referred to herein as the HFA cell subpopulation (and can be identified by FACS measurement of forward scatter characteristics, namely FSC-A and/or FSC-W), and the smaller ("normal") cell subpopulation as the LFA cell subpopulation.

In an embodiment, the selecting step comprises selecting the cell or cells from the population which show the highest amount of label bound thereto. The number of cells selected will depend on the number of cells ultimately intended to be cloned and/or cultured, and thus on the resources available. The person skilled in the art can define the selection criteria in order to select those cells which have the highest amount of label bound thereto. For example, if the label is a fluorescent label, then the skilled person can define selection criteria in order to select the cells which fluoresce most strongly. In a FACS protocol, the skilled person can readily define the gating criteria in order to select the most highly fluorescent cells. The most highly fluorescent cells are likely to be the most highly expressing cells in the cell population. In a typical embodiment, the highest-binding (e.g. most highly fluorescent) 20%, 15%, 10%, 9%, 8%, 7%, 6%, 5%, 4%, 3%, 2% or 1% or fewer cells within the cell population are selected.

In an embodiment, the selecting step comprises selecting the larger or largest or proliferating cell or cells from the population. The number of cells selected will depend on the number of cells ultimately intended to be cloned and/or cultured, and thus on the resources available. The skilled person in the art can define the selection criteria in order to select the larger or largest cells from within the cell population. For instance, in a FACS protocol, the skilled person can define the gating criteria in order to select the larger or largest cells. This could involve setting the gates of the FACS after analysing a sample of the cell population by means of an FSC-H/FSC-A plot, FSC-W/FSC-A plot, a FSC-W histogram or an FSC-A/SSC-A plot. The terms "larger" and "largest", as used herein, imply that the cell or cells are selected on the basis of their forward scatter characteristics, namely FSC-A or FSC-W. Larger or Largest cell or cells is any cell(s) within the subpopulation of live cells that has a higher mean FSC-A (as identified in an FSC-A/FSC-H plot or FSC-A/SSC-A plot) and a higher FSC-W (as identified in an FSC-A/FSC-W plot or FSC-W histogram) than the main live cell sub-population. Likewise, the term "highest", when used herein to describe the forward scatter characteristics of the cell, implies that the cells are selected on the basis of their FSC-A or FSC-W being higher than the mean FSC-A or FSC-W of the total live cells in the population. In a typical embodiment, the largest 20% or fewer, 15% or fewer, 10% or fewer, 9% or fewer, 8% or fewer, 7% or fewer, 6% or fewer, 5% or fewer, 4% or fewer, 3% or fewer, 2% or fewer or 1% or fewer of the cell population are selected.

It will be appreciated that there are a wide variety of suitable gating strategies, in addition to those described herein, which may be utilised to distinguish and select the same sub-populations as described herein. The skilled operator of the flow cytometer would be able to identify and gate the sub-population accordingly, based on the teachings of the present invention. Accordingly, such alternative gating strategies to select the HFA cell subpopulation (or a subset thereof) or the high fluorescing subpopulation (or a subset thereof) are also contemplated by the present invention.

In addition, different/additional labelling strategies that result in selecting and/or isolating the subpopulations (or subsets thereof) are also contemplated by the present invention.

The step of selecting will typically involve selecting only from the live cells from the population. Determining which cells within a population are live cells is within the normal capabilities of a person skilled in the art. For instance, in a FACS protocol, the skilled person can define the live gating of the cytometer accordingly. This will typically involve analysing a sample of the population of cells by way of an FSC-A/SSC-A plot. Further staining, e.g. with propidium iodide, may also be used.

The method may further comprise the step of isolating said selected cell or cells from the population of cells. Typically this involves the selection and isolation of individual cells from the cell population. The individual cells which have been selected may be deposited into discrete vessels, such as the wells of a 96 well plate. The vessel or vessels will usually contain a medium suitable for the clonal growth of the selected and isolated cell. Typically, the medium will be a serum free medium.

In an embodiment the medium is an animal derived component free medium.

It has been recognised that small numbers of cells struggle to grow in such conditions, due to the lack of cell-cell contact or essential factors released from a cell population. Accordingly, in an embodiment, the medium is a conditioned medium (the filtered supernatant from a culture of non-transfected cells), or may contain a mixture of conditioned and fresh media. In an alternative embodiment, the vessel contains feeder cells, which may be autologous in nature (i.e. from the same species, same tissue or same genetic origin). In an alternative embodiment the medium, fresh or conditioned, contains supplement(s) that support single cell growth, such as (optionally recombinant) albumin, transferrin or insulin growth factor.

In an embodiment, the label is fluorescent Protein A, Protein G, or Protein L, typically Protein A. The step of detection typically comprises determining the relative fluorescence of the label bound to the polypeptide on the surface of the cell, wherein a relatively higher fluorescence is indicative of a higher relative expression of said polypeptide. The selection step typically comprises, following the detection step, selecting the cell or cells from the population that have been detected in the detection step to have a relatively higher level of fluorescence in comparison to the cell population as a whole. The isolation step will typically comprise separating one or more of the selected cells from the cell population, and depositing each independently selected cell into a separate vessel, most commonly a well of a 96 well plate. In these conditions, the selected high expressing cell can be grown in clonal conditions.

The polypeptide may be any polypeptide which can be labelled with a non-polyclonal IgG or a non-antibody label. The polypeptide may be any suitable soluble (secreted) or membrane-bound polypeptide or multimeric polypeptide, including, for example, but not limited to an antibody, a hormone, an enzyme, a growth factor, a receptor, a fusion protein, an antigen, a biopharmaceutical or any other polypeptide, whether synthetic or natural. Typically, the polypeptide will be a therapeutic protein.

In an embodiment, the polypeptide is a secreted polypeptide. In an embodiment, the polypeptide comprises an immunoglobulin CH1, CH2 or CH3 domain, a CH2 and CH3 domain, or an immunoglobulin Fc domain (which may be a native Fc domain or a derivative thereof). Typically, the polypeptide is an antibody.

Typically the polypeptide will be a recombinant or heterologous polypeptide. To obtain a cell expressing a recombinant/heterologous polypeptide usually requires the transfection of a cell with a suitable expression vector encoding the gene to be expressed. The vector will usually contain a marker gene, such as a gene encoding for antibiotic resistance, to enable selection of the cells that express the polypeptide of interest. Alternatively the marker gene can be expressed from a second vector that is introduced into the cells at the same time as the vector encoding the polypeptide of interest. In a typical embodiment, the cell line will be a dhfr-cell line, and the expression vector or vectors transfected into the cell will contain DHFR and antibiotic resistance. However, other transfection method (or other methods such as transduction) and selection pressures will be suitable and may be chosen by the skilled person at will.

The population of cells may be any prokaryotic or eukaryotic cell type, not limited to mammalian cells, bacterial cells, yeast cells, plant cells, insect cells, avian cells, fish cells, or any derivative thereof, including an immortalised or transformed cell population based thereon. In an embodiment, the cells are mammalian cells, or immortalised or transformed cell mammalian cells. In an embodiment, the cells are selected from: CHO, CHO K1, CHO DG44, NSO, COS-1, COS-7, HEK293, HeLa, HK21, PerC6, 293T, Vero, AGE1.CR, HT1080, TE671, Namalwa or SP2/0. A typical cell line is a CHO cell line, or a cell line derived therefrom, including, but not limited to CHO K1, CHO K1 Chk2, CHO DG44, CHO DXB-11. The CHO cell line may be a dhfr-cell line, such as a CHO DG44 dhfr-line. Mammalian cell lines engineered for example to express modified sugar chains are also suitable for use in the present invention. Examples, of such cell lines include a CHO FUT8 knockout cell lines (e.g. U.S. Pat. No. 7,214,775, U.S. Pat. No. 6,946,292) or a cell line that has been engineered for upregulated expression of GnTIII (e.g. WO99/55342). In one embodiment, the cell population may be comprised of cells containing an artificial chromosome, such as the ACE system from CHROMOS (Lindenbaum et al, Nucleic Acids Research, 2004: 32(21)).

The population of cells may be cells from a bulk transfection, or may be established/clonal cell lines.

In an embodiment, the method of the invention will be a flow cytometry method, more typically, a fluorescent activated cell sorting (FACS) method. Typically, the step of detecting will be performed in a fluorescence activated cell sorter or analyser. Typically, the step of selecting will be performed in a fluorescence activated cell sorter or analyser. Typically, the step of isolating will be performed in a fluorescence activated cell sorter.

In an embodiment, the method further comprises the step of washing the cells, prior to the contacting step. Washing removes polypeptide which has been secreted by the cell into the surrounding medium, thereby ensuring that the label binds to the cell surface expressed polypeptide, increasing cell-specific staining. The step of washing the cells will typically comprise suspending the cells in a buffer such as but not limited to PBS, followed by centrifuging the cells to produce a cell pellet, and separating the cell pellet from the supernatant.

The invention also provides a method for selecting one or more cells expressing a polypeptide of interest by flow cytometry, comprising the step of staining the cell with a fluorescent binding label, wherein the method employs no animal derived components.

The invention also provides a method for selecting one or more cells expressing a polypeptide of interest by flow cytometry and with aid of a fluorescent binding label in which all components employed are derived from recombinant and non-animal sources.

According to the invention, a single selected cell can be grown or cultured in conditions which permit growth and division of that cell, thus producing a second population of cells derived therefrom (a clonal population). It is shown herein that the step of re-cloning single cells from a clonal population can increase the titre (i.e. the productivity) of cells. Thus, in an embodiment, the method comprises growing said selected cell in clonal conditions. This growing step may produce a further population of cells, herein referred to as a clonal population or a further cell population. The method may further comprise the step of selecting one or more cells from said further population of cells, and isolating said one or more cells from the further population of cells. This process may be repeated as many times as desired or necessary to produce a stable and/or higher producing cell line. In each case, the step of isolating cells from the further may be carried out according to the methods of the present invention, in order to select for high expressing cells.

Accordingly, in another aspect, the invention provides a method for cloning cells, comprising the steps of: isolating a cell from a population comprising a plurality of cells; and growing said isolated cell under clonal conditions to produce a clonal population.

In one embodiment, the growing step is carried out in conditioned medium. In an embodiment, the cell is a dhfr- cell transfected with a heterologous gene and a DHFR gene, and the step of growing is carried in a medium comprising methotrexate. In an embodiment, the cell is also transfected with a neomycin resistance gene, and the step of growing is carried out in a medium comprising G418. In this embodiment, the medium may further comprise methotrexate.

It has been found herein that the addition of recombinant serum albumin and/or recombinant transferrin in the medium increases the cloning efficiency (to the extent that the medium need not be a conditioned medium). Thus, the medium may further comprise recombinant serum albumin and/or recombinant transferrin. The concentration of serum albumin may be 0.1 to 10 mg/mL, more typically, 0.5 to 5 mg/mL, more typically still 0.75 to 2.5 mg/mL, most typically about 0.5-1 mg/mL. Transferrin concentration may vary as well but typically is in the mg/L range, most typically about 5 mg/L.

It has further been found herein that, following isolation of a single cell (single cell sorting), the subsequent viability and/or productivity of that cell line grown in clonal conditions can be improved by removing the selection pressure for a period of time. Accordingly, in an embodiment, the cell is a dhfr-cell transfected with a heterologous gene and a DHFR gene. In this embodiment, following the step of isolating the cell from the population, the isolated cell is grown for a first period in a medium, which may be a conditioned medium, which does not comprise methotrexate or an antibiotic, such as G418. The first period may be followed by a second period, in which methotrexate and G418 are added to the medium. Typically the first period will be between 12 to 100 hours, more typically 24, 26, 48, 64 or 72 hours.

Thus, in another aspect, the invention provides a method for cloning cells, comprising: isolating a cell expressing a heterologous protein; growing said isolated cell for a first growth phase in a medium in the absence of selection/amplification agent(s), eg methotrexate and/or an antibiotic, and in a second growth phase in a medium comprising the selection/amplification agent(s).

The method of the invention may further comprise the step of growing said selected cell in clonal conditions, to produce a master cell bank. The method may further comprise the step of growing said selected cell in clonal conditions, wherein the cells express said polypeptide; separating the polypeptide from the cells; and purifying said polypeptide.

The present invention also provides a cell selected by the method according to the invention, and a polypeptide produced by such a cell.

Other advantages will become apparent from the following detailed description, when read in conjunction with the Figures.

BRIEF DESCRIPTION OF THE FIGURES

FIG. 1: Cell line development flow diagrams and vector schematics. FIG. 1A Flow diagram of the conventional/standard cell line development protocol; FIG. 1B Flow diagram of the new, FACS based cell line development protocol FIG. 1C Vector schematics for Heavy and Light chain constructs. SCC: single cell cloning; SF: Shake flask; MTX: methotrexate; DHFR: dihydrofolate reductase; HC: Heavy chain; LC: Light chain)

FIG. 3: Cell sorting in the absence of staining for cell surface IgG expression—sub-cloning of existing cell lines.

FIG. 4: Detection of cell surface IgG expression on Live cell gated bulk transfected CHO cells using a FITC labelled anti-human rabbit polyclonal IgG. Fluorescence histograms for untransfected CHO cells or CHO cells transfected with plasmids encoding the antibody of project 10: FIG. 4A: Untransfected CHO DG44 cells FIG. 4B: Transfected cells after G418 selection FIG. 4C: Transfected cells after G418 selection and methotrexate amplification. Dotted line is unlabelled cells; solid line is anti-human IgG labelled cells.

FIG. 5: Optimisation of cell staining conditions for FACS analysis and sorting. Staining of parental CHO-DG44 cells and CHO-DG44 cells transfected with plasmids encoding the antibody of Project 10 with: Protein-A Alexa 647 (FIG. 5A), FITC labelled rabbit-anti-Human IgG (FIG. 5B) and DyLight649 labelled rabbit-anti-human-IgG (FIG. 5C). The left hand side column graphs show the mean fluorescence signal obtained for the different antibody/Protein A concentrations and the right hand side column graphs show the corresponding signal to noise ratio, i.e. the mean fluorescence of the transfected cells divided by the fluorescence of the DG44 parental cells at the same concentration. For all graphs the fluorescence of the Live gated cells is shown.

(FIG. 6): Comparison of IgG (DyLight649 conjugated) and Protein A (Alexa 647 conjugated) labelling of Control (untransfected cells), bulk transfected cells and a previously cloned line.

FIG. 8: Earlier recovery of FACS sorted clones and better response to feed in batch production when compared to clones derived from the conventional method (Project 13).

FIG. 9: FSC measurement and gating for HFA cells

FIG. 12: Statistical analysis for a panel of bulk populations and established cell lines. The data obtained for bulk populations (transfected, selected and 5 nM MTX amplified) (n=6) and established cell lines (n=19), either stained with DyLight649-IgG or Alexa647-ProteinA is analysed as follows:

FIG. 13: HFA Single cell sorting for an established line (Project 10) produces a stable sub-clone with increased batch production titre (parent titre was 1.6 g/L). Panel A shows the different cloning approaches taken and Panel B shows stability production titres at different passages for the best sub-clone (MTX8-B7) produced from the HFA sorting.

FIG. 14: Increased titre and enhanced stability of clones produced from FACS-based HFA single cell subcloning of a Project 3M cell line (BP0044). FIG. 14A shows the batch production titres of the parental line at different passage numbers; a dramatic decrease in titre is observed after passage 20. FIG. 14B shows batch production titres at different passages for an HFA sorted sub-clone (B2): titres are increased and the line is stable for at least 53 passages.

FIG. 15: Comparison of IgG titre in both static and shaking culture for cell clones sorted based on four different criteria—Project 3M sub-cloning (cell line BP0044). Sorting was performed after staining of the BP0044 cells with DyLight649 conjugated rabbit polyclonal anti human IgG.

FIG. 16: Generation of clonal cell lines for Project 10 by FACS using the HFA gating and IgG or Protein A staining/gating. CHO-DG44 cells were transfected with vectors encoding the antibody for Project 10 and were subsequently selected and amplified in bulk and then single cell sorted on the basis of four different criteria: (i) Live cell gating of rabbit anti-human IgG stained cells (FITC conjugated), (ii) top 5% fluorescence and HFA gating of rabbit-anti-human IgG stained cells (FITC conjugated), (iii) Live cell gating of Protein A stained cells (iv) top 5% fluorescence and HFA gating of Protein A stained cells.

FIG. 18: Re-cloning of established cell lines by FACS after either anti-IgG or Protein A staining. Batch production titres after sequential recloning are shown for all cases.

FIG. 19: Comparison of Clonepix derived (shown in grey bars) and FACS derived (shown in black bars) clones expressing 'protein X'. Clonepix and FACS derived clones were stained with PE-conjugated anti-'protein X' antibody and analysed by FACS. The mean fluorescence for each (MFI) is shown on the Y axis and is indicative of expression level.

FIG. 21: Generation of clonal cell lines for another Project (M). CHO-DG44 cells were transfected with vectors encoding the antibody for Project (M) and were elected and amplified in bulk. Subsequently the bulk population was stained with Protein A and single cell sorted. HFA or HFA-High Protein A gates were used. Results are shown as follows: Top panel: at 96-well titres of the top, 10th, 20th and 30th ranking clone are shown for HFA (un3stained) and HFA-High Protein A (HHA-High PrA). Bottom panel: Shake flask production/growth curves for the top 2 HFA (MU1 and MUS, dotted lines) and HFA-High Protein A (MS1 and MS2, solid lines).

FIGS. 22 & 23: Evaluation of the optimal FACS sort gating criteria following Protein A labelling and the use of a high FSC-A vs. SSC-A gate to define the HFA population.

FIG. 22 shows the gating schematic used for single cell sorting. To evaluate the optimal sort gating criteria based upon the % fluorescence following cell surface labelling with Alexa647-conjugated Protein A, live cells (FIG. 22A—P1 gate) were analysed for fluorescence intensity and gates to define the top 10%, 5%, 2% and 1% of protein-A stained cells were set (FIG. 22B). The HFA subpopulation of cells was gated using the FSC-A vs. FSC-H dotplot (FIG. 22C) and finally the top % gates from (FIG. 22B) copied to the fluorescence histogram from the HFA gate (FIG. 22D) and used for single cell sorting. To assess gating of HFA cells from within the FSC-A vs. SSC-A dotplot, cells exhibiting high FSC-A and high SSC-A characteristics were gated (FIG. 22A—P9 gate) and subsequently analysed for levels of Protein staining (FIG. 22E). The top 5% gate from the live population (FIG. 22B) was copied to the high FSC-A vs SSC-A histogram (FIG. 22E) and this gate was used for single cell sorting. FIG. 23 shows productivity from the single cell clones sorted upon the above criteria at the 96-well stage and in batch shake flask production curves.

FIG. 24: Protein G staining and comparison to Protein A. Parental, untransfected cells (top row), a bulk transfected/selected/amplified pool (middle row) and a clonal cell line (bottom row) were stained and analysed as shown. First column: FSC-SSC plot and live cell gate. Second column: Protein A staining of live cells. Third column: Protein G staining of Live cells, Fourth column: Protein G staining of HFA cells. Fifth column: HFA gate.

DETAILED DESCRIPTION OF THE INVENTION

Figure 2:
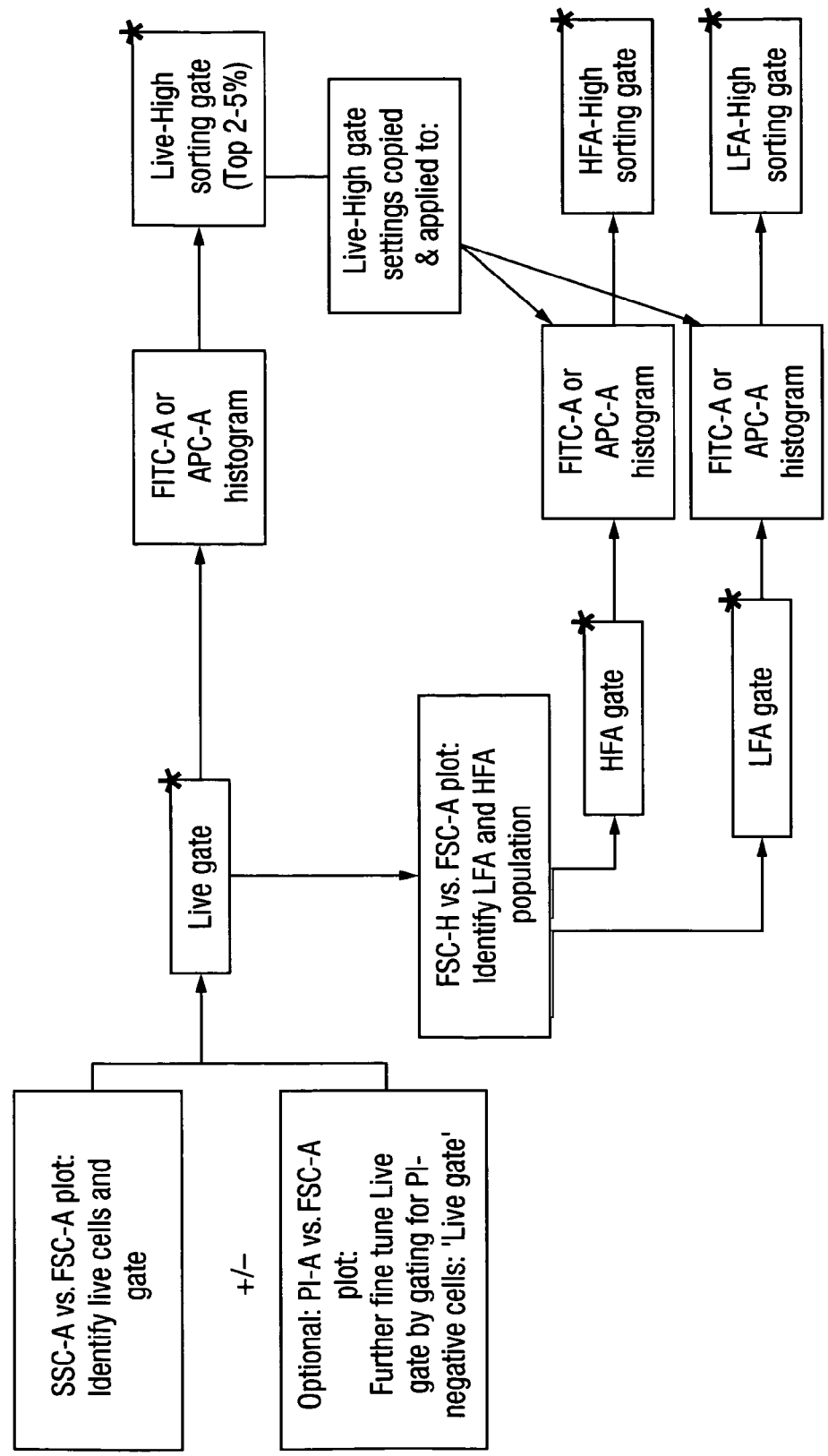
FIG. 2: FACS analysis and sorting gating logic as used in the examples. The flow diagram shows the sequence of gating. Asterisks indicate points where sorting can/has been performed. Starting from the left hand side of the figure, cells are initially selected based on their FSC-A vs. SSC-A properties to identify live cells. If necessary, propidium iodide may be used in addition for dead cell discrimination. When live cells have been gated 2 different streams can follow: On the top the fluorescence of this live cell population may be measured too (by staining with Protein A or IgG as described in the following examples), and a gate set for the highest fluorescing cells (Live-High gate, usually the top 2 to 5%). In parallel and on the bottom, the live cells may be further differentiated into high forward scatter area (HFA) and low forward scatter area (LFA) cells based on their FSC properties and as described in example 8. The fluorescence of either the HFA or LFA cells can also be measured and the Live-High fluorescence gate set for the live cell population applied, to identify and select for the HFA-High and LFA-High sub-populations respectively.

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc. which are incorporated herein by reference) and chemical methods.

The method employs non-animal derived non-antibody labels, such as recombinant Protein A, Protein G or Protein L, instead of animal derived anti-product antibodies for product-specific cell membrane staining. As all of the components utilised in method of the invention were produced without the use of animal derived materials such as serum or BSA, the risks of exposure of the final production cell line to adventitious and transmissible agents is significantly reduced.

A typical cell line generation protocol for CHO DG44 cells is outlined in FIG. 1A whereby cell lines are generated by low density plating of transfected cells. The vectors used herein are shown in FIG. 1C. After G418 selection and culture expansion a further step of low density plating is carried out with the addition of methotrexate for gene amplification. After culture expansion initial stability studies are carried out prior to single cell cloning, by limiting dilution or FACS sorting (without any surface staining) of the best clones. Similar protocols are followed for other CHO cell lines (with appropriate selection pressures. This process may typically involve plating and analysis of 100s or even 1000s of cells (e.g. see Wurm, 2004, ibid). Although this process can successfully produce cell lines suitable for the commercial manufacture of antibodies, we investigated the possibility that selecting cells stained for surface expression may lead to the selection of clones with higher IgG production. In addition to producing clonal lines we thought this process may decrease the time and numbers of clones screened required to identify higher secreting lines.

An improved protocol according to an embodiment of the invention is outlined in FIG. 1B, whereby selection (by G418 addition and nucleoside withdrawal) and methotrexate gene amplification are carried out on a bulk transfected population and such bulk transfected cell cultures are moved rapidly from static culture to shake flasks. The cells are then stained and the highest surface IgG expressing clones are single-cell-sorted from the bulk population. Alternatively, or in addition, the cells are also sorted based on their forward scatter (FSC) characteristics, whereby cells with higher mean FSC-A are selected/sorted. As well as isolating the highest expressing clones, this new method enables the isolation of the clones which subsequently produce high levels of IgG in batch production cultures. The method enables the identification of high expressing cells for further development from as early as the 96-well stage, resulting in the analysis of fewer than 100 clones and scale-up of fewer than 24 clones, and in many cases as few as 10 clones.

The examples which follow compare data produced by typical methodology using an animal derived protein labelling method (rabbit polyclonal anti-human IgG) to a new method completely free of animal derived proteins/components (labelling with recombinant Protein A). Additionally they demonstrate the advantages of selecting for/sorting cells with higher FSC-A characteristics.

Flow cytometry machines can detect several parameters such as Forward scatter (FSC), side scatter (SSC) and fluorescence (FL) with the maximum number of parameters depending upon the number of lasers and detectors the machine has available. FSC (forward scatter—also known as small angle forward scatter) is a measure of cell size and is defined as the scatter of light from the laser at small angles, typically 0.5-5°. A higher FSC correlates to a larger cell or event.

SSC (side scatter—also known as orthogonal scatter, 90° scatter, wide angle scatter or large angle scatter) is defined as the deflection of light from the laser between 15-150° and is associated with the granularity of the cells. Specific cells having selected characteristics can be selected by gating the data plots generated by the cytometer accordingly.

Figure 9A:
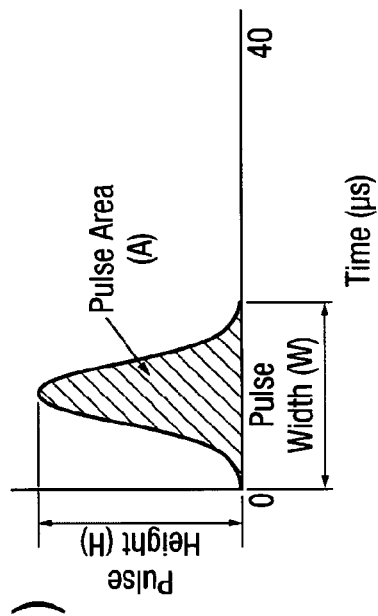
FIG. 9A> Histogram of Time vs. Voltage for the detection of the laser signal for FSC—height, width and area measurements shown.

Each parameter in flow cytometry is characterised by 3 values: the area (A) of the signal, which is the most widely used value, the height (H) of the signal and the width (W) of the signal. When the signal is plotted against time, its area, width and maximum height are determined as shown in FIG. 9A. For example for FSC there is FSC-A (also mentioned as FSC), FSC-H and FSC-W. For the purposes of the present application, when there is no -A, -H or -W next to a parameter's name, then it refers to the area value.

As used herein, the term HFA or (High Forward scatter Area) refers to the larger (more voluminous) cells (also known as "events") within the population. These cells have been investigated microscopically and consist of mainly larger single cells and not cell aggregates. They may be mitotic/proliferating cells. Selecting high expressing cells from this subpopulation is shown herein to result in an increased likelihood of selecting a cell with higher polypeptide productivity than selecting from the smaller cells in the population (or selecting simply on the basis of a high fluorescence/signal in a product specific direct stain). The exact size of these cells will, of course, vary depending on the cell type, growth conditions and so forth. The HFA or large cell subpopulation can be established for each specific population of cells by a person of skill in the art. Thus, the selection step herein may comprise identifying a discrete cell population (the HFA population) within the live cell population, gating on the FACS cytometer or analyser so as to select cells from this discrete population, and selecting cells from this discrete population. As mentioned above, there are various ways in which cells in this sub-population can be gated for and selected in a cytometer.

For any particular population of cells, the HFA cell subpopulation will be the live cells which have a higher than average FSC-W, or a higher than average FSC-A. As mentioned supra, the number of cells selected will depend on the number of cells ultimately intended to be cloned and cultured, and thus on the resources and time available. The skilled person in the art can define the selection criteria in order to select the largest cells from within the cell population.

Typically, however, the HFA subpopulation is the 20%, 19%, 18%, 17%, 16%, 15%, 14%, 13%, 12%, 11%, 10%, 9%, 8%, 7%, 6%, 5%, 4%, 3%, 2% or 1% or fewer of cells with the highest FSC-W values, within the live cell population.

The mean FSC-A of the HFA cell subpopulation will also be higher than the mean FSC-A of the total live cells in the population. Typically, the HFA subpopulation is the 20%, 19%, 18%, 17%, 16%, 15%, 14%, 13%, 12%, 11%, 10%, 9%, 8%, 7%, 6%, 5%, 4%, 3%, 2% or 1% or fewer of cells with the highest mean FSC-A value, within the live cell subpopulation.

The mean SSC-A may also be higher than average. The HFA sub-population may also contain high SSC-A cells.

Typically, the FSC-H of the HFA cell subpopulation will be substantially identical to the FSC-H of the total live cells in the population. In one embodiment, the mean FSC-H of the HFA cell subpopulation is approximately 100% (+/−) 10%, 5%, 4%, 3%, 2%, 1% or 0% of the FSC-H of the remainder of the cells in the live cell population.

In one embodiment, the HFA cell subpopulation will be the top 20%, 19%, 18%, 17%, 16%, 15%, 14%, 13%, 12%, 11%, 10%, 9%, 8%, 7%, 6%, 5%, 4%, 3%, 2% or 1% of cells in the live cell population having the highest FSC-W and highest mean FSC-A, and optionally having a substantially identical FSC-H to the mean of the population.

Figure 9B:
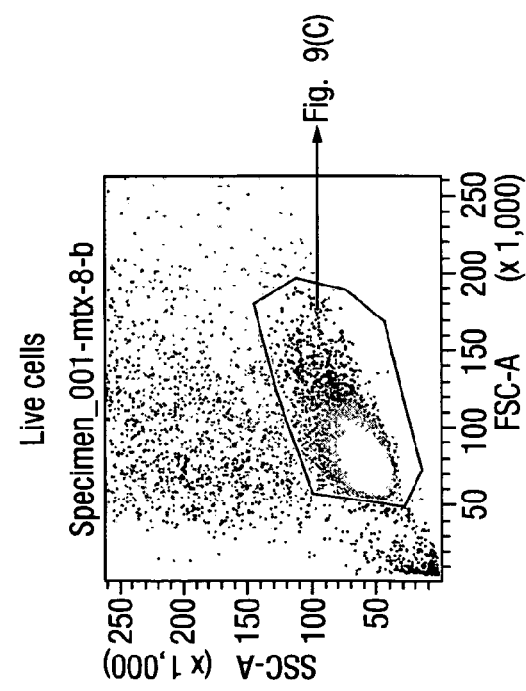
FIG. 9B> FSC-A/SSC-A plot showing the live cell gate for line MTX8 of Project 10. Note: for the majority of analyses/sorts a broader gate was used (e.g. see FIG. 6).
Figure 9C:
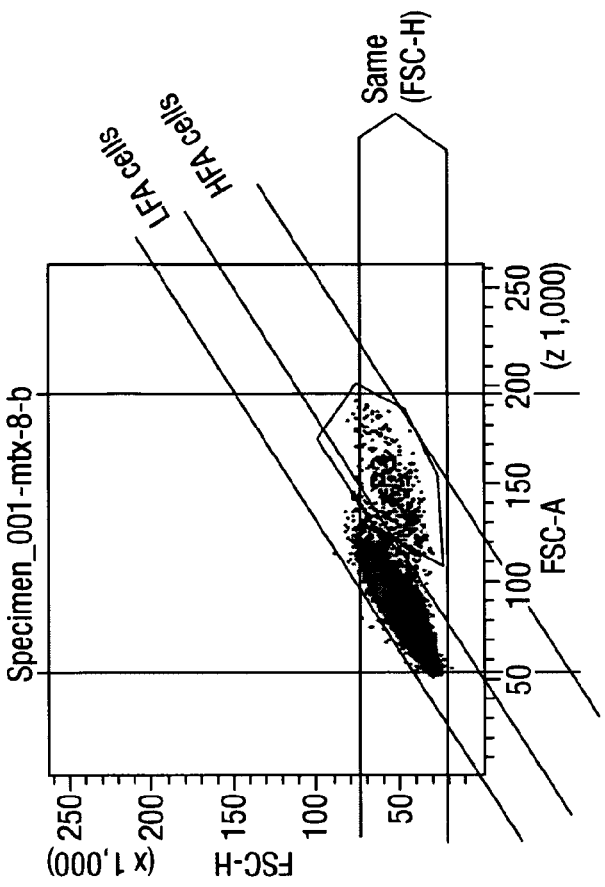
FIG. 9C> FSC-A/FSC-H plot derived from the live gate of B above, showing the high forward scatter area (HFA) cell and low forward scatter area (LFA) cell populations.
Figure 10A:
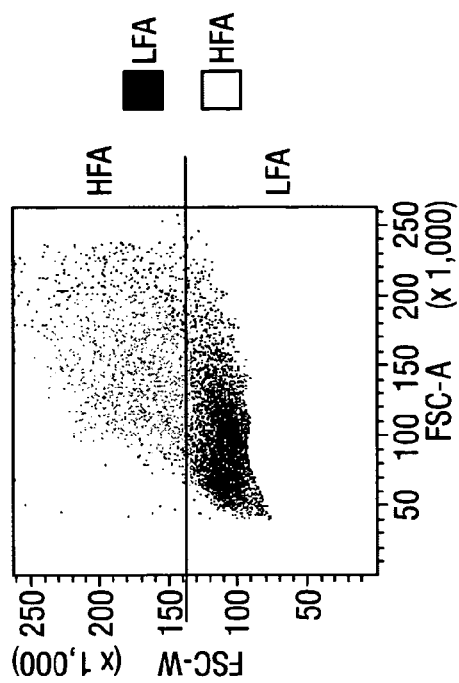
FIG. 10: Further flow cytometry plots comparing the FSC characteristics of HFA and LFA cells (representative data shown here were obtained with cell line #15, Project 12). Plots (FIG. 10A) and (FIG. 10B) show histogram of FSC-W or dot plot of FSC-W/FSC-A respectively for the LFA (dark grey) and HFA (light grey) populations—clear separation between the two populations is observed.
(FIG. 10C) A histogram plot for FSC-H, for both HFA and LFA populations: no difference between the two populations is observed.
(FIG. 10D) A histogram plot for FSC-A, again for both populations: partial overlap of the LFA and HFA cells is observed.

The live cell population can be determined and gated for by those skilled in the art, by way of a plot of FSC-A vs. SSC-A. Optionally, they can also be determined in an additional plot as the PI (Propidium Iodide) negative cells, upon staining with PI. The HFA subpopulation of the live cells can be determined and gated for by way of an FSC-H vs. FSC-A plot (FIG. 9C), an FSC-W histogram (FIG. 10A), an FSC-W vs. FSC-A plot (FIG. 10B), or optionally an FSC-A vs. SSC-A plot (FIG. 22).

In an embodiment, the mean FSC-A of the HFA subpopulation is 1.8 (+/−0.1) fold of the LFA subpopulation. In an embodiment, the mean FSC-H of the HFA subpopulation is 1.1 (+/−0.1) of the LFA subpopulation.

The term LFA (Low Forward scatter Area) in contrast, refers to the smaller (less voluminous) cells within the population. Consistent with the above, the skilled person can determine, for any given population of cells, the LFA cell population.

The "high" or "highest" expressing cells, as referred to herein, are those within the cell population which express the greater or greatest amount of the polypeptide of interest on the cell surface. Typically, such cells are selected for cloning as they are considered to be more likely to result in high titres of the polypeptide of interest when grown in large scale culture conditions.

The cells within the population may further be subdivided into HFA and LFA cells. In accordance with an embodiment of the invention, HFA cells are selected, as it has been observed that such cells also result in high titres of the polypeptide of interest when grown in culture conditions. In a further embodiment, high expressing HFA cells are selected.

The number (or percentage) of cells chosen as "high expressers" from a population will, of course, depend on the number of cells in the population as a whole, the range in polypeptide expression among the cells within that population and the number of cells to be sorted. Typically, the skilled person would select the highest expressing 5-20% of the cell population, optionally the highest expressing 15%, 10%, 5%, 4%, 3%, 2% or 1% of the cell population. In other words, the skilled person would select the approximately 20%, 15%, 10%, 5%, 4%, 3%, 2% or 1% or less than 1% of the cell population comprising the highest amount of the label bound to the polypeptide on the surface of the cells.

The term "relative", used herein in the context of "relative size" or "relative amount" (e.g. of label bound to the polypeptide on the surface of the cell), is intended to mean the value of the variable for a specific cell in comparison to the value of that variable estimated for the population of cells as a whole. Usually, a certain proportion of cells are analysed in the cytometer to enable the operator analyse chosen variables within the population, such as cell size or fluorescence, in order to define the appropriate gating values to select the chosen cell subpopulation, prior to the cell sort process. During the sort process, the cytometer determines the value of the variable (i.e. size or fluorescence) for a specific cell relative to the value of the variable for the cell population as a whole. Cells in FACS are defined as individual events recorded and displayed by the flow cytometer.

The term "antibody" is used herein in the broadest sense to refer to molecules with an immunoglobulin-like domain and includes monoclonal, recombinant, polyclonal, chimeric, humanised, bispecific and heteroconjugate antibodies; a single variable domain, a domain antibody, antigen binding fragments, immunologically effective fragments, single chain Fv, diabodies, Tandabs™, etc (for a summary of alternative "antibody" formats see Holliger and Hudson, Nature Biotechnology, 2005, Vol 23, No. 9, 1126-1136). Conversely, the term "non-antibody" to describe the labels used in the method of the invention implies the absence of any such molecule in the label. For the avoidance of doubt, Protein A, Protein G and Protein L are non-antibody (and therefore also non-polyclonal antibody) labels.

The phrase "single variable domain" refers to an antigen binding protein variable domain (for example, $V_H$, $V_{HH}$, $V_L$) that specifically binds an antigen or epitope independently of a different variable region or domain.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are considered to be "domain antibodies". As used herein $V_H$ includes camelid $V_{HH}$ domains.

As used herein the term "domain" refers to a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A domain can bind an antigen or epitope independently of a different variable region or domain.

A clonal population is a plurality of cells descended from a single common ancestor, for example a population of cells which have descended from a single original cell isolated from all other cells. Clonal conditions, as used herein, are conditions suitable to ensure that only one cell can be successfully expanded into a clonal population. Typically this is undertaken by placing only one cell in a single vessel or well in which the culture environment in that vessel or well is capable of supporting clonal expansion.

The below methods were used in the examples described subsequently:

Vectors Employed in this Study:

Standard mammalian expression and selection cassettes were employed in all aspects of this study in order to express biopharmaceutical antibodies and antibody related species and other proteins (that are able to bind Protein A, G or L) in mammalian cells (see FIG. 1C for a representative schematic of vectors). Standard oligonucleotide and gene synthesis, cloning, sub-cloning and sequencing methodologies were employed in design for such expression cassettes. During protein product ORF design, codon optimisation was carried out in accordance with the methods described by Kotsopoulou et al. (Kotsopoulou E et al J Biotechnol 2010; 146(4): 186-93 and WO2009/024567A1). Such codon optimisation, where respective ORF CAIS are >0.9, aids in ensuring expression is sufficiently high.

Expression Cassette Delivery to Cells:

There are many methodologies well known in the art suitable for the delivery of desired expression cassette or cassettes to desired cell hosts. Some require transfection whilst others employ other methods, such as viral vector transduction. Any such method may be employed for the purposes of the present invention. For the expression of antibodies and antibody related biopharmaceuticals described herein typically we employ plasmid based expression cassettes which are then transfected with the aid of lipids (e.g. lipofectamine, Invitrogen) or via electroporation (e.g. Gene Pulser II, Biorad) or most preferably by combinations thereof (e.g. Amaxa, Lonza). The Amaxa methodology has been found by the present inventors to ensure sufficiently high transfection rates to ensure rapid selection of stable polyclonal pools and suitably high expression for detection with the Protein A staining reagent, although electroporation has also been used with success in that respect.

Cell Hosts and Tissue Culture:

Any mammalian cell may be utilised for the purposes of the invention. Typically Chinese hamster ovary (CHO) cells are employed for the expression of biopharmaceutical protein products, as they have a long and proven track record in manufacturing biopharmaceuticals. There are many different variant CHO sub-strains but most typically CHO-DG44 or CHO-K1 hosts are utilised. Additional to CHO cells, other cells commonly employed to make biopharmaceuticals include bacterial cells, yeast cells, immortalized human cells (e.g. 293 cells or PerC6 cells), and immortalized non-human mammalian cells (e.g. NS0). Standard ADCF media was used for culture of such cells as described herein.

Transfection by Electroporation:

a. DNA preparation: Equal amounts (15 μg) of the heavy-chain and light-chain expression vector were linearised to completion (with Not I) in a 200 μl volume eppendorf reaction and then ethanol/sodium acetate precipitated. The pellet was then washed in 70% ethanol, air dried and re-suspended in 50 μl of molecular-biology grade water.

b. Preparation of CHO DG44 cells before transfection: $1.2 \times 10^7$ cells (per transfection) of healthy growing cells were spun (1000 rpm for 2-10 minutes) in a 15 or 50 ml tube, washed in 15 ml of ice-cold PBS/sucrose, spun again and then re-suspended in 800 μl of ice-cold PBS sucrose. This cell suspension was then added to the previously prepared DNA and left on ice for 15-minutes before being transferred to a chilled electroporation cuvette.

c. Electroporation: The cuvette containing the prepared DNA and cells was electroporated in a Gene Pulser set to 25 μF and 0.38 kV and then returned to ice for 10 minutes. The cells were then removed and added to 240-mls of non-selective media and then plated in non-selective media in 40×96-well dish at $2\text{-}5 \times 10^3$ cells per well (i.e. 50 μL per well). The plates were then and incubated at 37° C. and 5% $CO_2$ for 48 h.

d. Selection, amplification and clone identification: 48-hours after electroporation, 150 μL of selective media was added to each well. This selective media contains G418 and no nucleosides. Optionally, once a week thereafter, 140 μl of media was carefully exchanged for fresh selective media without disturbing the settled cell layer and after 3-4 weeks, all growing clones (typically growth of 0.1 colony per well; i.e. growth in 10 wells per 96-well plate) were titred for antibody production. The top ranking clones (typically 20-100) identified were then scaled-up in the same selective media through 24-well dishes and up to 6-well dishes. These clones were then plated at 1000 cells/per well in a 96-well dish (96-wells per clone) and then selected on selective media also containing 5 nM Methotrexate in a volume of 200 μl per well. After additional two to three weeks incubation, the best clones were again scaled up. A second and sometimes even a third round of amplification with 50 nM and 150 nM methotrexate followed to obtain high titre cell lines. In cases where the ORFs to be expressed were codon adapted (as described in Kotsopoulou E et al J Biotechnol 2010; 146(4): 186-93 and WO2009024567A1) a single round of amplification at 5 nM was sufficient. In order to evaluate final clones for production potential, the best clones at the final methotrexate amplification step were then scaled-up and evaluated in shake flask production models for titre and quality of the product generated.

Amaxa transfection: CHO DG44 (or CHO-K1) cells were passaged the day prior to transfection. The day of transfection the cells were counted by ViCell (Beckman-Coulter), pelleted by centrifugation at 1000 rpm for 5 minutes and the cell pellet was washed once in sterile PBS. The CHO cells were then resuspended at $10^7$ to $10^8$ cells/mL in Amaxa nucleofection buffer and then $10^6$ to $10^7$ cells were transfected in a sterile cuvette, with equal amounts of heavy and light chain plasmids, typically with 1-6 μg of light-chain plasmid and 1-6 μg of heavy-chain plasmid encoding the antibody of interest using the manufacturers recommended protocol for suspension CHO cells.

Bulk Selection and amplification: Immediately post-transfection several separate Amaxa transfections (up to 30 in total) were pooled in 1-3 pools and added to fresh medium and grown in a sterile T75 cm² tissue culture flask. For electroporations, a single electroporation (as described above) was used as a single pool of cells. Non selective media was used at this stage. 48-64 hours after transfection G418 containing and nucleoside free media was added for selection of transfectants. Subsequently the cultures were counted twice weekly and the volume was adjusted with medium addition/replacement as required, so that the viable count was kept at >0.5e6 cells/ml, where possible. As soon as possible—usually between 5 and 14 days post transfection; dependent upon the viable cell count—the cells were transferred to shake flasks and grown at 37 C, 5% $CO_2$ shaking at 130-150 rpm. After recovery to >70% cell viability—usually 2.5-4 weeks post transfection—methotrexate was added to the culture medium to a final concentration of 5 nM. At this stage continuation of G418 in the media is optional. After exposure to methotrexate for a period of between 10 to 25 days the cells were analysed for surface antibody expression and were subsequently single cell sorted using a FACS Aria I (Becton Dickinson).

Preparation of Fluorescent Reagents (IgG and Protein A) for Use in FACS:

DyLight649-IgG: Affinity purified polyclonal anti-IgG raised in rabbit (Rockland, Cat no #609-4102) was labelled using a commercially available kit—DyLight649 Thermo Cat #53050 as follows: The antibody, in 50 mM sodium borate buffer, pH 8.5 was added to the DyLight649 vial for labelling and mixed gently by inversion, ten times. The sample was incubated at room temperature in the dark for 60 minutes prior to passing down a filter column to remove unbound dye. Labelled sample was collected, the IgG concentration measured, and the sample aliquoted for storage at −20° C.

FITC-IgG: Affinity purified fluorescein (FITC) conjugated polyclonal anti-IgG raised in rabbit was purchased from Rockland (Cat no #609-4202)

Alexa647-Protein A: was purchased from Invitrogen (cat no P21462). Protein A was reconstituted from lyophilised protein in sterile PBS to 1 mg/mL and aliquoted aseptically before freezing at −20° C. until use. On the day of use the frozen aliquot was defrosted immediately prior to staining and diluted further to a 0.1 mg/mL working stock with additional sterile PBS, before adding to the appropriate amount to the cells to be stained.

Alternatively, and where specifically stated in the examples below (as Repligen Protein A), protein A was purchased from Repligen and was labelled using an AlexaFluor647 labelling kit from Invitrogen (cat no A20173), as per manufacturer's instructions.

Although fluorescently labelled reagents were used as described above, one could also use indirect labelling. For example biotinylated reagents can be use with fluorochrome conjugated avidin or streptavidin as secondary reagents for FACS analysis/sorting.

Cell Staining Protocol:

a. Staining with FITC or DyLight649 conjugated anti-IgG: Cells to be stained were passed through a sterile nylon 40 μm sieve prior to counting to remove clumps of cells that could block the FACS stream. After counting cells were washed once or twice in sterile PBS prior to incubating with fluorescently labelled anti-product IgG. Washing removes secreted, non-cell bound IgG product, which may reduce the fluorescent signal. Washing was carried out by pipetting the correct volume of cells for $10^6$ cells/tube into each FACS tube and then adding PBS to the cells and centrifuging the cells at 1000 rpm for 5 minutes. Anti-human IgG antibody was added directly to the cell pellet after decanting the final wash supernatant and incubated on ice for 20 minutes in the dark. Optimal staining of cells with these proteins was achieved with 5-10 μg anti human IgG/$10^6$ cells (see FIG. 5) and a very good signal to noise ratio was obtained. After staining, one to two washes were carried out in PBS or cell growth medium before resuspending the cell pellet in growth medium and storing the tubes on ice in the dark until ready to analyse and/or sort.

b. Staining with Alexa647 Protein A: Cells to be stained were passed through a sterile nylon 40 μm sieve prior to counting to remove clumps of cells that could block the FACS stream. After counting cells were washed once or twice in sterile PBS prior to incubating with fluorescently labelled Protein A. Washing removes secreted, non-cell bound IgG product, which may reduce the fluorescent signal. Washing was carried out by pipetting the correct volume of cells for $10^6$ cells/tube into each FACS tube and then adding PBS to the cells and centrifuging the cells at 1000 rpm for 5 minutes. Protein A was added directly to the cell pellet after decanting the second wash supernatant and incubated on ice for at least 20 minutes in the dark. A much lower signal than that achieved with the IgG reagent was obtained. In addition a higher background staining was observed, and as a result the signal to noise ratio was lower than that for the IgG. However, optimal staining of cells was achieved when 0.25-1 μg Protein A/$10^6$ cells was used (see FIG. 5). After staining, two washes were carried out in PBS or cell growth medium before resuspending the cell pellet in 600 ul growth medium/tube and storing the tubes on ice in the dark until ready to analyse and/or sort.

Sorting Protocol:

Flow Cytometry: For all FACS based sorting we employed a FACS Aria (Becton Dickinson, Oxford, U.K.) which had undergone a sterilising cycle using 70% ethanol to ensure sterility of the clones post sort. After flushing the instrument with sterile PBS to remove residual ethanol, the drop delay was set using Becton Dickinson Accudrop beads and Diva software v5.0.3 to optimise the machine for sorting. Prior to FACS sorting, unstained and/or stained polyclonal pools of cells or established cell lines were sieved through a sterile nylon 40 micron mesh to remove large clumps of cells that would block the stream. Unstained and stained parental (untransfected) CHO cells were used to set the detection voltages and also for accurate gating as described in the following section.

FACS Aria setup: samples were sorted using a 100 μm nozzle on a low setting for single cell sorting and low sheath fluid pressure. Laser light passed through a 1.5 neutral density filter to get the best resolution of the CHO cells in the FSC- vs. SSC plot. Signal from the 488 nm blue laser was detected with a 530/30 or a 575/25 band pass filter for FITC and PI respectively. Fluorescence from APC was captured after excitation from the red diode 633 nm laser with a 660/20 band pass filter. The stably transfected (either selected or selected and amplified) cells to be sorted were analysed by reading and recording the sample data and the gates for sorting optimised on saved data. Samples to be sorted were kept on ice in the dark until required for sorting to minimise internalisation of staining Protein And any degradation of the fluorescence signal. Capture plates were setup on the day of the sort and kept at 37° C., 5% $CO_2$, with a high humidity until required. The FACS Aria machine was optimised to deliver to the centre of each well of the 96-well capture plate. Sorted plates were returned to the incubator immediately after the plate had finished sorting, typically within one minute.

Sort Gating Strategy to Identify and Isolate the Desired Cell Populations of this Invention:

FIG. 2 provides a flow diagram of the gating strategy decisions as made in the examples that follow.

Figure 11:
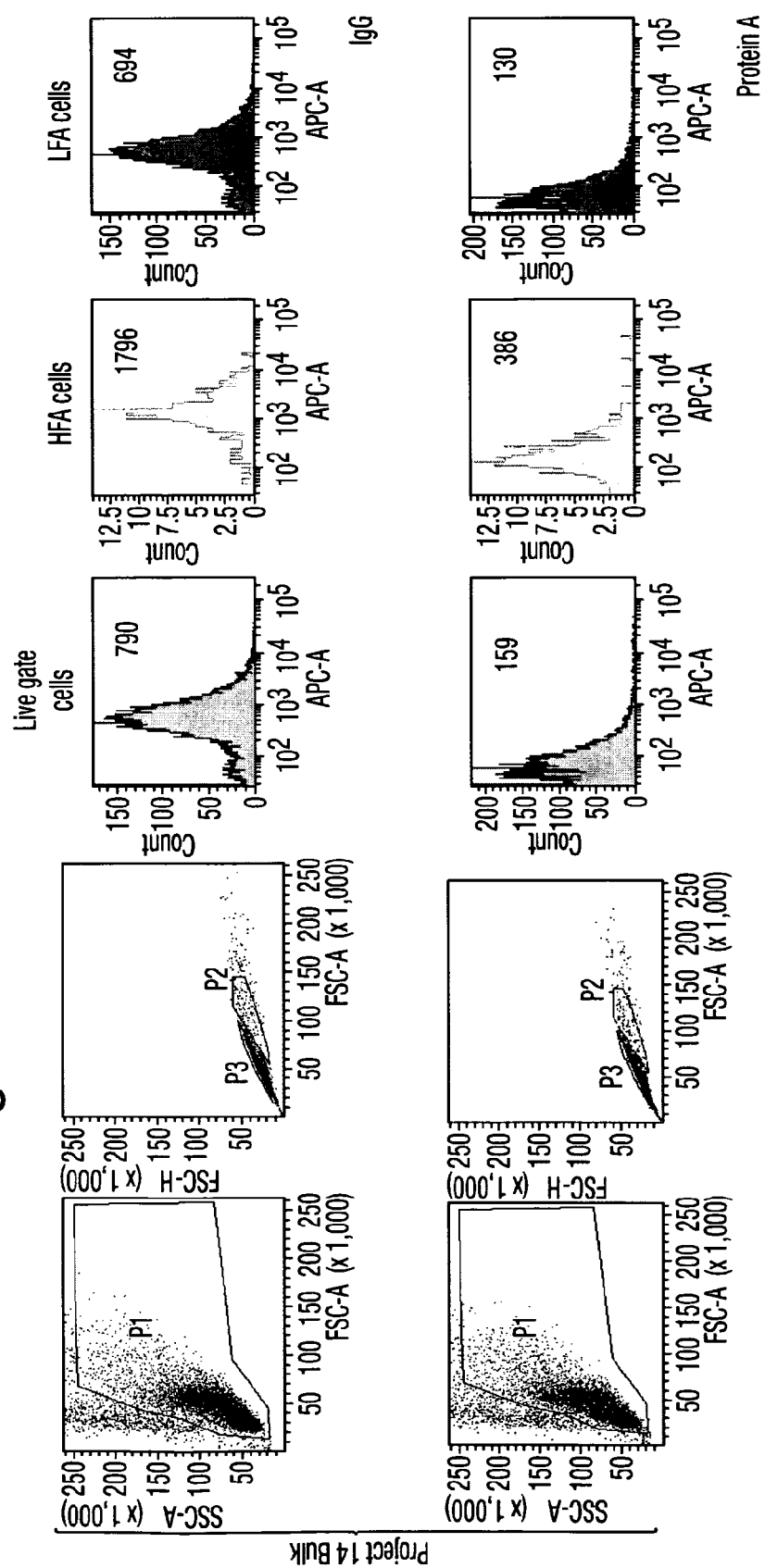
FIG. 11: Comparison of IgG(DyLight649 conjugated) versus Protein A(Alexa647 conjugated) labelling for bulk transfected cells (Project 14) and a previously cloned line (Project 12, line #84). From left to right: Live cell gate (FSC/SSC plot), HFA and LFA gate (FSC-H/FSC-A plot), fluorescence histogram of live cells with mean fluorescence value shown, fluorescence histogram of HFA cells with mean fluorescence value shown and fluorescence histogram of LFA cells with mean fluorescence value shown. From top to bottom: Bulk population stained with rabbit-anti-human-IgG, Bulk population stained with Protein A, clonal cell line stained with rabbit-anti-human-IgG, clonal cell line stained with Protein A.
Figure 11:
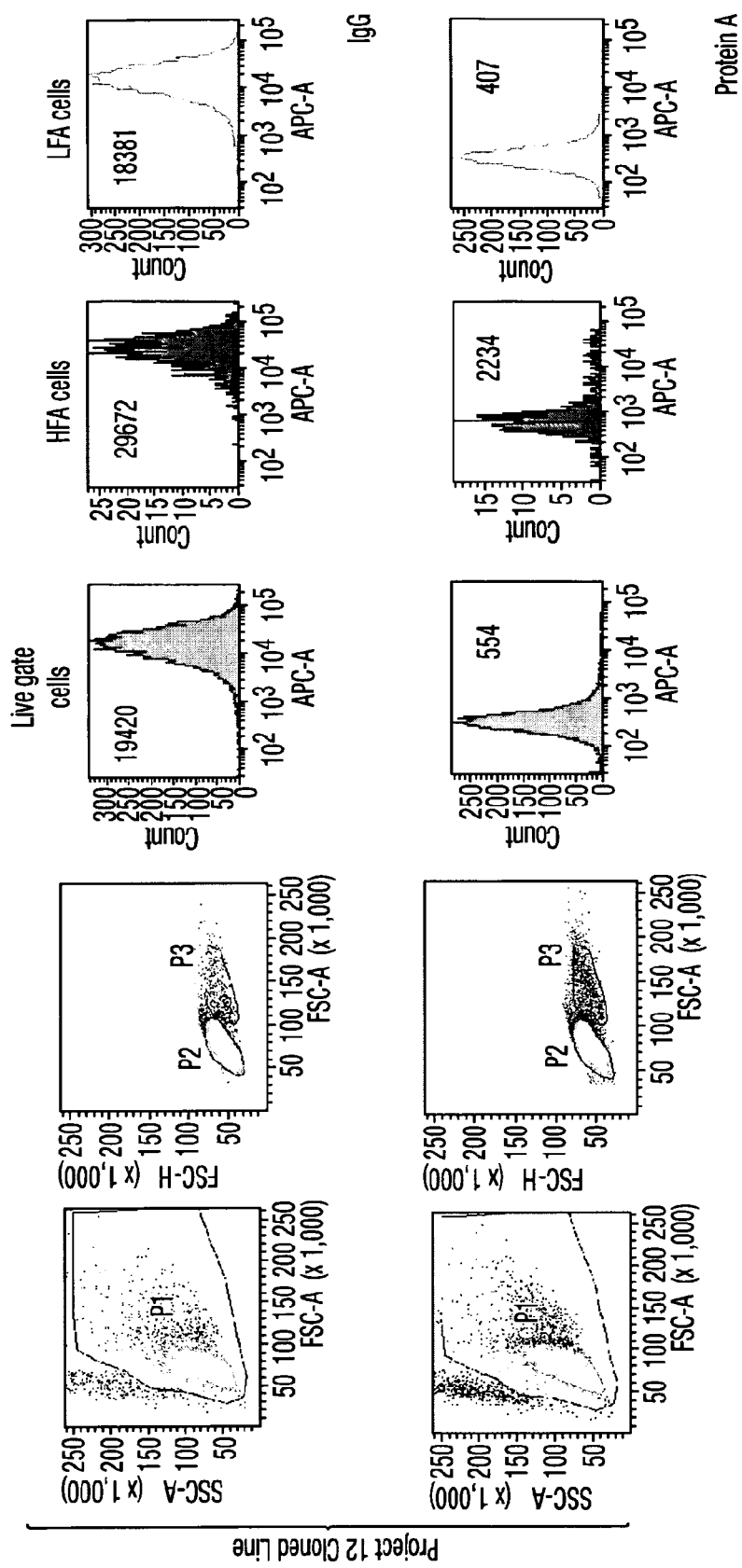

Gates were set using appropriate unstained or stained control cells (untransfected CHO-DG44 cells and/or unstained samples). Samples were recorded and firstly the live cell gate was established. Propidium iodide staining (7 ul/tube of 50 ug/mL PI stock purchased from Becton Dickinson) of the cells was also carried out in some cases to distinguish between the live and dead cell populations. However, FSC-SSC gating was found to be sufficient to distinguish between live and dead cells, so PI staining was not done in the majority of cases. A further dot plot of FSC-A vs. FSC-H was set up for some experiments and a gate was drawn to select for the HFA sub-population, as described in Example 8. Then FITC-A or APC-A histograms were set-up for the live gated cells and in some cases for the HFA and LFA cells. The sorting gate was set in most cases to between the top 5% or 2% fluorescing 'Live' cells and this gate was copied, when required, onto the FITC-A or APC-A histograms of the LFA and HFA cells. FIG. 11 shows some exemplified sort plots. FSC-SSC gating is also suitable for selecting the HFA subpopulation, as shown in Example 14 and FIG. 22.

IgG Titre Analysis:

Two methods, described below, were used for 96-well and some 6-well titre analysis:
  a. IGEN: for media samples obtained from 96-well plates, antibody titre was determined by automated 96-well sandwich ELISA style methodology on an IGEN M-Series M8/384 analyser (Bioveris, Maryland, USA) with manufacturer's recommendations and standard methodologies. The sandwich consisted of Streptavidin coated magnetic coated beads, Biotinylated-Protein A and Ruthenium labelled F(ab)2 fragments. The signal generated for the test sample was then compared to a serial dilution of the antibody reference standard. Whilst a highly sensitive assay, due to assay variation combined with cell growth variables at 96-well cultures, assay intermediate precision and reproducibility is relatively low for this assay for high-yielding, amplified cell lines.
  b. MSD ELISA method: soluble IgG measurement was carried out by MSD assay (Mesoscale Discovery, U.S.A.) using Protein A coated ELISA plates. Assays were carried out in accordance with the manufacturer's instructions. Briefly plates were first blocked to reduce non-specific binding with proprietary blocking agent (3% of Blocker A) for 60 minutes at room temperature. Plates were then washed with three successive washes with 150 ul/well of PBS containing 0.05% Tween-20, blotting onto paper towels in between washes. IgG control standards were prepared and plated out at 25 ul/well at the following concentrations: 5, 4, 3, 2, 1, 0.5, 0.25, 0.125, 0.0625, 0.031, 0.015 & 0 mg/L. Samples to be tested were also added 25 ul/well. Tag-IgG detection antibody was diluted to 0.255 ug/mL in antibody diluent and added 75 ul/well. The plates were shaken at 750 rpm for 60 minutes at ambient temperature. Three more washes were carried out as before and 150 ul/well of 1× read buffer added and the plate read on an MSD1200 plate reader. IgG titres for the unknown samples were back calculated from the standard curve using the MSD plate reader software.
  c. For media samples obtained during shake flask and bioreactor production modelling, antibody titre was measured with the aid of a nephelometric method where a light signal is scattered by the insoluble immune-precipitin in the reaction solution using a Beckman Coulter Image system (Buckinghamshire, England) and manufacturer's recommendations and standard methodologies. The signal generated for the test sample again being compared to a serial dilution of the antibody reference standard.

Bioreactor Shake Flask Production Models (Extended Batch Production Models), Also Referred to as Growth Curves:

typically cells were seeded at 200,000-800,000 cells per ml in animal-derived-component-free media in either standard 250 ml tissue-culture shake-flasks with vented lids in a volume of 120 ml or in standard 125 ml tissue-culture shake-flasks with vented lids in a volume of 60 ml. They were then incubated with agitation in carbon dioxide enriched air and set temperatures to encourage and sustain cell growth. Various conditions were tested for each clone—for example at various temperature conditions. In the results reported herein the highest titre for each clone (across standard conditions) tested is exemplified. Typically the production model end point titres as reported herein were recorded at the point at which cell viability drops to approximately 50% as determined by trypan blue exclusion based assay on a Vi-Cell (Beckman) using standard Vi-Cell CHO parameter settings and manufacturer's recommended protocol. Typically this end-point titre is generated after 10-20 days incubation.

Miniature Production (Duetz) Models (Extended Batch Production Models):

As for the bioreactor model above. Typically cells were seeded at 800,000 cells per ml in animal-derived-component-free media in 24-well plates and a final volume of 1.5 mL.

Cell Line Stability Evaluation:

Cell lines were cultured for up to 50 passages in their relevant growth media and batch production curves were set up every approximately 10 passages as described in the previous paragraph to assess drifts in productivity.

Clone Growth and Selection after Single Cell Cloning:

Various methods exist in the literature for the cloning of mammalian cells (e.g. see Brezinsky 2003, ibid or Hügin 1997, J Immunol Methods, 205, 211-212). Such methods are suitable for use in this invention. Additional novel methodology for cloning mammalian cells is described below and has been used herein. The following methods/conditions have been used for the purposes of this invention and are only used as examples.

Single cells were deposited in individual wells in 96-well plates, either by serial dilution or FACS sorting, as described in the examples. The plates already contained 100-200 μl/well of either 25-50% cell free conditioned medium, unconditioned medium, or medium containing feeder cells. Conditioned medium was produced by mixing fresh cell growth medium with harvested, centrifuged and 0.2 μm filtered medium from a 3-4 day old culture of growing parental untransfected cells. Unconditioned medium was fresh medium of the same composition as the medium that the cells were growing in prior to cloning, with or without the addition of supplements, such as Transferrin or recombinant albumin, as described in the examples. Where used, feeder cells were untransfected parental CHO cells, that were usually deposited at 500-2500 cells/well 0-24 hours prior to cloning. Selection and amplification agents, G418 at 400-1000 μg/ml and methotrexate at 5 nM final concentrations in the examples below, were added 0-64 hours after the deposition of the single cells and were maintained in the medium thereafter. Optionally, once a week after the deposition of the single cells in the 96-well plates, 140 μl of media was carefully exchanged for fresh media without disturbing the settled cell layer and after 2-4 weeks, all growing clones were scaled up to 24-wells. In some cases clones were picked randomly (mainly for established lines) and in other cases up to 300 were titred at 96-wells for antibody production and only a fraction, typically 20-100, were scaled up to 24-wells. The evaluation of the clones then followed the usual cell line development protocol for scale up and productivity assessment.

Example 1

Cell Sorting in the Absence of Staining for Cell Surface IgG Expression—Sub-Cloning of Existing Cell Lines Initial FACS sorting was carried out on established cell lines expressing monoclonal antibodies, solely on gating for live cells, based on (SCC/FSC)+/−(P1/FSC) plots (Projects 5d, 7b, 10). A standard single cell sorting protocol was used to clone the cells and the results in FIG. 3($a$) show the ability to clone out higher secretors in the absence of any anti-IgG cell surface staining. The data shows a doubling of titre for Project 5d, a 1.5 fold increase for Project 10 and a 3.5 fold increase in titre after 2 consecutive sorts for Project 7b. Project 6d was cloned by limiting dilution.

Figure 3A:
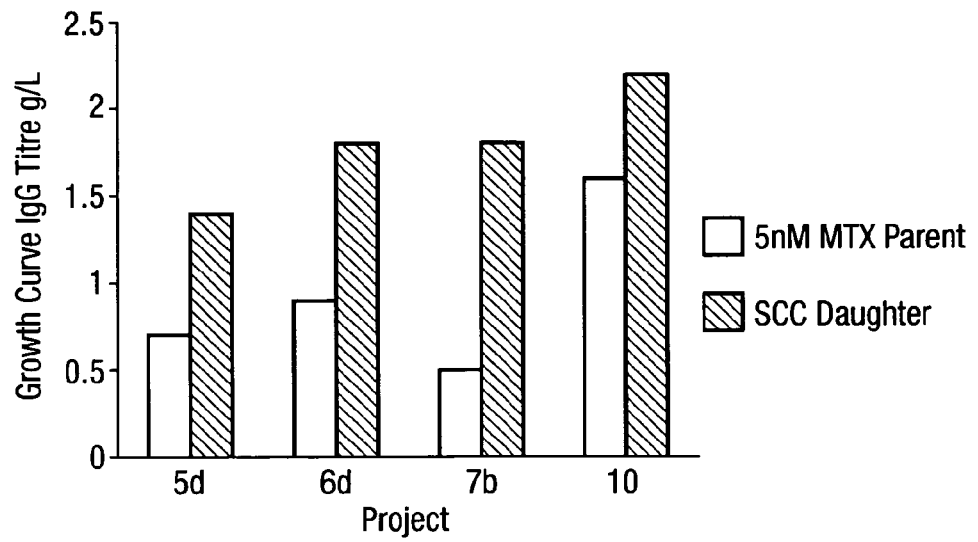
FIG. 3A. Batch production model of parental and sub-cloned daughter cell lines for a variety of projects. Cell lines were single cell cloned by FACS using only the Live cell gate (Projects 5d, 7b &10) or by limiting dilution (Project 6d). In the case of 7b two rounds of cloning by FACS were performed. The data show significantly increased titres after cloning.
Figure 3B:
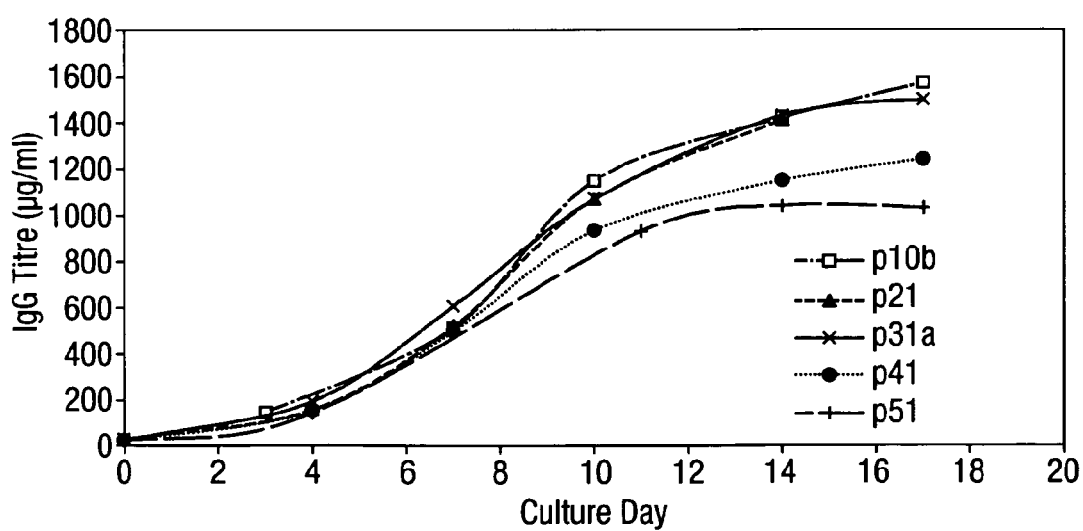
FIG. 3B. Batch production models at different passages (p10, 21, 31, 41 and 51) for a single cell sorted clone (Project 7b, line 84-8#158-202), demonstrate cell line stability.

In addition to enabling selection of potentially higher secretors, the single cell sorting also lead to the derivation of lines with good stability over 50 passages as shown in FIG. 3($b$) for Project 7b. With encouraging data produced from these FACS studies, subsequent studies progressed to staining for surface IgG in an attempt to focus on and clone out the highest secretors from stably transfected populations and/or established cell lines.

Example 2

Bulk Transfection/Selection/Amplification and Detection of Expression Levels by Staining for Cell Surface IgG Expression State of the art direct staining FACS sorting protocol for the identification and sorting of high producing cell lines expressing biopharmaceuticals such as antibodies employ animal derived components. A typical protocol is described below.

An affinity purified anti-Human IgG (H+L) in buffer containing bovine serum albumin (Rockland, Gilbertsville, Pa. 19525 USA) was employed. This antibody was originally raised as a rabbit antiserum and was purified by immunoaffinity chromatography using human IgG coupled to agarose beads before final formulation in buffer containing bovine serum albumin. The antibody was conjugated to FITC or DyLight649.

CHO DG44 cells were transfected with plasmids encoding the light and heavy chain of Project 10 using the Amaxa transfection regime, as described in the methods section above. Transfected cells were selected and amplified in bulk. FIG. 4 shows fluorescence levels achieved after antibody staining untransfected cells (FIG. 4A) and transfected cells after G418 selection (FIG. 4B) and after both selection and methotrexate (5 nM) amplification (FIG. 4C). This figure demonstrates that cell surface IgG expression is detectable above background levels with this method. In fact, even before amplification the 'shift' in fluorescence is enough to separate transfected from untransfected cells.

Example 3

Protein A Vs. Anti-Sera Staining

We next compared surface staining using both Protein A and anti-human IgG (polyclonal). We observed Protein A staining produced a reduced signal and a lower signal to noise ratio. Given the reduced avidity of Protein A versus standard IgG staining reagents this was to be expected. However, we attempted to optimise the staining protocol. For this purpose an established cell line (Project 10) was used to define the optimal amount of Protein A to be used. The cells were washed twice prior to staining, to remove soluble secreted antibody away from the transfected cells, and then stained with varying amounts of either antibody or Protein A, staining samples of $10^6$ cells before washing off excess antibody/Protein A with two further washes and were kept on ice until cytometry was carried out. Fluorescence levels detected using this staining regime are shown in FIG. 5. The optimum amount for staining was calculated to be 5-10 μg/$10^6$ cells for the anti-human IgG or 0.25-1 μg/$10^6$ cells for Protein A—staining was performed in all cases for 20 minutes on ice, in the dark.

Even after optimisation, the data in FIG. 5 indicate that Protein A gives a lower level of fluorescence than the polyclonal anti-IgG antibody. One explanation for this is the likelihood that there are a higher number of epitopes recognised by the antibody, due to its polyclonal nature.

Figure 6A:
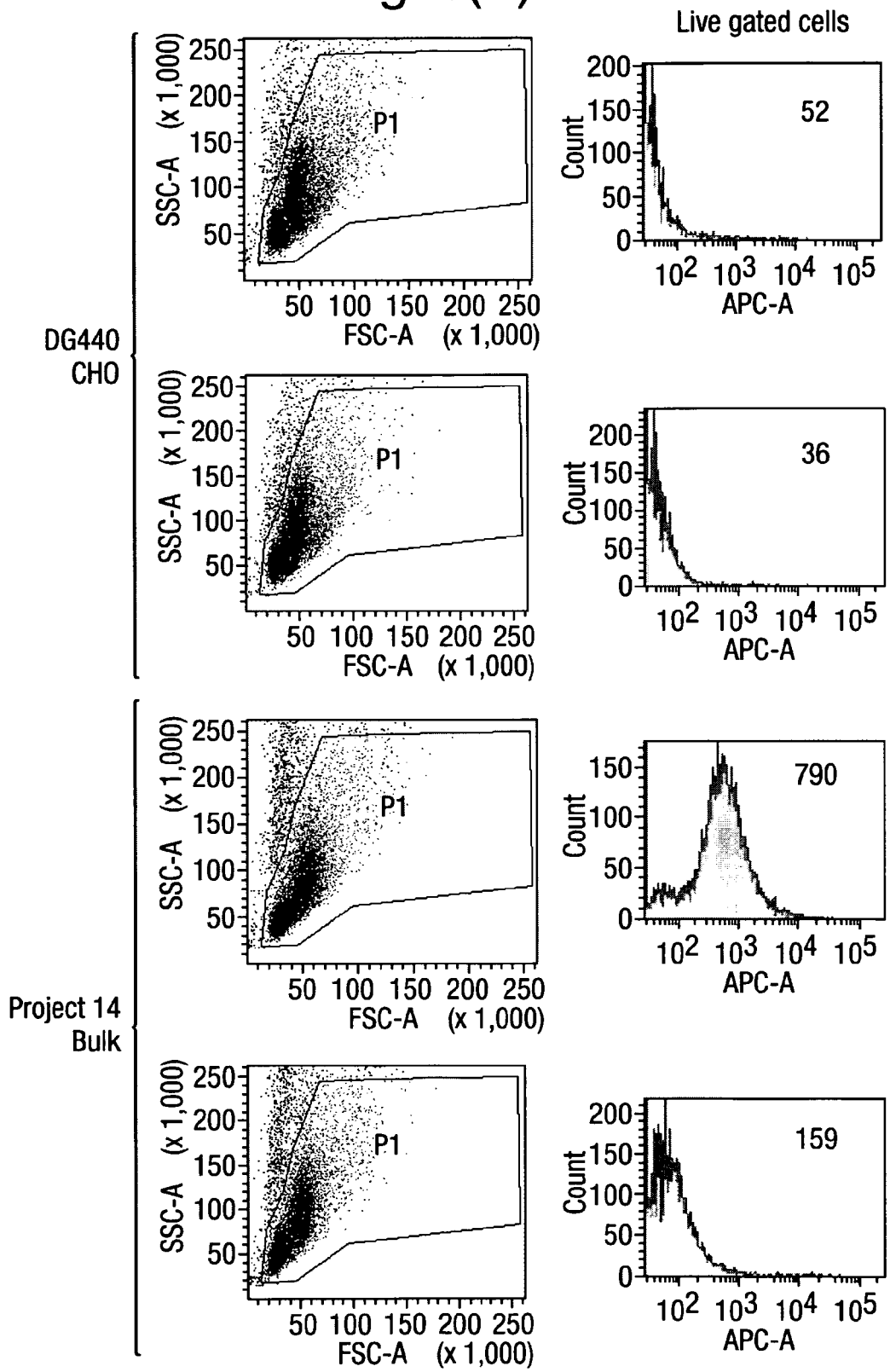
FIG. 6A Comparison of parental non-transfected CHO DG44 cells with bulk transfected (following G418 selection and methotrexate amplification t) Project 14 cells. Analysis following both IgG (top panels) and Protein A (bottom panels) staining is shown. The left column shows the Live cell gate (FSC-SSC plot) and the right column shows the fluorescence histogram of the live stained cells. Numbers indicate the mean fluorescence intensity of the live cell population.
Figure 6B:
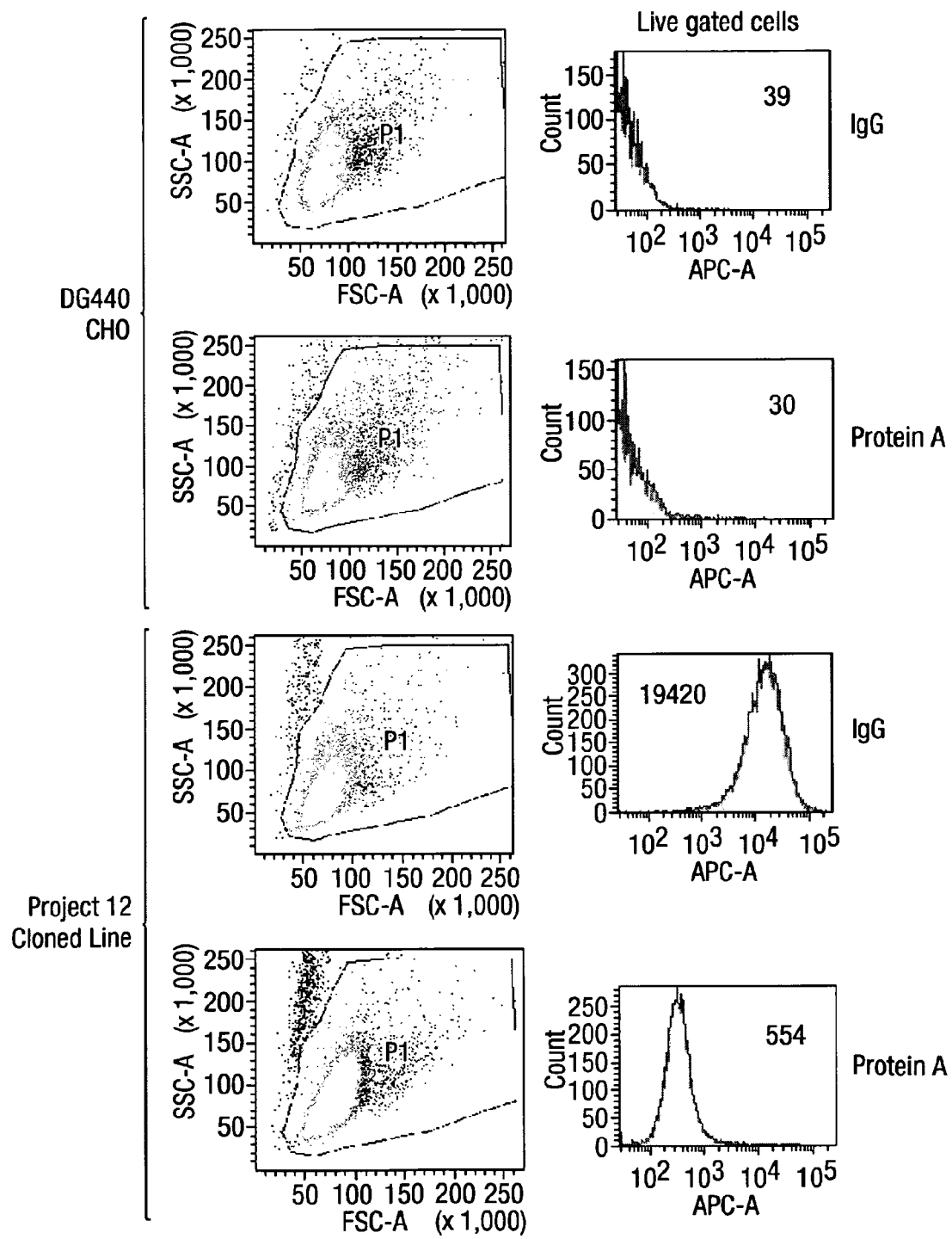
FIG. 6B Comparison of parental non-transfected CHO DG44 cells with a previously sub-cloned cell line (cell line 84, Project 12). Both IgG (top panels) and Protein A (bottom panels) shown. The left column shows the Live cell gate (FSC-SSC plot) and the right column shows the fluorescence histogram of the live stained cells. Numbers indicate the mean fluorescence intensity of the live cell population.

Subsequently the signal generated by IgG vs. Protein A staining was analysed for both established lines and bulk transfections. Example results for Projects 12 and 14, respectively, are shown in FIG. 6. These indicate that Protein A staining is readily visible on established lines. Surprisingly, although bulk heterogeneous populations stained to a much lesser extent, the fluorescence staining achieved with Protein A was sufficient to separate the brightest stained cells from background staining. In view of the advantages conferred over anti-sera, work continued with bulk as well as established cell lines.

Example 4

Correlation of High Protein A Fluorescence with Identifying/Sorting High Level IgG Secreting Cells The isolation of high IgG secreting clones after labelling with anti-human IgG antibodies is a method already used for biopharmaceutical cell line development (see Bresinsky et al, 2003, ibid), where it has been shown that high fluorescence corresponds to higher titres. To verify that our staining protocol, especially with Protein A, indeed identifies high producing cells we carried out a four-way sort on CHO-K1 based CHROMOS cells (Lindenbaum et al, NAR, 32, e172, 2004) transfected with a dAb-Fc fusion molecule (Project 17) and compared IgG staining to Protein A staining.

Figure 7A:
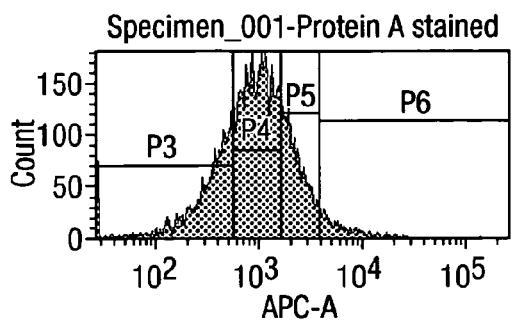
(FIG. 7A) shows the four-way gating across the Protein A (Alexa647 conjugated) and (FIG. 7B) across the anti-human IgG (DyLight649 conjugated) fluorescence histograms of live cells respectively. The % of cells within each gate were approximately 25% (P3 and P8); 50% (P4 and P9); 20% (P5 & P10) and 5% (P6 & P11).
Figure 7B:
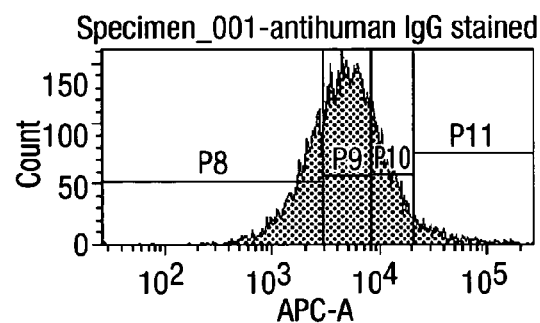
FIG. 7: Correlation of cell sort gating criteria and IgG expression after sorting. Four-way sorting of CHO-K1 derived CHROMOS ChK2 cells stably transfected with a vector for Project 17 was carried out. The cells were FACS sorted after staining with either anti-human IgG or Protein A.
(FIG. 7C) Antibody titre divided by the cell count from 5 days post sorting 100,000 cells per sort gate.
Figure 7C:
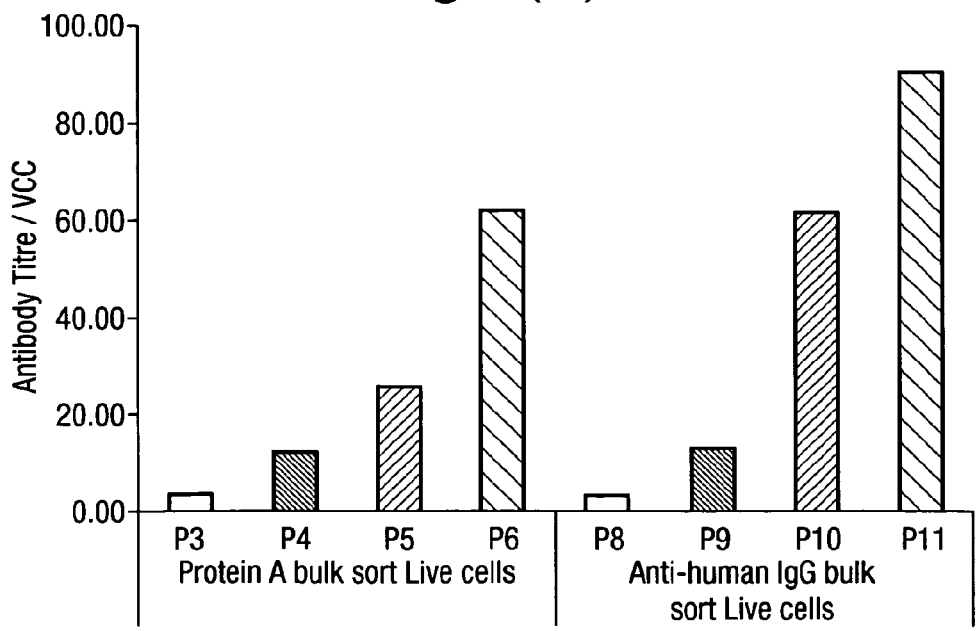

Soluble antibody was washed away and the cells were incubated with anti-human IgG at 4 μg/$10^6$ cells or Protein A at 0.5 μg/$10^6$ cells for 20 minutes on ice, in the dark. After two further washes in PBS the cells were sorted. A four-way enrichment sort was performed based on the gating across the fluorescence histogram plot of live cells (FIG. 7). One-hundred thousand cells were sorted per gate and were subsequently grown for 5 days in a sterile 24-well culture plate. Soluble IgG titres were then measured by MSD and the readings were divided by the viable cell count in the well to give an indication of a per cell productivity. Whilst the fluorescent signal was approximately 10-fold lower with Protein A staining, this data demonstrates a clear correlation between the level of Protein A staining and the IgG secretion of the cells similar to that seen with anti-human IgG labelling.

A second source of protein A (Repligen Protein A) that was labelled in house as described in the methods section was also used successfully (data not shown).

Example 5

Successful Sorting with IgG but Reduced Clones Growing Through from a Methotrexate Amplified Bulk Transfection Vs. a Pre-Cloned Line when Cell-Free Capture Plates were Used Generally speaking when cells are single cell sorted into capture plates if the plates contain feeder cells the latter facilitate the growth of the singly cloned cell (e.g. Hügin 1997, J Immunol Methods, 205, 211-212). To keep the protocol both simple and reproducible cell free capture plates were utilised. For this purpose capture plates only contained 50% conditioned medium (i.e. composed of 50% fresh medium and 50% filtered supernatant of a 3-4 day long culture of untransfected CHO cells) containing G418 and the appropriate amount of MTX.

After anti-Human IgG staining, a methotrexate (5 nM) amplified bulk transfection for antibody Project 14 was subjected to single cell FACS sorting. The same single cell sorting protocol was used for an established line (Project 3M, line D16); results are shown in Table 1 below. The plate capture data suggested the conditions were suitable for re-cloning established cell lines and for sorting the bulk transfected cells, although optimisation may be desirable to improve clone numbers produced from bulk transfections.

TABLE 1

Number of clones per plate after single cell sorting a methotrexate amplified bulk transfection Project 14 or a cloned line Project 11 into cell free capture plates

| | No. Single Cell Clones/Plate | |
| --- | --- | --- |
| | MTX Bulk (Project 14) | Cloned Line (Project 3M) |
| Plate 1 | 3 | 9 |
| Plate 2 | 1 | 10 |
| Plate 3 | 3 | 12 |
| Plate 4 | 0 | 6 |
| Plate 5 | 0 | 7 |

Example 6

Optimisation of Capture Plate Conditions for Clone Growth Post-Sort

To increase the numbers of clones produced post-sorting of single cell clones from bulk transfections we compared different capture plate conditions to the widely used standard of feeder cells. CHO DG44 cells were transfected with plasmids encoding the antibody for Project 13. The transfected cells were then subjected to G418 selection and nucleoside withdrawal, then 5 nM Methotrexate for gene amplification. Six different capture plate conditions were compared:

1) 2000 DG44 CHO cells per well in medium with G418 and Methotrexate added 64 hours after sorting;
2) 2000 DG44 CHO cells per well in medium with G418 and Methotrexate present prior to sorting;
3) 50% conditioned medium with G418 and Methotrexate added 64 hours after sorting;
4) 50% conditioned medium with G418 and Methotrexate present prior to sorting;
5) 50% conditioned medium with G418 and Methotrexate present prior to sorting with recombinant serum albumin and recombinant transferrin; and
6) Fresh medium with G418 and Methotrexate present prior to sorting with recombinant serum albumin and recombinant transferrin.

G418 was used at 400 µg/mL, Methotrexate was used at 5 nM, recombinant serum albumin was used at 1 mg/mL and recombinant Transferrin at 5 µg/mL. Media and G418 were sourced from Invitrogen, U.K. Methotrexate was prepared as a 50 µM stock from solid (Sigma, U.K.) and to remain animal protein free the recombinant albumin and Transferrin were both sourced as recombinant proteins from Novozyme, U.K. Five plates were sorted for conditions 1 to 4 and 6, and three plates for condition number 5. The numbers of clones produced per plate are shown in Table 2. The number of colonies produced per plate was counted 20 days after single cell sorting.

TABLE 2

Number of clones obtained from single cell sorting a methotrexate bulk transfection into capture plates with different conditions

| | No. Colonies per plate Plating Conditions | | | | | |
| --- | --- | --- | --- | --- | --- | --- |
| | 1) | 2) | 3) | 4) | 5) | 6) |
| Plate 1 | 12 | 6 | 3 | 2 | 8 | 1 |
| Plate 2 | 19 | 9 | 3 | 0 | 15 | 4 |
| Plate 3 | 8 | 9 | 7 | 1 | 5 | 8 |
| Plate 4 | 8 | 7 | 2 | 1 | | 2 |
| Plate 5 | 9 | 9 | 2 | 1 | | 4 |
| Mean | 11.2 | 8 | 3.4 | 1 | 9.3 | 3.8 |
| S.E.M. | 2.1 | 0.6 | 0.9 | 0.3 | 2.3 | 1.2 |

The data shows that the inclusion of G418 and methotrexate in the capture plate media leads to fewer clones both in the case of feeder cell plates and under cell free capture plate conditions. Inclusion of recombinant human serum albumin and Transferrin in the conditioned medium resulted in the increase of the number of clones growing through. The observed growth of clones in the absence of feeder cells indicates that cell-to-cell contact is less important than soluble factors such as those present in the conditioned medium and/or can be substituted by the recombinant albumin and Transferrin supplements. The absence of feeder cells in the plates improves the visual identification of clones in the 96-well plates and enables their earlier identification. The data above indicate that the addition of higher amounts of albumin and/or Transferrin to medium containing capture plates is likely to increase clone numbers, and could remove the need for use of conditioned medium. These data, combined with the previous example, show that a variety of different conditions can support the single cell cloning of CHO cells, albeit with different percentages of cells growing through.

Subsequently the derived colonies were analysed for antibody expression. The results, shown in Table 3, indicate that when using media without a feeder layer higher titres are obtained when the selection pressures (G418 and MTX) are added 2 days post cloning (compare condition 3 with 4).

TABLE 3

Antibody titre for clones obtained from single cell sorting a methotrexate bulk transfection into capture plates with different conditions

| Condition: | 1 | 2 | 3 | 4 | 5 | 6 |
|---|---|---|---|---|---|---|
| Min Titre, mg/L | 0 | 0 | 0 | 0 | 0 | 0 |
| Max Titre, mg/L | 46 | 117 | 20 | 5 | 22 | 9 |
| Average titre, mg/L | 3.5 | 7.2 | 3.1 | 1.4 | 1.2 | 1.0 |
| StDev (mg/L) | 8.6 | 22.5 | 6.0 | 2.1 | 4.3 | 2.6 |
| % non producing clones | 66 | 70 | 41 | 60 | 70 | 79 |
| % clones >5 mg/L | 20 | 20 | 18 | 0 | 9 | 14 |

To further refine the cloning conditions and given the encouraging results obtained above, another experiment was designed, whereby CHO DG44 cells were transfected with plasmids encoding an antibody. The transfected cells were then subjected to G418 selection and nucleoside withdrawal, then 5 nM Methotrexate for gene amplification. Three different capture plate conditions were compared (cells were sorted based on the live cell gate and 10 96-well plates were used per condition):
  1) 50% conditioned medium with G418 and Methotrexate present prior to sorting with recombinant serum albumin and recombinant transferrin;
  2) 50% conditioned medium with G418 and Methotrexate added 48 hours post-sorting and with recombinant serum albumin and recombinant transferrin present prior to sorting;
  3) 50% conditioned medium with Methotrexate added 48 hours post-sorting and G418, recombinant serum albumin and recombinant transferring present prior to sorting;

Three weeks post single cell sort colonies were counted and also antibody titres measured. The results, summarised in Table 4, show again a clear advantage of adding the selection pressure (G418 and MTX) 2 days after sorting.

TABLE 4

Clones obtained and productivity from single cell sorting a methotrexate bulk transfection into capture plates with different conditions

| Plating conditions | Number of colonies | Average colonies/plate | Max Titre (mg/L) | Average titre (mg/L) | % clones >1 mg/L |
|---|---|---|---|---|---|
| Condition 1 | 171 | 17 | 2.1 | 0.58 | 12.5 |
| Condition 2 | 67 | 7 | 6.8 | 1.26 | 50 |
| Condition 3 | 70 | 7 | 3.3 | 0.74 | 25 |

Example 7

Figure 8A:
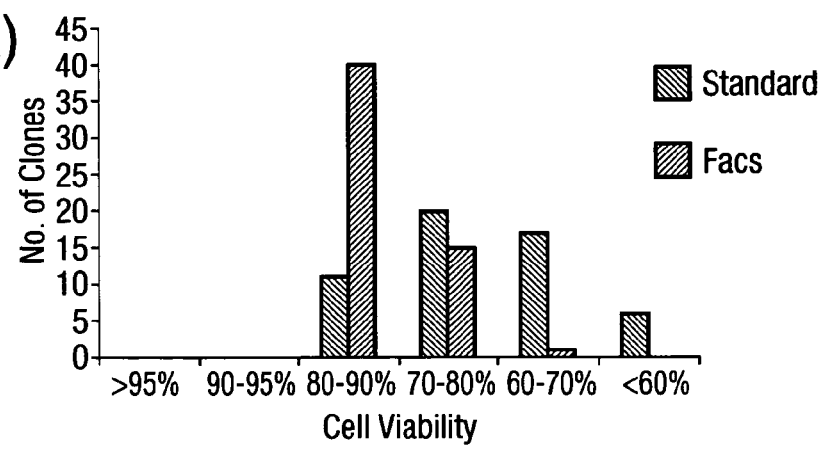
FIG. 8A Viability of cells at the T75 cm2 static tissue culture flask stage of clones derived from either selection/amplification in bulk and single cell cloning by FACS (in grey) or low density plating (conventional/standard protocol—in black).
Figure 8B:
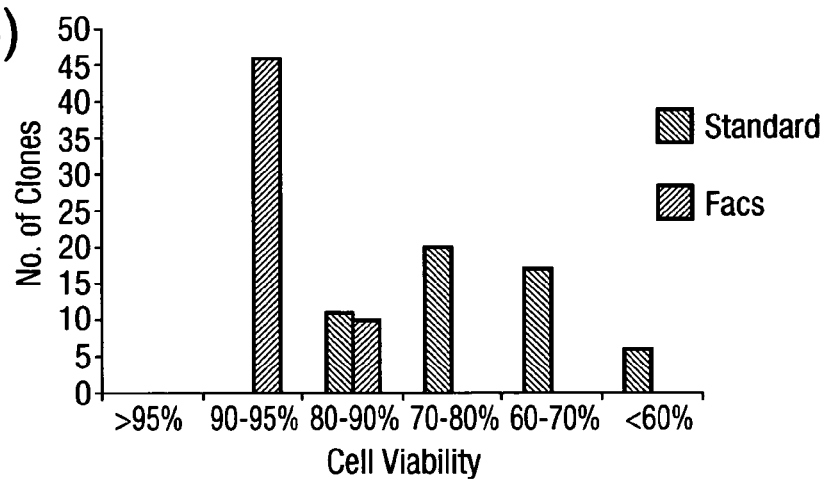
FIG. 8B Viability of the same clones measured at the early shake flask (SF) stage.
Figure 8C:
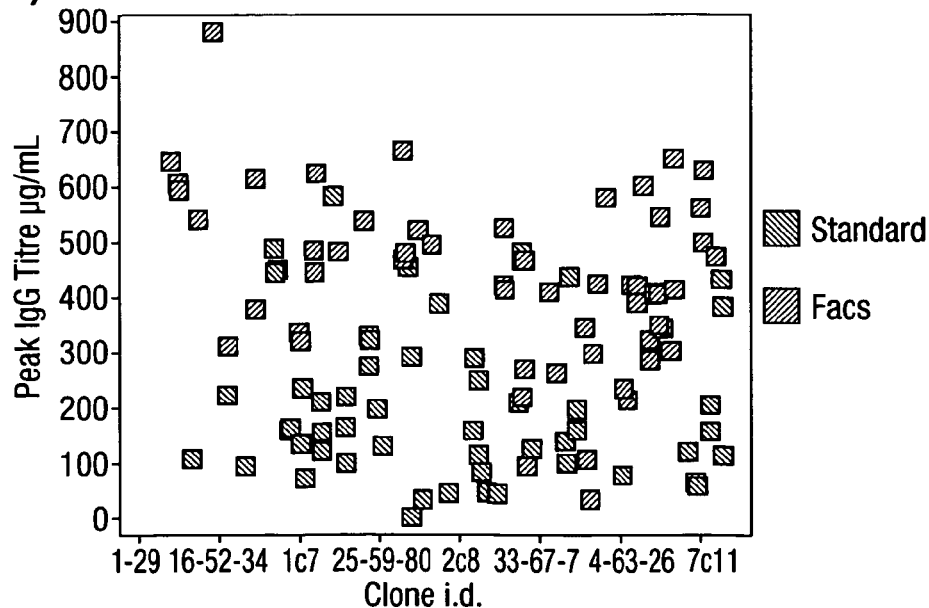
FIG. 8C Day 14 IgG titres of the same clones in miniature growth curve (Duetz) model showing FACS (grey boxes) and conventional/standard protocol (black boxes) data.

Earlier Recovery of FACS Sorted Clones and Better Response to Feed in Batch Production when Compared to Clones Derived from the Conventional Method For Project 13 we compared the recovery of selected cells after (a) low density plating (conventional protocol, FIG. 1(A)) and (b) single cell sorting of high-fluorescing cells from stained amplified bulk pools (new protocol, FIG. 1(B)). We looked at viabilities at scale-up and cumulative IgG titre achieved in batch miniature (Duetz) production models set up from T75 cm flasks. The data are shown in FIG. 8. Surprisingly, there was a much more rapid recovery and adaptation to shaking culture of the clones derived from the FACS protocol (see FIGS. 8(A) and 8(B)). The majority of FACS clones recovered to >80% viability at the T75 stage and >90% at the first passage in shake flasks while even at the shake flask stage the majority of the conventional protocol lines were still <80% viable. In addition to the superior cell viability the cells produced from the FACS protocol (grey boxes) were superior to their conventional protocol derived peers (black boxes) with regards to IgG production as shown in FIG. 8(C).

In addition, the clones derived from single cell sorting of high fluorescing cells (by FACS) were compared to clones that were derived from the conventional method) with regard to their response to feed in batch production shake flask models (whereby a single bolus feed of 5-10% yeastolate was added at day 7 of culture). Table 5 shows that 96% of FACS clones produced higher titres with feed compared to 25% of the conventional clones. In addition, the FACS clones had a much greater mean % increase in fed batch titre, 45% vs. 19% and a greater maximum titre increase 105% vs. 34%. These data suggest that FACS cloning is a better method to generate more robust and feed responsive clones for biopharmaceutical production.

TABLE 5

Response to feed in batch production of cells sorted by FACS for high-fluorescence versus "conventional" technique

| | Project 13 | |
|---|---|---|
| | FACS | Conventional |
| Total number of clones | 28 | 28 |
| No. Clones with feed response | 27 | 7 |
| % Feed responders | 96 | 25 |
| Mean % Titre Increase with Feed | 45 | 19 |
| Minimum Titre Increase | +7.9 | +7.5 |
| Maximum Titre Increase | +105 | +34 |

Example 8

Enhanced Fluorescence Observed when Cells are Analysed According to their FSC-A Vs. FSC-H Profile A discrete subpopulation of live cell events with higher FSC-A in an FSC-H vs. FSC-A plot was observed on the flow cytometer. This cell subpopulation was named the HFA subpopulation, due to its high forward scatter area, which is indicative of larger cell size. This population lies within the same FSC-H boundaries as the main cell population. In fact, the FSC-H of these HFA cells was 1.1 (+/−0.1) times that of the other cells within the FSC-H boundaries (n=32). This "other cell" subpopulation was named the LFA (low forward scatter, indicative of smaller cell size). Despite the similarity in FSC-H, the mean FSC-A of the HFA subpopulation is 1.8(+/−0.1) times that of the LFA subpopulation (n=32).

Figure 10B:
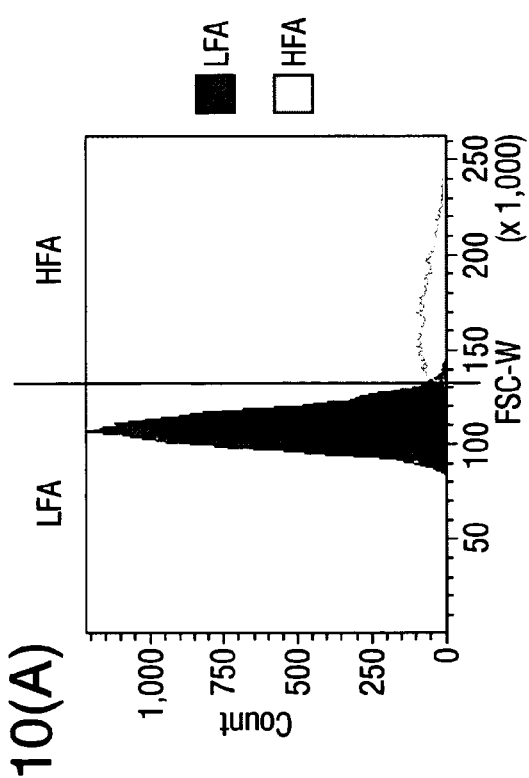
Figure 10C:
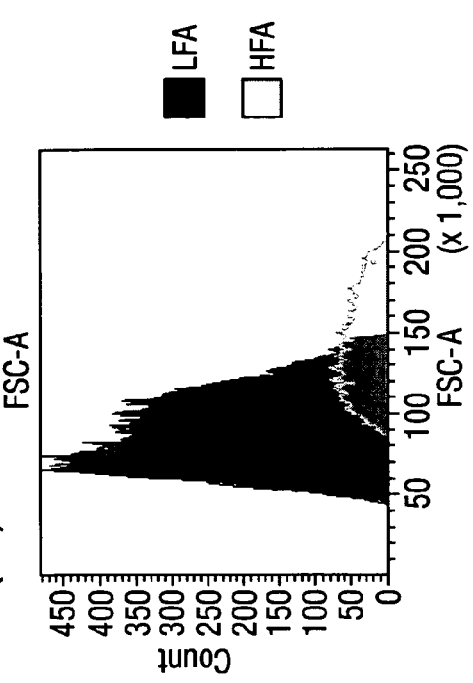
Figure 10D:
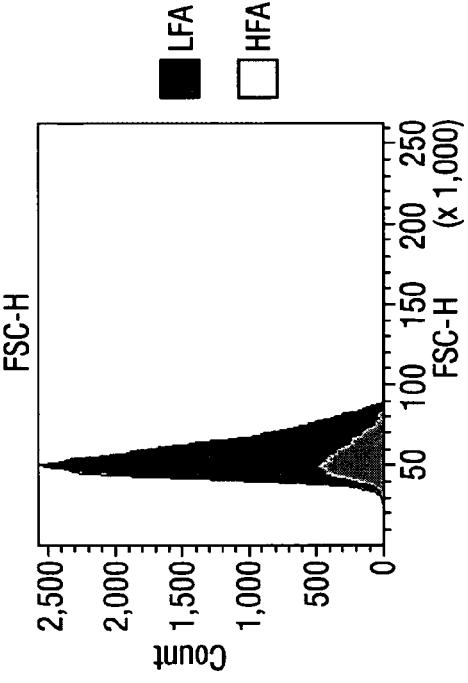

However, in an FSC-H vs. FSC-A plot, there is an overlap between HFA and LFA subpopulations on the FSC-A axis. With an n=22, 71% (+/−25) of the HFA cells have an FSC-A higher than the overlapping area, with a minimum of 38% and a maximum of 100%. Nevertheless, the HFA subpopulation of cells could be clearly identified by a person of skill in the art of flow cytometry, and the gating of each population could be determined accordingly. As a representative example, the diagonal lines in FIG. 9B divide the live cell subpopulation into two clearly distinct subpopulations; the HFA cell subpopulation lie on the right hand side of the diagonal line that is drawn to track the bottom edge of the main population in the FSC-H (Y axis) vs. FSC-A (X axis) plot. When the same data are plotted as a histogram (FIG. 10) the FSC-W value of the HFA cell subpopulation is higher than that of the LFA cell subpopulation. HFA cells can therefore be defined as the sub-population of live cells (as gated in FSC-A vs. SSC-A plots) that have higher FSC-W that can be gated either in FSC-H/FSC-A plots (FIG. 9) or FSC-W histogram (FIG. 10A), or FSC-W/FSC-A plot (FIG. 10B). As shown in Example 14, it is also possible to gate the HFA cells directly in an FSC-A vs. SSC plot (FIG. 22).

Upon microscopic examination post sort (gating on the FSC-H/FSC-A plot of live cells), this subpopulation of cells consists of mainly larger single cells and not cell aggregate/clumps. It should be noted that high FSC-W cells (or 'events') are traditionally excluded from analysis-sorting as they form part of gating strategies to eliminate cell doublets. This can be done for example in FSC-W or FSC-H vs FSC-A plots. However, it has recently been shown for T cells that such sub-population may rather contain highly active/proliferating cells (Bohmer at al, Cytometry part A, 2011, 00A: 1-7).

Sorting (gating on the FSC-H/FSC-A plot of live cells) and subsequent culture of this HFA subpopulation produced robust cell growth and antibody titres which exceeded their LFA subpopulation peers. The HFA population constitutes approximately 2-20%, more typically 5-10%, of the whole population of live cells. We hypothesise that this population represents a dynamic part of the live cell population—possibly the actively proliferating fraction—with its numbers changing depending on the sampling time point.

In addition, after sorting, the HFA cells revert to the general population FSC-A vs. FSC-H profile. However, the HFA subpopulation produced consistently higher levels of fluorescence than the LFA subpopulation (indicated in the histograms; FIG. 11). The higher fluorescence of this population was observed regardless of the staining method used—Protein A or anti-IgG. Importantly for bulk transfections, cloning from only the HFA subpopulation enables a clear separation of positively stained Protein A cells. (FIG. 11).

Figure 12A:
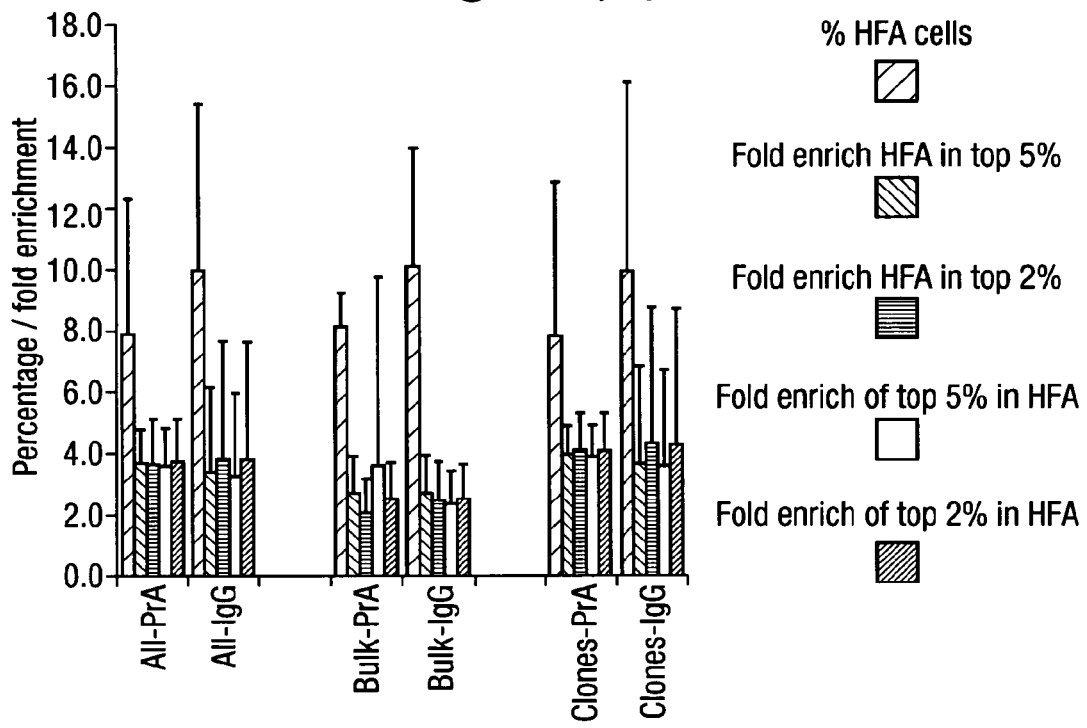
FIG. 12A % of HFA cells (black), fold enrichment in HFA cells of the top 5% live fluorescing cells compared to live cells—i.e. shows (% of top 5% live gate that are HFA)/(% of Live cells that are HFA) (mid-grey), fold enrichment in HFA cells of the top 2% live fluorescing cells compared to live cells—(dark grey), fold enrichment in top 5% live fluorescing cells of the HFA cells compared to live cells—i.e. shows (% of HFA cells in the top 5% live gate)/(5) (light grey) and fold enrichment in top 2% live fluorescing cells of the HFA cells compared to live cells (white). The X axis shows the type of cells and type of staining analysed.
Figure 12B:
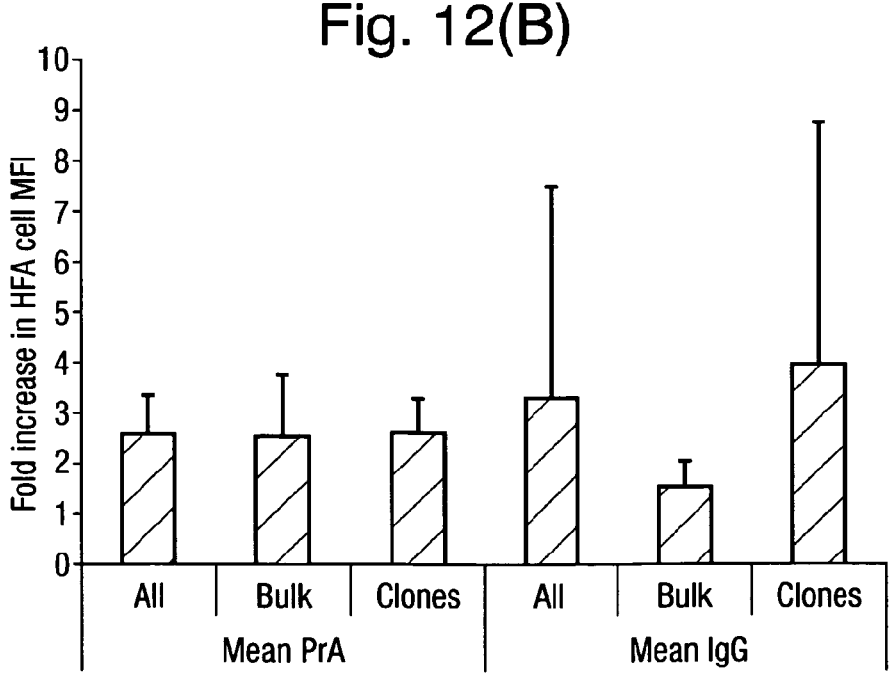
FIG. 12B The fold-increase of mean fluorescence intensity of HFA cells compared to live cells for parental, bulk transfected populations and established cell lines following staining with labelled rabbit anti-human IgG or Protein A.

Building on the above, a number of established lines and bulk transfections involving different antibody projects were analysed for HFA % and IgG or Protein A staining of HFA and LFA cells and the results are shown in FIG. 12. These show that the HFA subpopulation forms a larger percentage of the top fluorescing cells when stained with either fluorescently labelled Protein A or anti-human IgG. They also show that the mean fluorescence of cells in the HFA subpopulation is significantly higher when compared to that of the LFA subpopulation.

Example 9

Sorting HFA Cells Results in an Enrichment for Selection of High Producers and in the Generation of Cell Lines with Equal or Increased Stability Two different sorts, presented below, were performed to assess the value of using the FSC-A vs. FSC-H characteristics for the identification and isolation by FACS sorting of high producers:

1. An established line, Project 10—line MTX8, was single cell cloned using 3 different approaches (FIG. 13A): (a) limiting dilution (9×96-well plates were set-up), (b) FACS cloning of just live gated cells, on SSC vs. FSC plot (7×96-well plates were set-up), and (c) FACS cloning of HFA cells, gate on live and then HFA on the FSC-H vs. FSC-A plot (1×96-well plate was set-up). As shown in FIG. 13B, the highest producing clone was one of the HFA clones and was also proven to be stable even after 50 passages.
2. An established line, Project 3M—FACS sort was performed and the HFA cell subpopulation were sorted at single cell level. The line prior to sort was unstable, with batch titres declining with increasing passages, with the decline starting to be noticable after passage 20 (FIG. 14A). The data obtained showed the HFA derived clonal lines had much increased batch titres and stability compared to the parent—representative data for one clone are shown in FIG. 14B.

Example 10

Figure 15A:
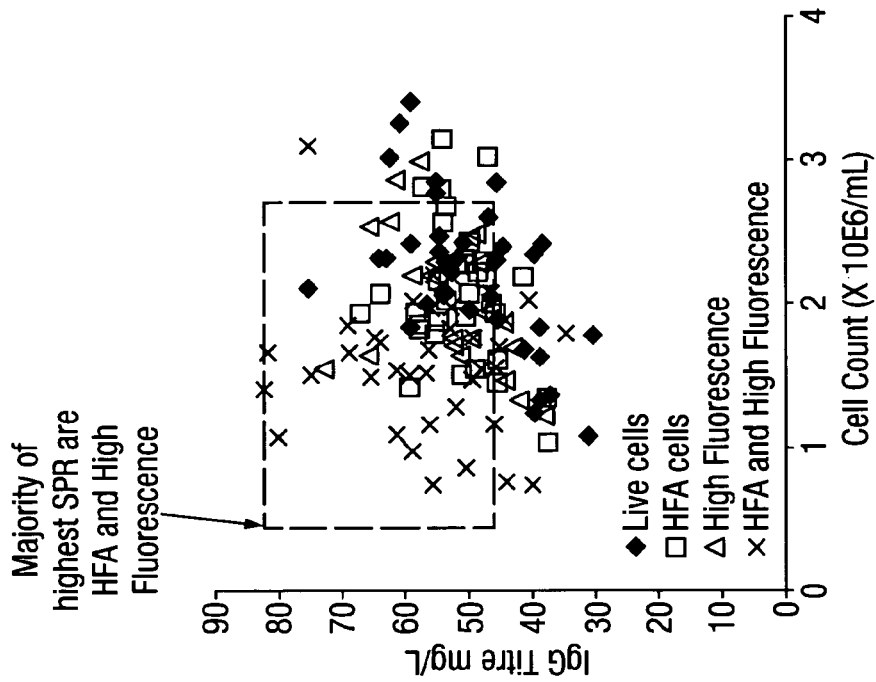
FIG. 15A Individual titres at the 6-well stage post single cell sub-cloning by FACS. Clones were derived from FACS sorting with four different sort criteria—1) Live cell gate (black); 2) HFA cells (white squares); 3) High Fluorescence cells: live gated cells with the top 1.5% fluorescence (rabbit-anti-human IgG staining) (white triangles) and 4) HFA high fluorescence cells: HFA cells within the top 1.5% fluorescence gate (black crosses).
Figure 15B:
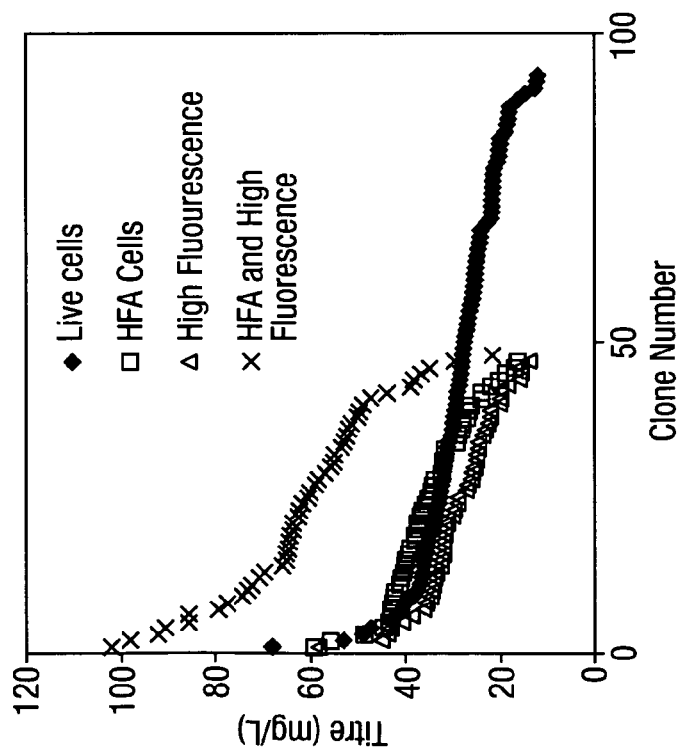
FIG. 15B Antibody titres and cell counts at the shake flask stage (passage 1). The same colour/shape scheme applies. This data demonstrates that the majority of clones that produce the highest antibody titres and the majority with the highest specific productivity (SPR) originate from the HFA and high fluorescence sorting criterion (black crosses).
Figure 16B:
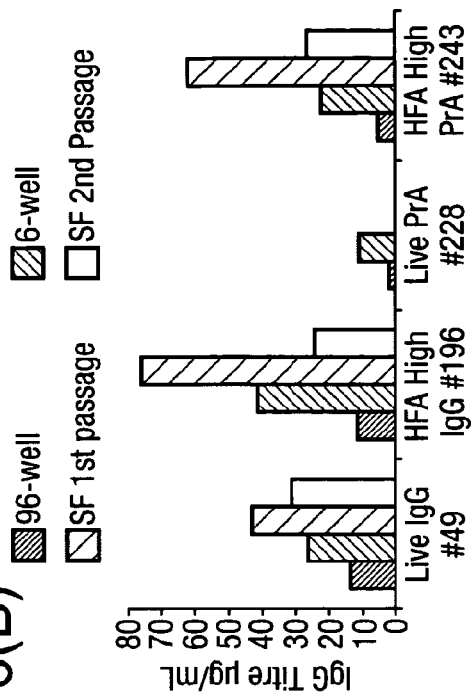
(FIG. 16B) shows the IgG titre of the top clone from each sub-sort criteria at different stages (96-well, 6-well and SF passage 1 and 2).
Figure 16A:
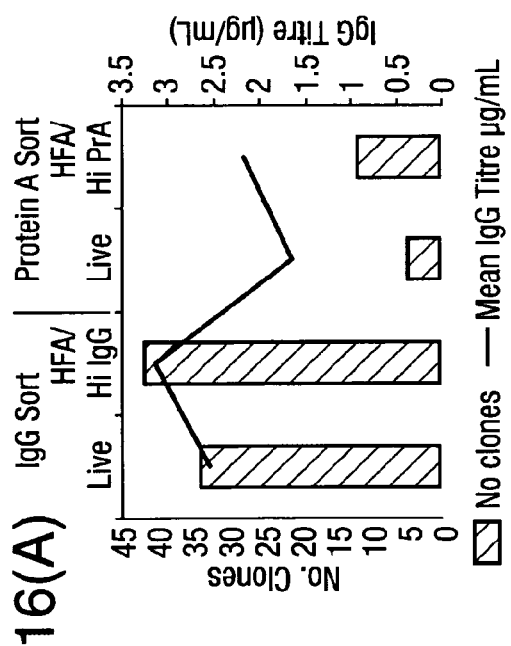
(FIG. 16A) shows the number of clones and mean titres achieved after sorting at the 96-well stage—data shown are for clones with titres equal or greater than 1 mg/L at this stage.
Figure 16C:
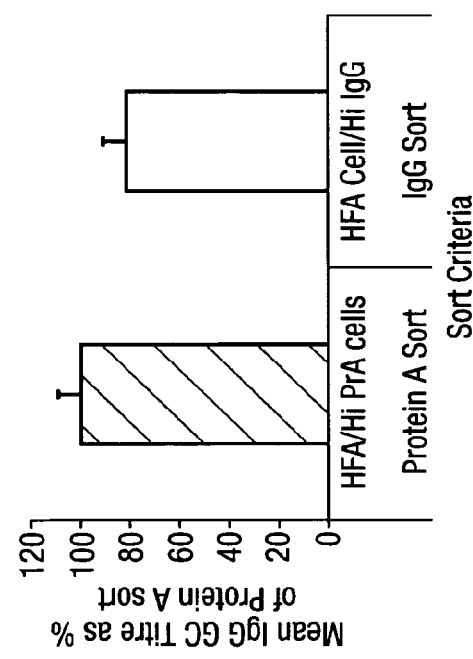
(FIG. 16C) shows a comparison between the mean batch production IgG titre at day 15 for the top HFA High Protein A sorted cell clones (n=2) and the top HFA High anti-human IgG sorted cell clones (n=3).
Figure 17:
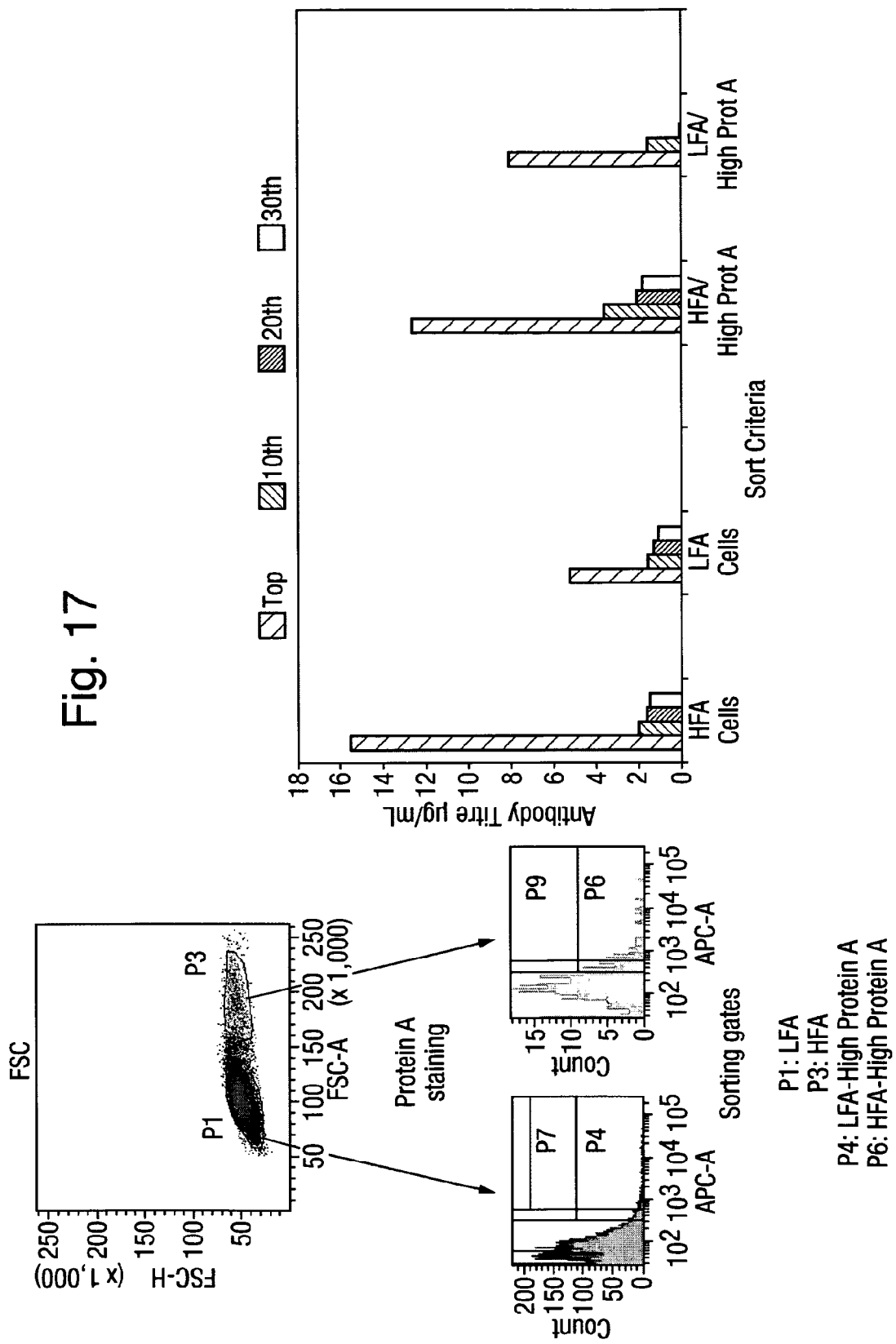
FIG. 17: Generation of clonal cell lines for Project 14 by FACS using the HFA and Protein A gating. CHO-DG44 cells were transfected with vectors encoding the antibody for Project 14 and were subsequently selected and amplified in bulk. Subsequently the bulk population was stained with Protein A and single cell sorted. On the left side the FSC-H/FSC-A plot of live cells is shown with gating for HFA and LFA populations; Protein A fluorescence histograms for the LFA and HFA populations are shown below, with a summary of the gates used for single cell sorting. The graph on the right shows the antibody titres from the top, 10th, 20th & 30th highest expressing clone respectively for the different sort criteria at the 96-well stage.
Figure 20:
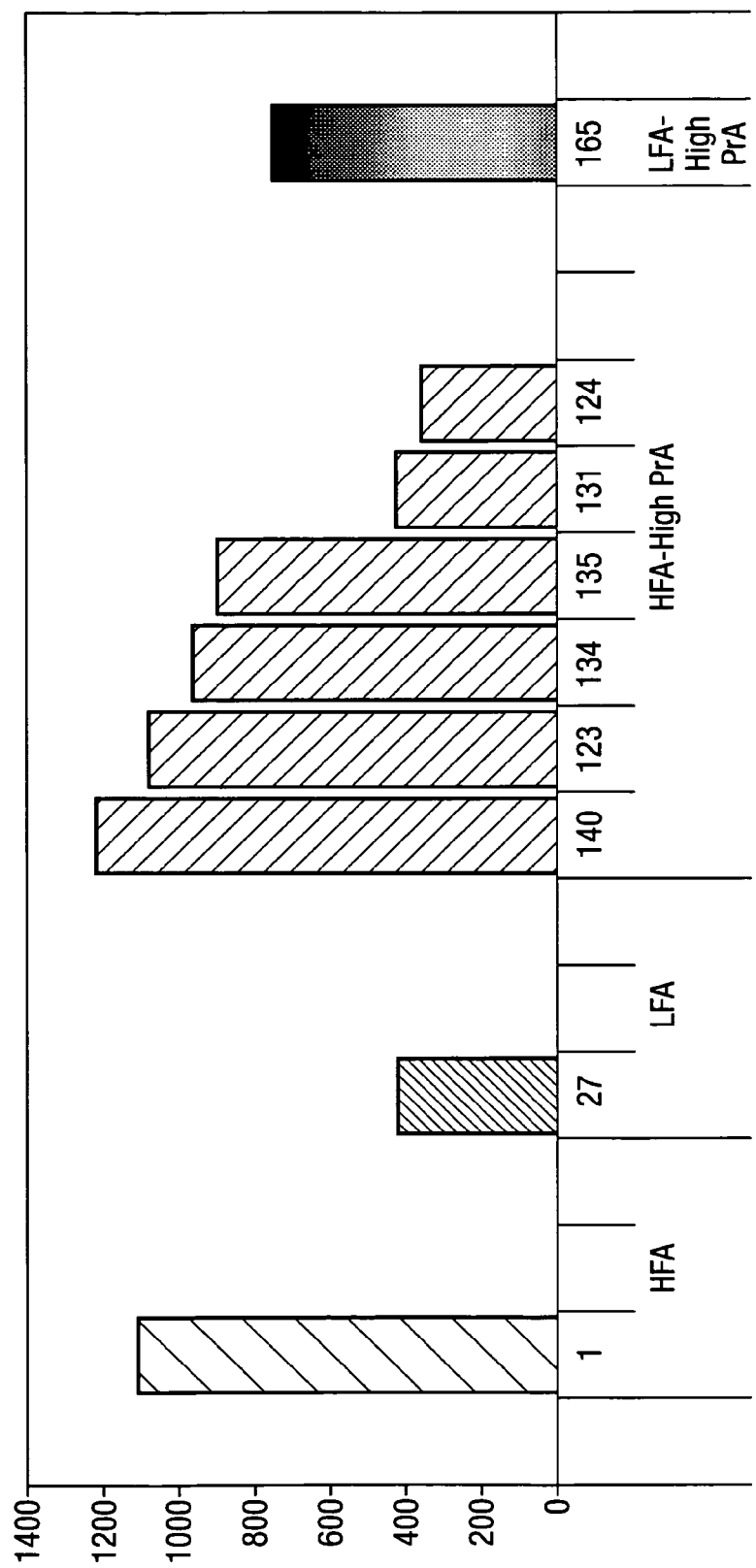
FIG. 20: Generation of clonal cell lines for Project 14 by FACS using the HFA and Protein A gating—scale-up data (see FIG. 17 for sorting gates and 96-well data analysis). Best shake flask production titres for the best clones from each sort (HFA, LFA, HFA-High Protein A and LFA-High Protein A) are shown. Y axis: Cumulative titre, mg/L. X axis: clone number/sort type.

Sorting HFA, or HFA-High Cells Results in an Enrichment for Selection of High Producers Four different sorts, presented below, were performed to assess the value of using Protein A (and IgG) staining combined with the FSC-A vs. FSC-H characteristics for the identification of high producers:

i. An established line, Project 3M, IgG sort—Single cell sorts were performed post staining with fluorescent anti-human IgG on 'Live' cells, HFA cells, Live cells with high fluorescence (top 1.5% fluorescence) or HFA cells with high fluorescence. The results (shown in FIGS. 15A & B) show the benefit of sorting on the basis of the forward scatter characteristics (i.e. the HFA sort) and high fluorescence to isolate high producers. FIG. 15A shows the individual clone titres and number of clones at the 6-well stage after sorting. This data shows the HFA cells with high fluorescence had much higher titres than the other three sort criteria at the 6-well stage and that this trend continues through to antibody secretion at the shake flask stage where these clones form the majority of the highest SPR (specific productivity) clones (FIG. 15B). It should be noted that the top few clones from all four sorts were progressed further and showed much increased batch titres and stability compared to the parent line prior to the sort.

ii. A bulk transfection, Project 10, IgG and Protein A sort—Bulk transfection, selection, amplification and staining were performed as described in previous examples. The bulk was sorted after staining with either polyclonal anti-human IgG or Protein A. The results in FIG. 16(A) show the number of clones produced and the average level of IgG secreted at the 96-well plate stage. In comparison to their live sort peers, the sub-sort of HFA cells with high fluorescence (either after anti-IgG or Protein A staining) produced more clones and with consistently higher levels of IgG production. This trend was retained when the cells were looked at at later stages of cell-line development (FIG. 16(B), showing secreted titres for best clone for each condition at different stages, as indicated). And although the top live cell sorted clone (clone 49, FIG. 16B) produced similar IgG titres at the 2nd shake flask passage when compared to its top HFA-High fluorescence counterpart, on further culturing it was only the 'HFA, high fluorescence' clones that made it to the growth curve stage. FIG. 16(C) shows data for the cells that made it through to unfed batch production models—titre shown here was taken at day 15, indicating that Protein A is potentially superior to the anti-IgG sera for selecting high producing clones.

iii. A second bulk transfection, Project 14, Protein A sort—Bulk transfection, selection, amplification and staining were performed as described in previous examples. Staining was performed with Protein A. In addition to sorting the HFA and HFA high fluorescence cell populations, the LFA and LFA, high fluorescence populations were also single cell cloned. FIG. 17 shows relevant FACS plots and sorting gates (on the left) as well as 96-well plate data from the single cell clones of this sort (on the right). This data demonstrates that the HFA cell population produces higher expressing clones than the LFA cells, regardless of whether stained or not with Protein A (similar data were obtained with staining with anti-IgG, data not shown). However, when staining was used in combination with gating for HFA cells, a much larger proportion of the clones had high levels of secreted IgG production (compare 10th, 20th and 30th ranking titres in FIG. 17). The results again demonstrate that Protein A can be successfully used instead of the polyclonal animal derived labeling antibody, that applying the HFA gate results in increased titres and applying the 'HFA-High fluorescence' gate results in more consistently high titres. Clones were subsequently scaled up and re-analysed at the 6-well and shake flask production stage, where again it was clear that applying the HFA gate results in increased titres and applying the 'HFA-High fluorescence' gate results in more consistently high titres and a greater number of high producing cell lines (Table 6 and FIG. 20).

TABLE 6

6-well titre data analysis for the clones derived from the different sorts (HFA, LFA, HFA-High Protein A and LFA-High Protein A).

| 6-well data | No Clones >9.26 mg/L | % Clones >9.26 mg/L | Mean titre (mg/L) | Top titre (mg/L) |
|---|---|---|---|---|
| HFA | 2 | 8 | 28.8 | 36.1 |
| LFA | 1 | 4 | 11.8 | 11.8 |
| HFA High PrA | 8 | 33 | 36.2 | 79.8 |
| LFA-High Pra | 2 | 8 | 26 | 30.3 | iv. Clones were also generated for another project as described in (iii) above, where HFA and HFA-High Protein A only clones were sorted, analysed and scaled up. Again both in 96-well, but more so in shake flask production, there is a clear advantage in using the HFA-High fluorescence gate for the identification of high producer cell lines (FIG. 21).

Example 11

Improved Predictability of Productivity and Need to Scale-Up a Much Smaller Number of Clones after Implementation of the FACS Protocol All cell line development protocols to date require the screening and scale up of hundreds if not thousands of clones to generate cell lines suitable for biopharmaceutical manufacturing regimes. We tried to determine the number of clones required to scale-up from the earliest 96-well plate stage in order to guarantee the isolation of the highest producing clones in batch production models. For this purpose we analysed four different experiments, presented below, ranked the top 4-5 clones (at production curve stage) and then looked at their ranking at previous stages in culture. The data is presented below.

1) Project 14, Protein A Labelled Cell Sort (for Top 2% Stained [High Fluorescence] Cells)

Bulk transfection, selection, amplification and staining were performed as described in previous examples. The bulk was single cell sorted after staining with Protein A the results are shown in Tables 7 and 8 below:

TABLE 7

Summary of sub-sort criteria, number of plates sorted and resulting clone numbers screened/scaled up at each stage (96-well and shake flask, SF) for Project 14

| | | No Clones evaluated | |
|---|---|---|---|
| Sort criteria | No Plates sorted | 96 well | SF |
| LFA | 7 | 37 | 1 |
| HFA | 7 | 73 | 2 |
| LFA-High PrA | 7 | 23 | 2 |
| HFA-High PrA | 7 | 84 | 8 |
| Total: | 28 | 217 | 13 |

TABLE 8

The top 5 clones at growth curve analysis are shown for Project 14 and with data indicating their ranking at earlier stages

| Growth curve Ranking | Clone i.d. | Ranking 96-well | 6-well | T75cm² flask | Sort criteria |
|---|---|---|---|---|---|
| 1 | 140 | 5 | 1 | 1 | LFA-High PrA |
| 2 | 1 | 1 | 4 | 3 | HFA |
| 3 | 123 | 3 | 2 | 4 | HFA-High PrA |
| 4 | 134 | 4 | 3 | 2 | HFA-High PrA |
| 5 | 165 | 9 | 7 | 9 | LFA-High PrA |

Table 7 shows the number of clones that were evaluated at the 96-well and shake flask stage after Protein A labelling cells transfected with Project 14 vectors and sorting them on the four sorting criteria indicated. This data indicates that the number of colonies obtained from the HFA or HFA-High sort was significantly higher than that for the LFA or LFA-high sorts. Table 8 shows the ranking of the highest batch production titre achieving clones at different earlier stages (96-well, 6-well and T75). Surprisingly, these data demonstrate that four of the 5 top producing clones could be predicted from the 5 top clones even at the 96-well stage.

2) Project 14, IgG Labelled Cell Sort (for Top 2% IgG Stained Cells)

Bulk transfection, selection, amplification and staining were performed as described in previous examples. The bulk was single cell sorted after staining with IgG the results are shown in Tables 9 and 10 below:

TABLE 9

Summary of sub-sort criteria, number of plates sorted and resulting clone numbers for Project 14, both at 96-well and shake flask stage

| | | No. Clones | |
|---|---|---|---|
| Sort Criteria | No. plates sorted | 96-well | SF |
| LFA High | 7 | 29 | 5 |
| HFA High | 7 | 80 | 11 |

TABLE 9-continued

Summary of sub-sort criteria, number of plates sorted and
resulting clone numbers for Project 14,
both at 96-well and shake flask stage

| Sort Criteria | No. plates sorted | No. Clones 96-well | SF |
|---|---|---|---|
| HFA High (CM) | 7 | 82 | 13 |
| Total | 21 | 191 | 29 |

TABLE 10

The top 5 clones at growth curve analysis are shown
for Project 14 and with data indicating their
ranking at earlier stages

| Growth curve ranking | Clone i.d. | Ranking 96-well | 6-well | T75cm$^2$ flask | Sort criteria |
|---|---|---|---|---|---|
| 1 | 61 | 4 | 3 | 2 | HFA High IgG |
| 2 | 68 | 2 | 1 | 3 | HFA High IgG |
| 3 | 55 | 3 | 5 | 4 | HFA High IgG |
| 4 | 119 | 45 | 28 | >32 | HFA High IgG CM |
| 5 | 93 | 5 | 22 | 18 | LFA High IgG |

Table 9 shows the number of clones that were evaluated at the 96-well and shake flask stages after anti-IgG labelling cells transfected with Project 14 vectors and sorting them via the sorting criteria indicated. For the LFA High fluorescing cells the cloning was performed using capture plates with feeder cells (as described in previous sections), whereas for the HFA High fluorescing cells 2 different conditions were used: feeder cells or conditioned media (CM). From this data the number of clones produced from the HFA cells with high fluorescence' sub-sort was again higher. Also four out of five of the top clones in the batch production model (Table 10) were 'HFA high' sorted cells. The data also demonstrates that four of the top five growth curve producing clones could be predicted from the 5 top clones at the 96-well stage. For three of these clones this ranking is retained through 6-well and shake flask stages (pre-growth curve analysis).

3) Project 10, IgG or Protein A Labelled Cell Sort (for Top 5% Protein A Stained Cells)

Bulk transfection, selection, amplification and staining were performed as described in previous examples. The bulk was single cell sorted after staining with IgG the results are shown in Tables 11 and 12 below.

TABLE 11

Summary of sub-sort criteria, number of plates
sorted and resulting clone numbers for Project 10
(at 96-well and shake flask stage)

| Sort Criteria | No. plates sorted | No. Clones 96-well | SF |
|---|---|---|---|
| Live IgG | 5 | 99 | 2 |
| HFA High IgG | 5 | 109 | 7 |
| Live PrA | 5 | 29 | 0 |
| HFA High PrA | 5 | 46 | 3 |
| Total | 20 | 283 | 12 |

TABLE 12

The top 5 clones at growth curve analysis are shown
for Project 10 and with data indicating their
ranking at earlier stages

| Growth curve Ranking | Clone i.d. | Ranking 96-well | 6-well | T75cm$^2$ flask | Sort criteria |
|---|---|---|---|---|---|
| 1 | MTX243 | 8 | 5 | N.D. | HFA High PrA |
| 2 | MTX169 | 3 | >16 | N.D. | HFA High IgG |
| 3 | MTX125 | 5 | >16 | N.D. | HFA High IgG |
| 4 | MTX265 | 7 | >16 | N.D. | HFA High PrA |
| 5 | MTX187 | 70 | >16 | N.D. | HFA High IgG |

Table 11 shows the number of clones that were evaluated at the 96-well and shake flask stages after either anti-IgG or Protein A labelling cells transfected with Project 10 vectors and sorting them via the two sorting criteria, either 'Live gated' or 'HFA cells with high fluorescence'. From these data the number of clones produced from the sub-sort of 'HFA cells with high fluorescence' were again higher than those for the live sorted cells. In addition, all the top five clones in growth curves (Table 12) were from the 'HFA high' cells, with the highest being a HFA High-Protein A sorted clone. The data again demonstrates that the prediction from the top 8 clones at 96-well stage is good, four of them reaching the top 5 in growth curves.

4) Project 3M HFA Cell IgG or Protein A Labelled Cell Sort (for Top 5% Protein A Stained Cells)

Two subclones of Project 3M line BP0044 were re-cloned by FACS: (a) Cell line C1 (originally single cell sorted as Live top 1.5% IgG staining of parental BP0044); and (b) Cell line D16 (originally single cell sorted as HFA top 1.5% IgG staining of parental BP0044). C1 and D16 were re-sorted selecting single cells from the top 5% fluorescence and HFA cell population, after labelling the cells with either fluorescent protein A or anti-human IgG. The results are shown in Tables 13 and 14 below:

TABLE 13

Summary of sub-sort criteria, number of plates sorted and resulting
clone numbers for Project 3M (at 6-well and shake flask stage).

| Sort Criteria | No. plates sorted | No. Clones 6-well | SF |
|---|---|---|---|
| Clone C1 HFA High IgG | 5 | 17 | 6 |
| Clone D16 HFA High IgG | 5 | 44 | 12 |
| Clone C1 HFA High PrA | 5 | 8 | 4 |
| Clone D16 HFA High PrA | 5 | 15 | 1 |
| Total | 20 | 84 | 23 |

TABLE 14

The top 5 clones at growth curve analysis are shown
for Project 3M and with data indicating their
ranking at earlier stages

| Growth curve Ranking | Clone i.d. | Ranking 6-well | T75cm$^2$ flask | Sort criteria |
|---|---|---|---|---|
| 1 | P7G4 | 16 | 11 | HFA-High IgG |
| 2 | P2G5 | 4 | 4 | HFA-High IgG |
| 3 | P8G8 | 8 | 10 | HFA-High IgG |

TABLE 14-continued

The top 5 clones at growth curve analysis are shown for Project 3M and with data indicating their ranking at earlier stages

| Growth curve Ranking | Clone i.d. | Ranking 6-well | T75cm² flask | Sort criteria |
|---|---|---|---|---|
| 4 | P14F9 | 1 | 2 | HFA-High PrA |
| 5 | P8E2 | 10 | 18 | HFA-High IgG |

Table 13 shows the number of clones that were evaluated at the 6-well and shake flask stages. 96-well titre data were not obtained at this occasion and hence are not shown. From these data four of the top five clones at the growth curve stage derive from the top ten clones at the 6-well stage (Table 14).

To summarise, the findings of these 4 examples described above demonstrate that the novel protocol according to the invention results in the identification of the highest producing clones from as early as the 96-well stage. This is believed to be the first protocol for CHO-based biopharmaceutical cell line development that describes the identification of final cell lines from within the top 5-10 of the initial 96-well screen.

In addition, collectively and when compared to other sort criteria the HFA cells with high fluorescence consistently produce the majority of the highest producing clones in batch production models.

Further analysis was performed to compare the FACS based protocol as described herein with previously used conventional CLD protocols (e.g. as described in WO2009024567 and Kotsopoulou et al J Biotechnol, 2010). For this purpose we analysed 7 different antibody projects where the bulk transfection/amplification and cloning by FACS(HFA-high protein A) protocol was used. Also 7 projects where conventional plating/amplification protocols were used were analysed. In both cases the top 1-2 clones as ranked in shake flask production models were tracked back and their ranking recorded at the 96-well and the 6-well stage of their selection—in the conventional protocol these rankings were only tracked at the final amplification stage. The results, shown in the Table 15, show that upon implementation of the FACS protocol (and HFA-High protein A gating), there is higher predictability of clone performance and indicates that only a small number of clones need to be scaled up to select a highly productive cell line suitable for manufacturing. If we also take into account that for the conventional protocol in the majority of cases this is not the first ranking but one or more amplification/selection rounds preceded the final round recorded below then these results are even more impressive.

TABLE 15

| Historical analysis of predictability (SF: Shake Flask production model) | | | | |
|---|---|---|---|---|
| Protocol | Individual rankings of top 1-2 SF in 96-well stage | Individual rankings of top 1-2 SF in 6-well stage | Mean ranking of top 1-2 SF in 96-well stage (StDev) | Mean ranking of top 1-2 SF in 6-well stage (StDev) |
| FACS | 3, 1, 5, 3, 14, 19, 5, 1, 27, 9, 1, 2 | 1, 2, 2, 1, 16, 4, 1, 4, 10, 16, 1, 2 | 8$^{th}$ (8) | 5$^{th}$ (6) |
| Conventional | 1, 3, 12, 33, 3, 9, 1, 5, 75, 113, 19, 4, 3, 15, 43, 47 | 1, 4 2, 4, 32, 37, 1, 2, 2, 1, 2, 3, 13, 1, 6, 13 | 24$^{th}$ (32) | 8$^{th}$ (11) |

Example 12

Figure 18A:
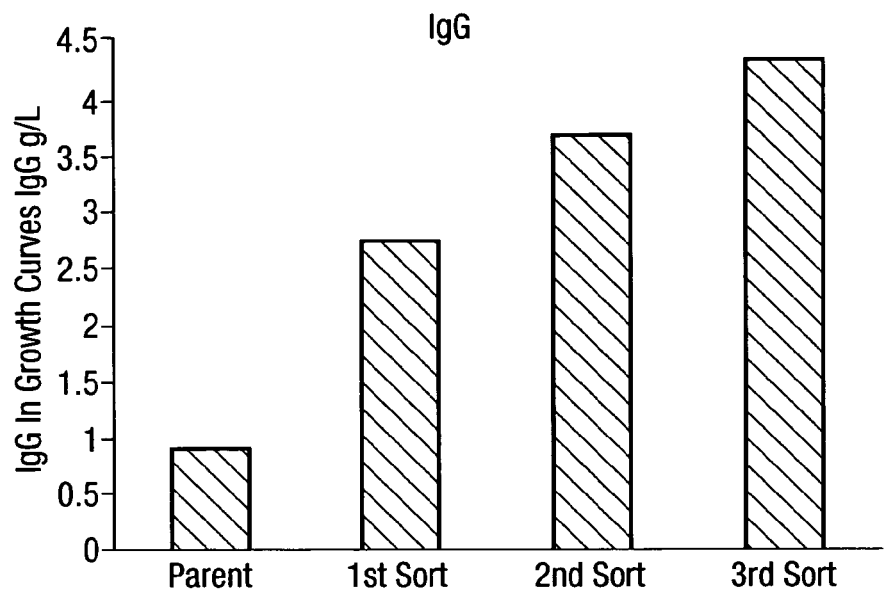
FIG. 18A shows data for the re-cloning of an established cell line for Project 3M (parent line, BP0044 ine) after anti-IgG staining. Best production titre sublone data shown after 1st re-sort (line C1, Live High DyLight649 IgG sort), 2nd re-sort (line #8, HFA High FITC IgG sort) and 3rd re-sort (line #8-41, HFA High Dylight649 IgG sort).
Figure 18B:
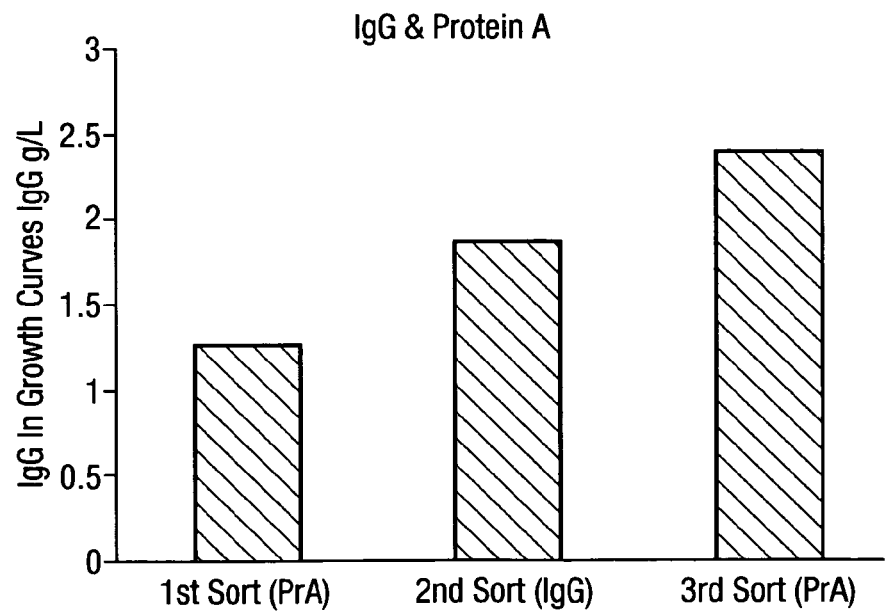
FIG. 18B shows data for the re-cloning of an established line for Project 12 after DyLight649 conjugated IgG or Alexa647 Protein A staining (as shown in the graph). Again best production titre subclone data shown after 1st sort (line BH83, HFA High Protein A sort), $2^{nd}$ sort (BH84, HFA High IgG sort) and 3rd sort (BH87, HFA High Protein A sort).

Improvement in Batch Titres Through Re-Sorting of Clones Using Anti-IgG and Protein A Although the staining achieved with the methotrexate amplified bulk transfection is relatively low with Protein A, the fluorescence signal is increased after single cell sorting. This facilitates the subsequent selection/re-cloning of high expressing cells. In addition the increase in fluorescence signal produced on Protein A staining increases with each separate step of single cell cloning (data not shown). Although re-sorting adds time to the protocol for cell line development, it has the advantage of producing clones that not only have increased titres but may also display enhanced stability over their 'parent' (representative example data shown in FIG. 14, Example 9). FIG. 18 shows the incremental increase observed in soluble IgG levels from growth curve studies of multiply sorted cells (sorted after Live or HFA cell gate implementation with or without anti-IgG or Protein A staining—as indicated in FIG. 18 legend).

The increase in IgG titre was further analysed for Project 3M and was shown to correspond with an increase in mean SPR value taken over 3-5 separate passages—see Table 16 below—with the exception of the first re-sort, where the increase in titre was due to increased cell count.

TABLE 16

Improvement in IgG specific productivity after sequential re-sorts of an initial bulk transfection (Project 12) and an established line(Project 3M) using anti-human IgG antibody staining and gating for HFA cells

| | Mean SPR Value After Sorting (pg/c/d) | |
|---|---|---|
| | Project 12 | Project 3M |
| 1$^{st}$ Sort | 10.0 | 17.0 |
| 2$^{nd}$ Sort | 19.0 | 17.1 |
| 3$^{rd}$ Sort | 22.9 | 29 |

The data described in this example demonstrate the benefits of multiple re-cloning rounds to increase productivity (and stability if required) of cell lines. They also support the possibility that additional re-clonings, beyond and above 3, could increase production titres even further.

Example 13

Comparison of FACS and Selection from CLONEPIX (Semi Solid Media) for the Selection of High Expressing Cells ARH77 cells were bulk transfected, using the Amaxa nucleofection kit, with a vector encoding a membrane protein, arbitrarily named herein 'protein X'. Stable transfectants were subsequently either (A) single cell FACS sorted (Live—LFA cells) after labelling with PE conjugated anti-'protein X' antibody or (B) clone picked from semi-solid media containing a DyLight-649 conjugated anti-'protein X' detection antibody. For (A), cells were stained with the anti-'protein X' antibody and both the brightest and the dimmest positive cells were single cell sorted in 96-well format in 50% conditioned media. For (B) 1e5 cells were plated in a Petri dish in Genetix semi-solid media containing supplements and also the detection antibody. The brightest clones were picked according to manufacturer's instructions 7-10 days post-plating.

The fluorescence of the clones selected from Clonepix was compared to both low and high expressing clones selected from the FACS cloning. FIG. 19 shows the mean fluorescence intensity (MFI) of all the clones, as measured by FACS analysis using the same anti-'protein X' antibody used previously for the FACS sort. The results demonstrate that the FACS method results in the identification/selection of much higher expressing clones. In fact, the highest expressing FACS-derived clone had an MFI that was 6 times higher than the highest expressing Clonepix-derived clone.

Example 14

Using the FSC-A Gate and Also Refining the % Sort Gate

To investigate the correlation between protein A-stained cells exhibiting the highest levels of fluorescence intensity and resulting clone productivity and thus to define the optimal gating parameters for single cell sorting, a sort was performed using cells bulk-transfected with plasmids encoding a monoclonal antibody and selected and amplified using the protocol described previously. The bulk-transfected cells were first gated on the live and then the HFA subpopulation (in an FSC-H vs. FSC-A plot), and subsequently sorted according to the % of protein A cell surface staining. Cells exhibiting the top 10%, 5%, 2% and 1% of fluorescence respectively were single-cell cloned into 96-well plates (FIG. 22).

In addition, as an alternate gating method, a sub-gate was set within the live cell population (in the FSC-A vs SSC-A plot) so as to incorporate all cells with high FSC-A characteristics. This included low and high SSC-A cells. These high FSC-A cells are a sub-fraction of the HFA subpopulation. These cells were subsequently assessed for protein A cell surface staining and cells exhibiting fluorescence within the top 5% fluorescence (as set for the live gate) were single cell sorted into 96-well plates (FIG. 22).

Figure 23A:
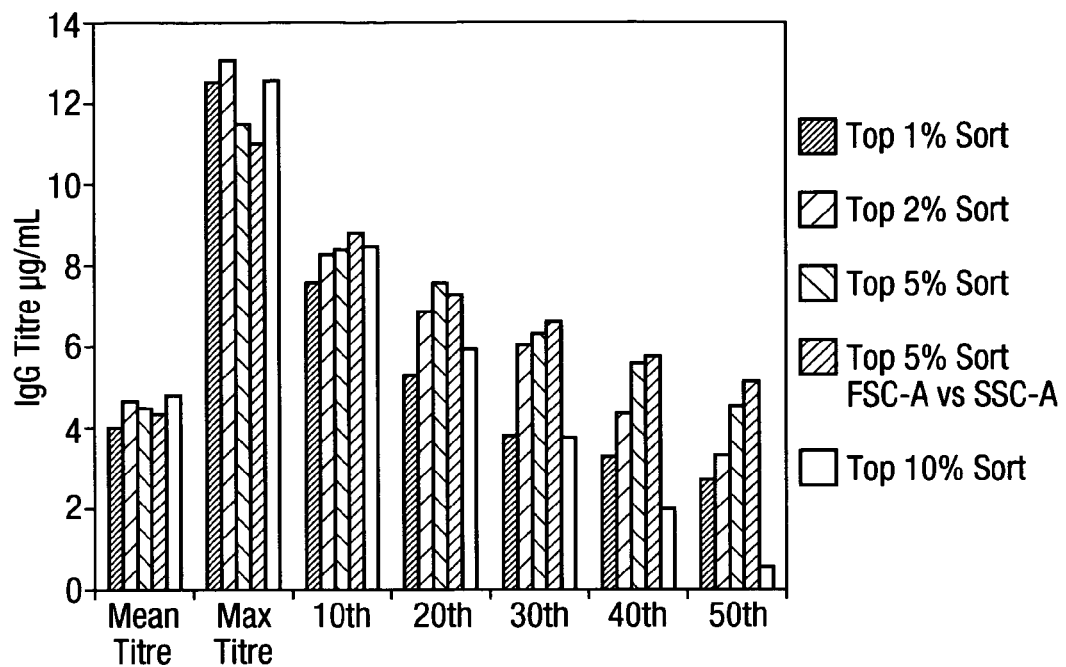
FIG. 23A Mean and maximum titres at the 96-well stage are equivalent for cells sorted from the top 10% (white), 5% (mid-grey), 2% (light-grey) and 1% (black) fluorescence gates. No differences in productivity at this stage are observed between the top 5% of Protein-A stained cells sorted from either the FSC-A vs. FSC-H or FSC-A vs. SSC-A HFA gates.
Figure 23B:
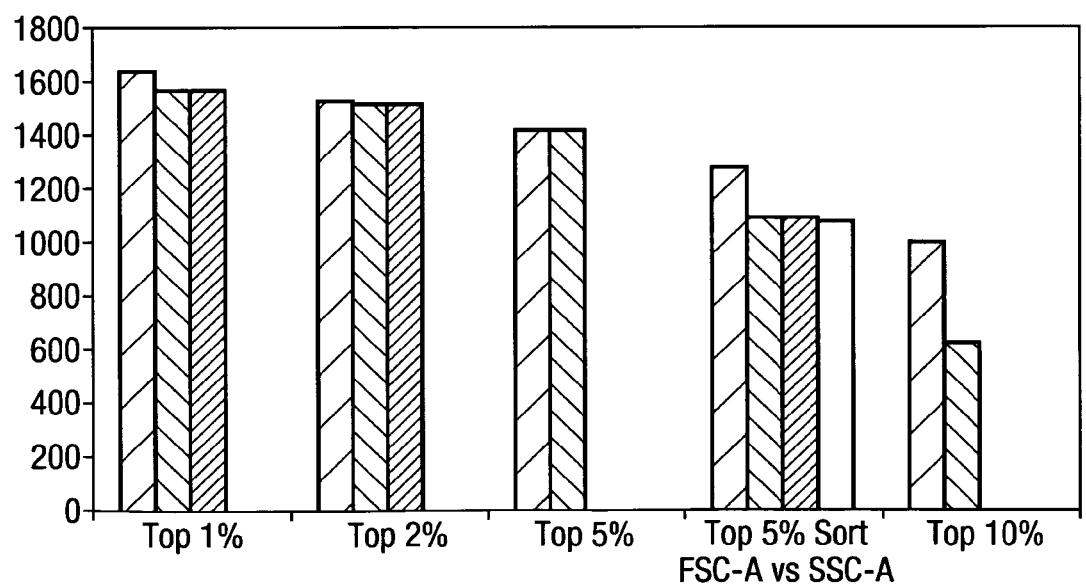
FIG. 23B IgG titres following batch production curves for the highest expressing clones, for each of the sort criteria, scaled-up to shake flask culture. Minimal differences with regards productivity are observed for each of the sort criteria although the data shows a trend for levels of IgG production correlating to levels of surface staining. This data also shows that the HFA population can also be identified by gating high FSC-A cells directly using the FSC-A vs. SSC-A dotplot.

Analysis of productivity at the 96-well stage revealed minimal differences with regards the mean and max titres recorded for cell clones sorted from either the differing % fluorescence intensity gates or from the high FSC-A and top 5% protein A staining gates (FIG. 23). IgG production in supplemented batch shake flask cultures of the highest-producing clones also revealed minimal differences amongst the different sorting criteria; although a trend was observed with regards levels of cell surface staining correlating with product yield. This data also demonstrates that clones of similar productivity may be isolated through gating cell populations on the basis of high FSC-A from either an FSC-H vs. FSC-A plot or an FSC-A vs SSC-A plot.

Example 15

The Use of Protein G

We further sought to evaluate the possibility to use other reagents for staining/identification/sorting of high producing cells. For this purpose we evaluated Protein G. Protein G Alexa488 was purchased from Invitrogen (Cat # P11065) and, after titration, optimal staining was found to be achieved with 0.25-0.5 μg of Protein G per $10^6$ cells. As seen in FIG. 24, good labelling (and comparable to Protein A) was achieved with Protein G. The data produced is in keeping with the soluble antibody levels secreted from the cells with the clonal cell line (higher producer) showing high levels of fluorescence with the labelled Protein G (and Protein A) in contrast to the low levels observed with the low producing bulk population. As with Protein A in previous examples, greater Protein G fluorescence was observed in the HFA gated population. In summary, like Protein A, protein G should be suitable for use as a labelling reagent and to sort high IgG expressing CHO cells from bulk or pre-cloned lines.

The invention claimed is:

1. A method for selecting one or more mammalian cells expressing secreted antibody for use as a biopharmaceutical, the method comprising the steps of:
   (a) providing a population of mammalian cells in a medium free from animal-derived components, wherein the cell population comprises at least one cell expressing said secreted antibody;
   (b) contacting the cell population with a label which directly binds to said antibody on the surface of the cell;
   (c) detecting said label bound to the antibody on the surface of said cell; and
   (d) selecting said cell based on the presence of said label bound to the antibody on the surface of said cell;
   wherein the label is selected from the group consisting of Protein A, Protein G or Protein L; and whereby one or more mammalian cells expressing a secreted antibody for use as a biopharmaceutical is selected.

2. The method according to claim 1, wherein said Protein A, Protein G or Protein L is fluorescent.

3. The method according to claim 1, wherein the detecting step comprises detecting a relative amount of said label bound to the surface of said cell.

4. The method according to claim 1, wherein the selecting step comprises selecting the cell or cells from the population which show the highest amount of label bound thereto.

5. The method according to claim 1, further comprising the step of:
   (e) isolating said selected cell or cells from the population of cells.

6. The method according to claim 1, wherein the secreted antibody is a domain antibody.

7. The method according to claim 1, wherein the mammalian cell is selected from the group consisting of CHO, CHO K1, CHO DG44, NSO, COS-1, COS-7, H EK293, H K21, PerC6, H EK293, 293T, Vero, AGE1.CR, HT1080, TE671, Namalwa, and SP2/0.

8. The method according to claim 1, wherein the steps of detecting, selecting and/or isolating said cell is carried out by fluorescence activated cell sorting.

9. The method according to claim 8, wherein said label is fluorescent Protein A, Protein G, or Protein L; wherein the step of detection comprises determining a relative fluorescence of said label bound to the antibody on the surface of the cell, wherein a relatively higher fluorescence is indicative of a higher relative expression of said antibody; and wherein selection step comprises selecting the cell or cells from the population that have a relatively higher level of fluorescence.

* * * * *